US012560592B2

(12) United States Patent
Parigoris et al.

(10) Patent No.: US 12,560,592 B2
(45) Date of Patent: Feb. 24, 2026

(54) STABLY-INVERTED ORGANOIDS AND METHODS OF PRODUCING AND USING THE SAME

(71) Applicant: Georgia Tech Research Corporation, Atlanta, GA (US)

(72) Inventors: Eric Scott Parigoris, Atlanta, GA (US); Ji Hoon Lee, Atlanta, GA (US); Soojung Lee, Atlanta, GA (US); David Mertz, Atlanta, GA (US); Shuichi Takayama, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 581 days.

(21) Appl. No.: 17/925,998

(22) PCT Filed: May 21, 2021

(86) PCT No.: PCT/US2021/033735
§ 371 (c)(1),
(2) Date: Nov. 17, 2022

(87) PCT Pub. No.: WO2021/237136
PCT Pub. Date: Nov. 25, 2021

(65) Prior Publication Data
US 2023/0194506 A1      Jun. 22, 2023

Related U.S. Application Data

(60) Provisional application No. 63/028,895, filed on May 22, 2020.

(51) Int. Cl.
*G01N 33/50* (2006.01)
*C12N 5/071* (2010.01)

(52) U.S. Cl.
CPC ....... *G01N 33/5082* (2013.01); *C12N 5/0697* (2013.01); *C12N 2501/11* (2013.01); *C12N 2513/00* (2013.01); *C12N 2533/90* (2013.01)

(58) Field of Classification Search
None
See application file for complete search history.

(56) References Cited

U.S. PATENT DOCUMENTS

| | | |
|---|---|---|
| 2014/0170745 A1 | 6/2014 | Chan et al. |
| 2018/0030409 A1 | 2/2018 | Lewis et al. |
| 2018/0245050 A1 | 8/2018 | Freedman et al. |

FOREIGN PATENT DOCUMENTS

WO      2020/041065 A1      2/2020

OTHER PUBLICATIONS

International Search Report and Written Opinion from Application No. PCT/US2021/033735 dated Nov. 12, 2021.
(Continued)

*Primary Examiner* — David W Berke-Schlessel
(74) *Attorney, Agent, or Firm* — TROUTMAN PEPPER LOCKE LLP; Ryan A. Schneider; Nicholas H. Doss

(57) ABSTRACT

An exemplary embodiment of the present disclosure provides a 3D structure comprising a tissue layer having a first surface defining an interior chamber and an opposing second surface supporting a first plurality of cells outwardly positioned from the interior chamber, wherein the interior chamber comprises an extracellular matrix mixture. The present disclosure also provides a method of making a 3D structure, the method comprising mixing an extracellular matrix mixture at a first temperature with a culture medium at a second temperature, the second temperature greater than the first temperature, culturing a first plurality of cells in the extracellular matrix mixture and culture medium, and forming a 3D structure having an interior chamber enclosed by the first (Continued)

plurality of cells configured to interface with an environment external to the 3D structure.

19 Claims, 50 Drawing Sheets

(56) References Cited

OTHER PUBLICATIONS

Parigoris, et al., "Cancer Cell Invasion of Mammary Organoids with Basal-In Phenotype," Advanced Healthcare Materials Jun. 25, 2020 vol. 10, No. 4.

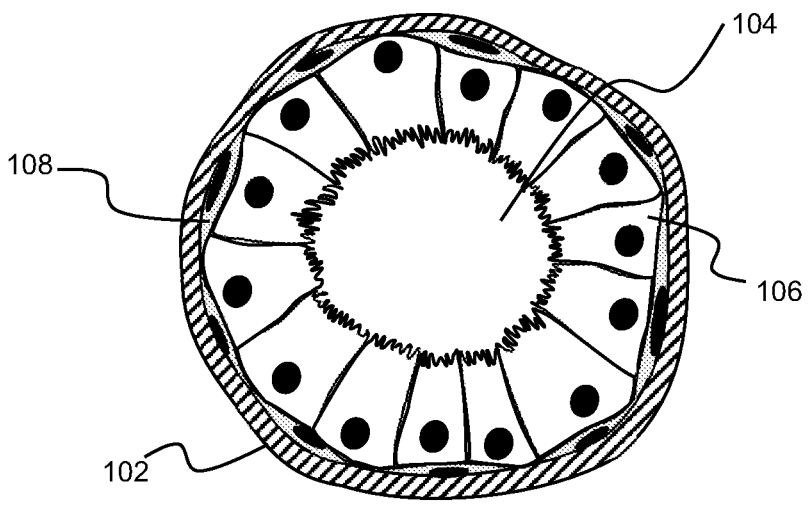
104
108
106
102
FIG. 1A – Prior Art
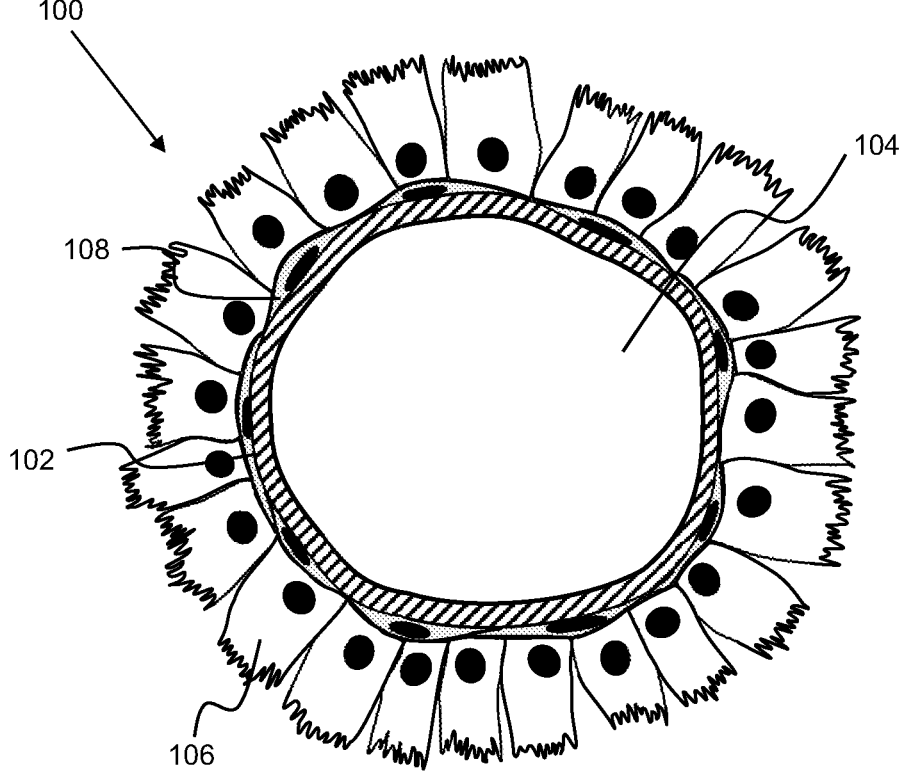
100
104
108
102
106
FIG. 1B

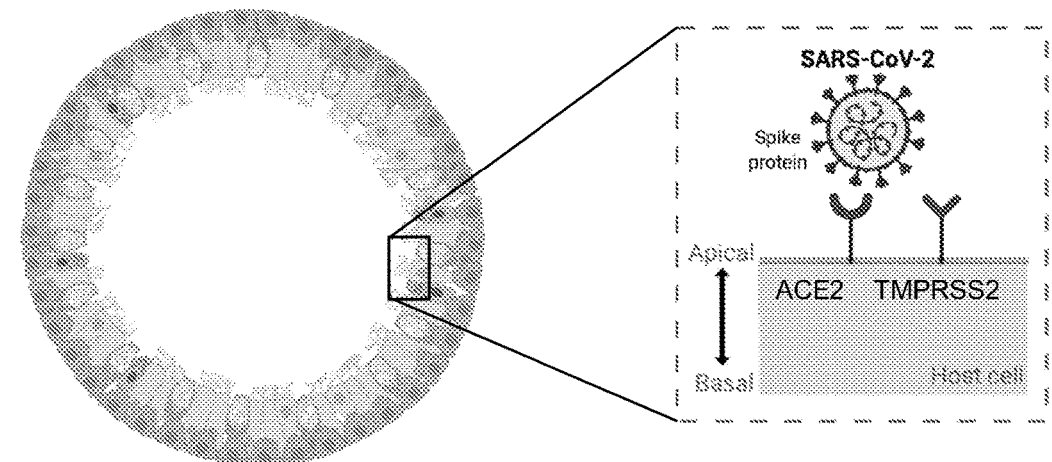
FIG. 1C – Prior Art
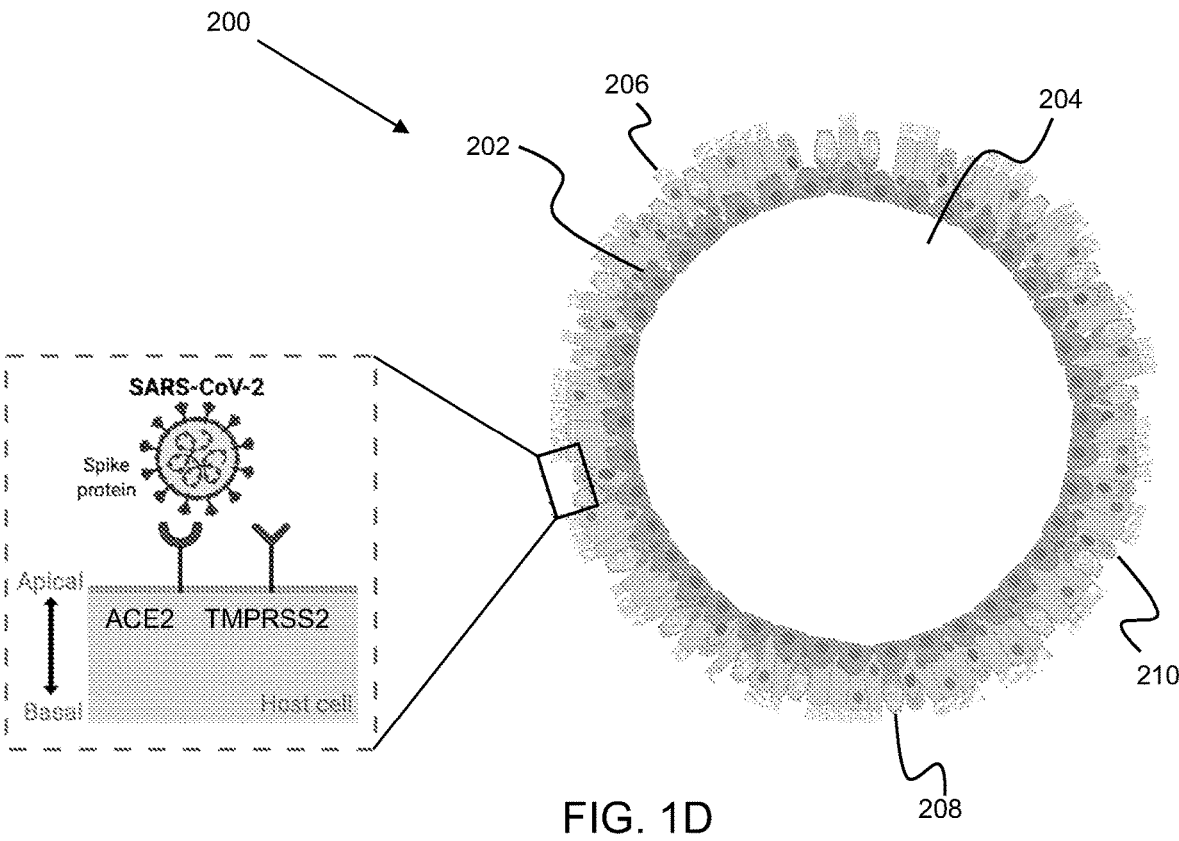
FIG. 1D

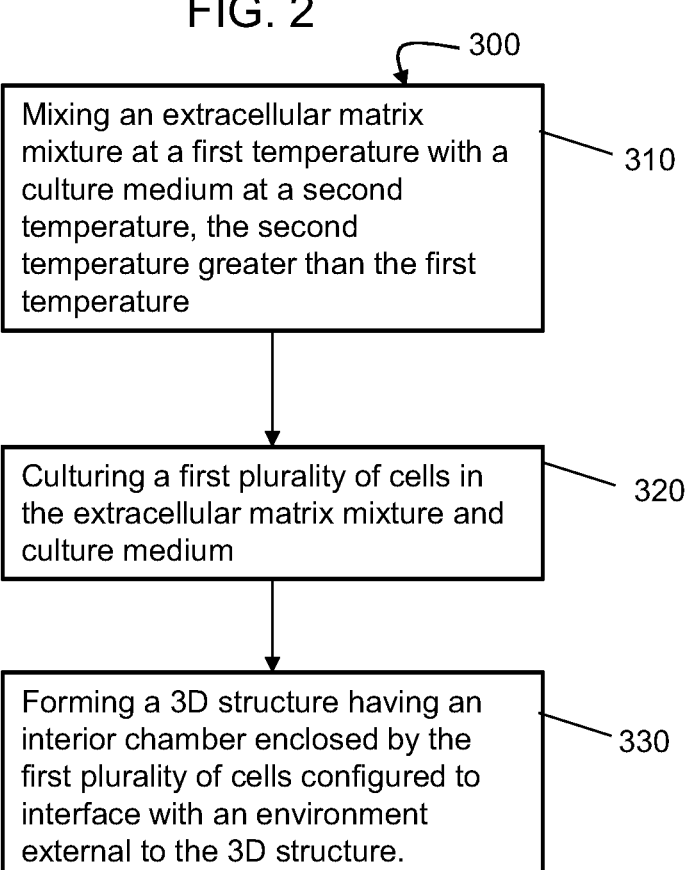

Mixing an extracellular matrix mixture at a first temperature with a culture medium at a second temperature, the second temperature greater than the first temperature    310

Culturing a first plurality of cells in the extracellular matrix mixture and culture medium    320

Forming a 3D structure having an interior chamber enclosed by the first plurality of cells configured to interface with an environment external to the 3D structure.    330

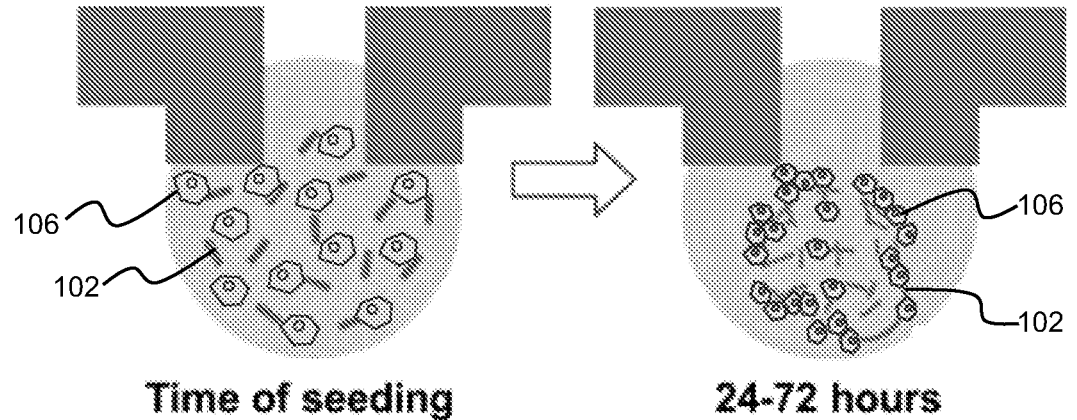
106
102
Time of seeding
24-72 hours
106
102
FIG. 4A
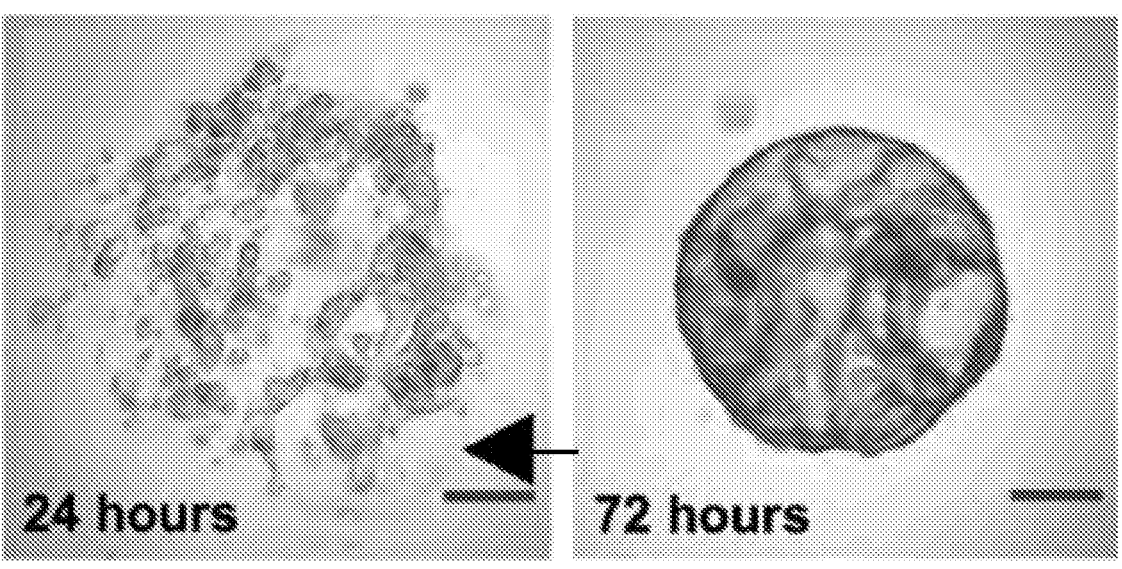
24 hours
72 hours
FIG. 4B                    FIG. 4C

106

106

Time of seeding       72 hours

106
102

Time of seeding 106
102

72 hours

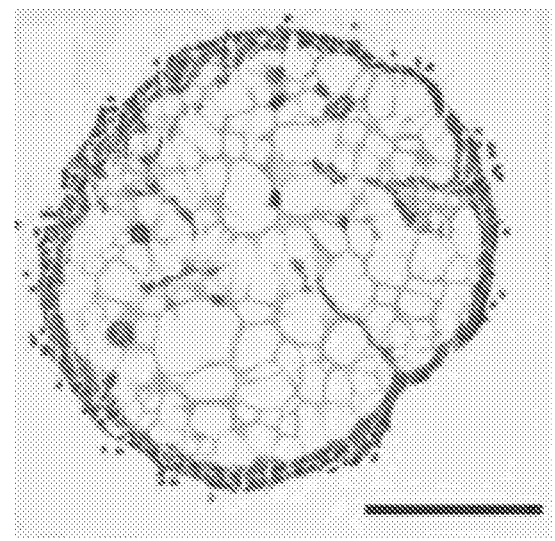
FIG. 7A
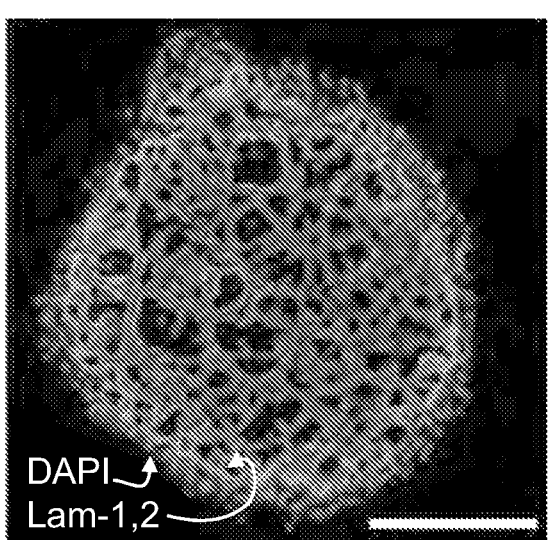
FIG. 7B
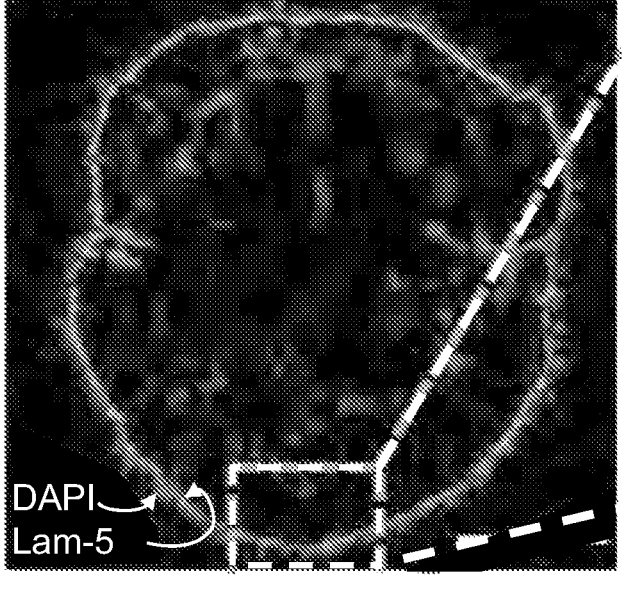
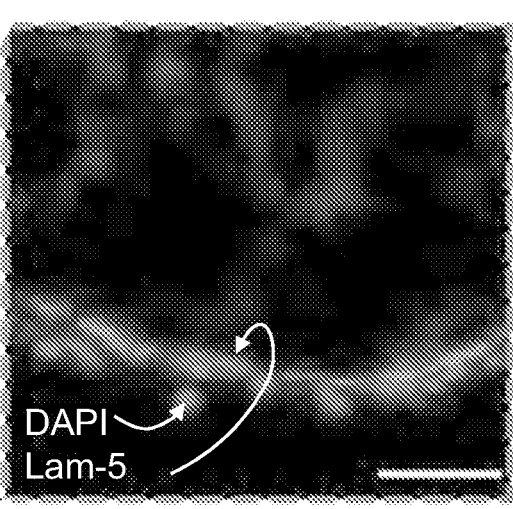
FIG. 8A

No Matrigel
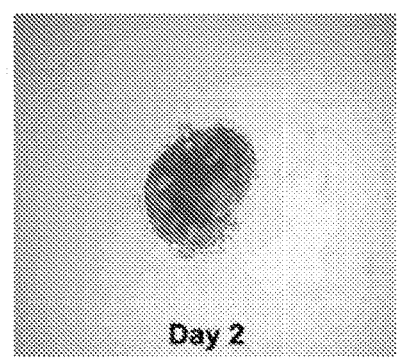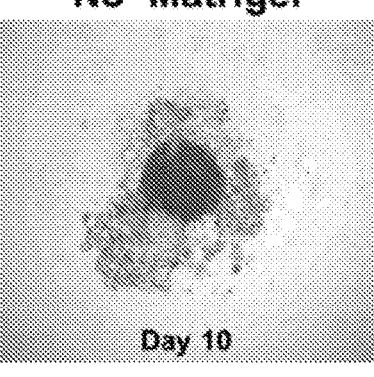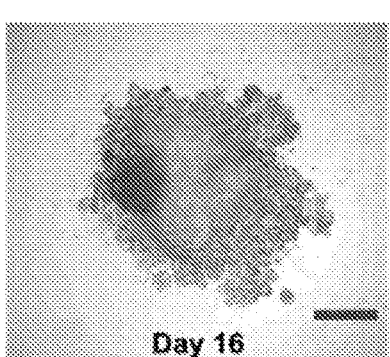
FIG. 9A
1.5% Matrigel
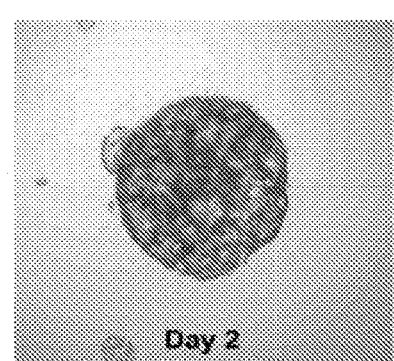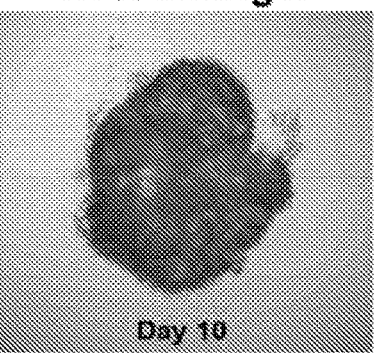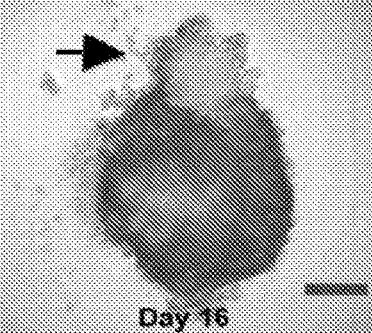
FIG. 9B

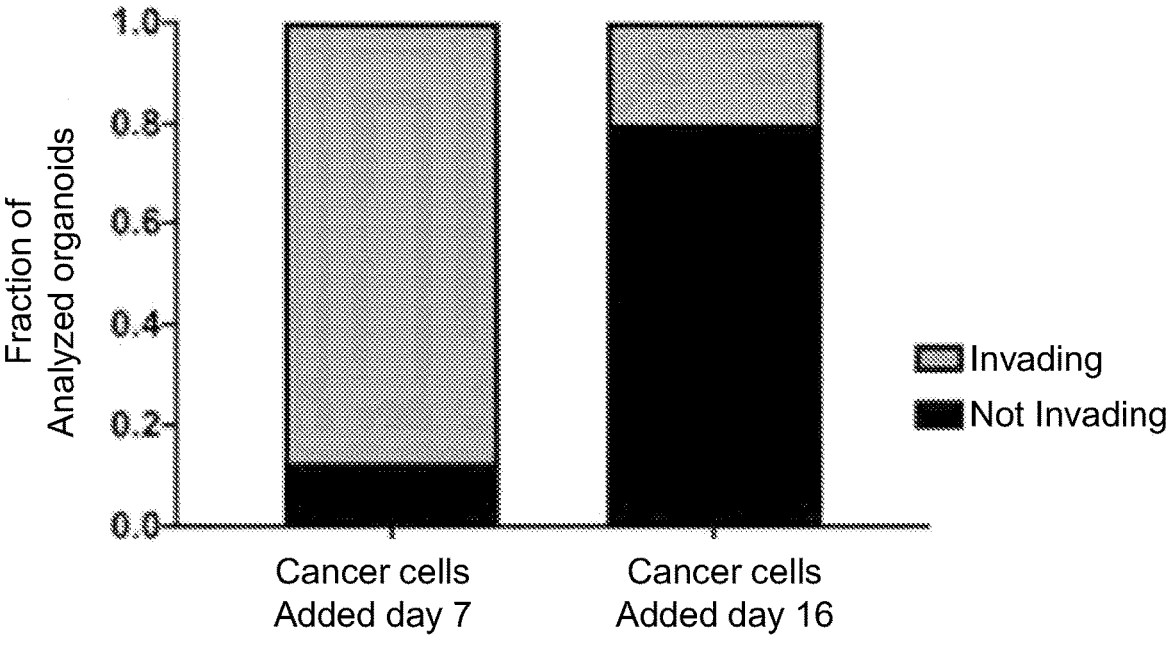
FIG. 20
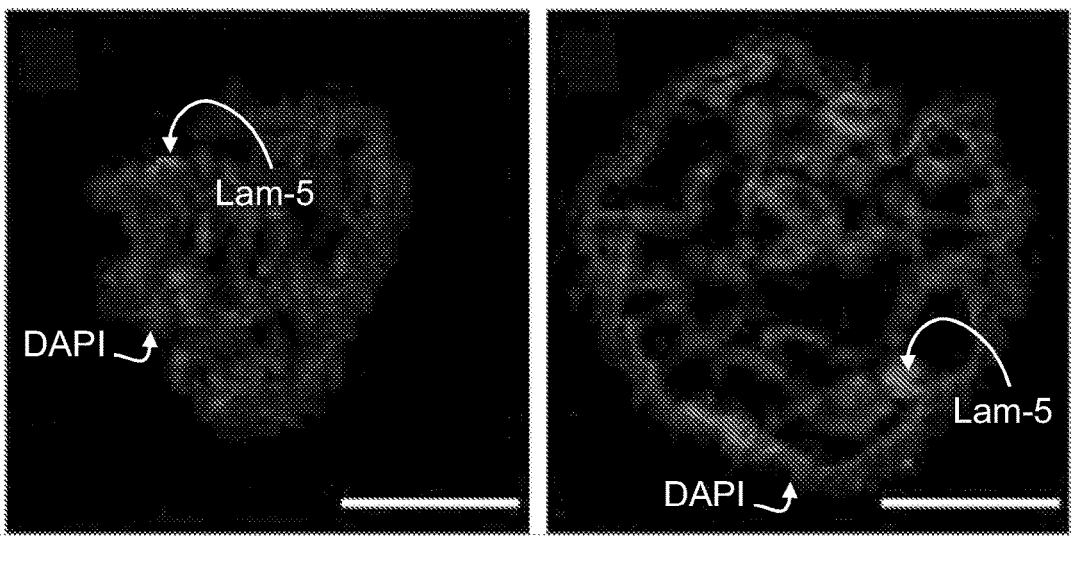
FIG. 21A                    FIG. 21B

Day 51
Organoid
     Day 51
Organoid
     Day 51
Organoid

Loading PDMS mixture     Evaporation Solvent     PDMS curvature

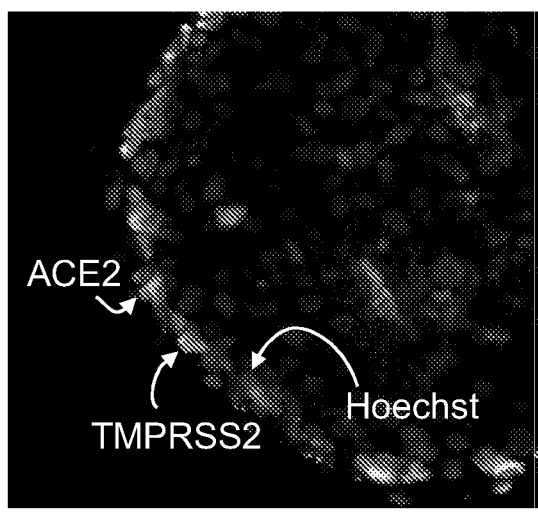
FIG. 39
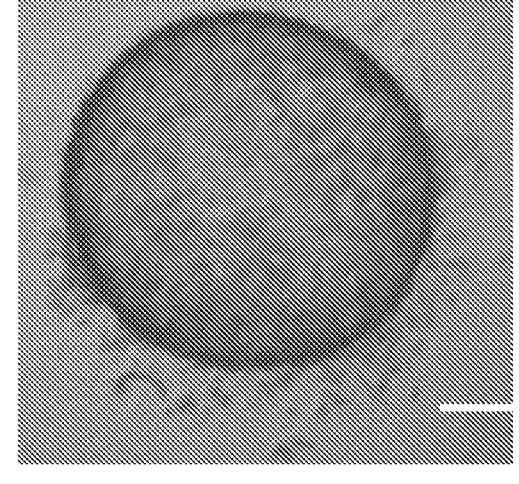
FIG. 40A
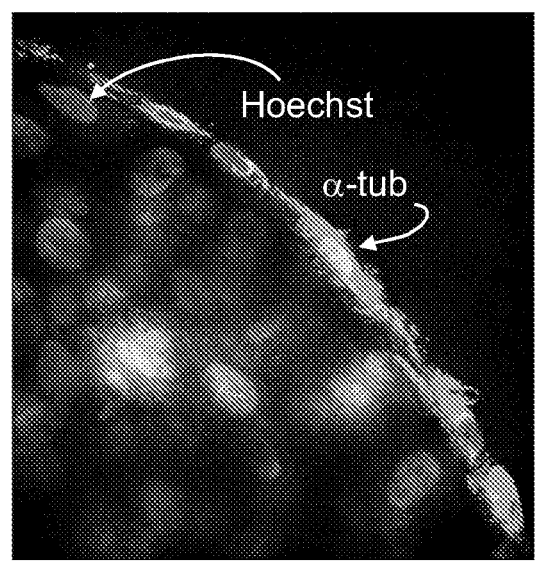
FIG. 40B
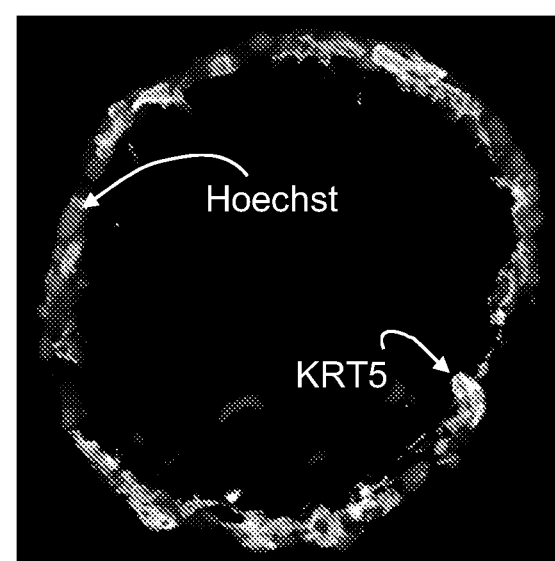
FIG. 40C

STABLY-INVERTED ORGANOIDS AND METHODS OF PRODUCING AND USING THE SAME

CROSS-REFERENCE TO RELATED APPLICATIONS

This application claims the benefit of U.S. Provisional Application Ser. No. 63/028,895, filed on 22 May 2020, which is incorporated herein by reference in its entirety as if fully set forth below.

FEDERALLY SPONSORED RESEARCH STATEMENT

This invention was made with government support under grant/award number R01CA196018, awarded by the National Institutes of Health, grant/award number R01HL136141, awarded by the National Institutes of Health, and grant/award number CBET-093951, awarded by National Science Foundation. The government has certain rights in the invention.

FIELD OF THE DISCLOSURE

The various embodiments of the present disclosure relate generally to three-dimensional (3D) tissue organoid systems and methods for making the same, and more particularly to inverted, basal-out 3D tissue organoid systems and methods for making the same.

BACKGROUND

Three-dimensional organoids are self-organized cell structures grown in vitro from stem and/or progenitor cell-containing tissue samples and recapitulate key features of the development and performance of native organs. Organoids can be cultured within several days or weeks and can provide researchers with scalable platforms for studying the development of infections and/or perform high-throughput drug screenings. In vitro models, such as organoids, are highly sought after due to their low-cost and ease for assessing basic cell proliferation and invasion functions of cancer as well as bacterial and viral infections. Additionally, organoids cultured from tissues from a patient allow for precision drug testing.

In general, organoid culturing suffers from lack of uniformity in size and shape and cellular composition and inconvenience in handling. Additionally, studying of cancer, bacterial, or viral infection can be difficult due to the precision required to access the interior surface, or lumen, of an organoid. Self-organized organoids are typically spherically or non-spherically structured with interiors that are hollow or only partially cell-filled, and have an apical-in polarity, where the cells are facing the interior lumen of the organoid. In many apical-in structures, a basement membrane will form around the basal side, or facing away from the interior lumen of the organoid. In particular, the transition from noninvasive to invasive epithelial cancers, such as ductal carcinoma in situ (DCIS), is characterized by invasion out of the lumen of a duct through the epithelial cells and then the basement membrane. Doing so requires micro-injections of the cancer cells of interest into the lumen of the micrometer-sized organoid. Accordingly, there is a need to develop robust systems and methods for assessing cancer, bacterial, or viral invasion as well as drug screening platforms using organoids that allow easier access to the apical surface.

Inverted spherical 3D tissue models with a hollow lumen and epithelial cells exposed to the exterior surface, referred to as apical-out, have been developed to address the need for easier invasion studies by providing access the epithelial cells without the requirement of microinjections. The method described herein generates high-throughput, stably-inverted organoids that can also address the uniformity of shape (spherical) and size and convenience challenges of producing typical apical-in organoids.

BRIEF SUMMARY

The present disclosure relates to stably-inverted organoids. An exemplary embodiment of the present disclosure provides a 3D structure comprising a tissue layer and an opposing second surface. The tissue layer can have a first surface defining an interior chamber. The opposing second surface can support a first plurality of cells outwardly positioned from the interior chamber. The interior chamber can comprise an extracellular matrix mixture.

In any of the embodiments disclosed herein, the tissue layer can comprise a basement membrane matrix.

In any of the embodiments disclosed herein, the first surface can further comprise stromal cells.

In any of the embodiments disclosed herein, the first surface can further comprise a transmembrane receptor.

In any of the embodiments disclosed herein, the opposing second surface can comprise an apical cell marker.

In any of the embodiments disclosed herein, the opposing second surface can further comprise a cell.

In any of the embodiments disclosed herein, the cell can be configured to express an ACE2, a TMPRSS2, a mucin, a transporter, a receptor, an alpha-tubulin, an acetylated alpha-tubulin, or combinations thereof.

In any of the embodiments disclosed herein, the first plurality of cells can comprise epithelial cells.

In any of the embodiments disclosed herein, the epithelial cells can comprise mammary cells, kidney cells, lung cells, bladder cells, bronchial cells, tracheal cells, alveolar cells, corneal cells, prostate cells, renal cells, vaginal cells, cervical cells, intestine cells, or combinations thereof.

In any of the embodiments disclosed herein, the first plurality of cells can comprise endothelial cells.

In any of the embodiments disclosed herein, the endothelial cells can comprise primary coronary artery cells, primary pulmonary artery cells, primary aortic cells, primary dermal microvascular cells, primary umbilical vein cells, brain artery cells, brachiocephalic artery cells, internal thoracic artery cells, lymphatic endothelial cells, or combinations thereof.

In any of the embodiments disclosed herein, the 3D structure can further comprise a second plurality of cells positioned within the 3D structure.

In any of the embodiments disclosed herein, can further comprise the second plurality of cells positioned between the tissue layer and the first plurality of cells.

In any of the embodiments disclosed herein, the second plurality of cells can comprise basal cells.

In any of the embodiments disclosed herein, the second plurality of cells can comprise stromal cells.

In any of the embodiments disclosed herein, the stromal cells can comprise one or more of myoepithelial cells, adipocytes, fibrocytes, fibroblasts, myofibroblasts, pericytes, mesenchymal stem cells, macrophages, mast cells, and lymphocytes.

In any of the embodiments disclosed herein, the 3D structure can comprise a diameter of about 100 μm to about 5 mm.

An exemplary embodiment of the present disclosure provides an organoid comprising an interior chamber of an organoid enclosed in a first plurality of cells forming an external surface of the organoid. The first plurality of cells can be configured to interface with an environment external to the organoid.

In any of the embodiments disclosed herein, the organoid can further comprise a tissue layer positioned between the interior chamber of the organoid and the first plurality of cells. The tissue layer can be configured to interface with the interior chamber of the organoid.

In any of the embodiments disclosed herein, the tissue layer can comprise a basement membrane matrix.

In any of the embodiments disclosed herein, the tissue layer can comprise stromal cells.

In any of the embodiments disclosed herein, the tissue layer can comprise a transmembrane receptor.

In any of the embodiments disclosed herein, the interior chamber can comprise an extracellular matrix mixture.

In any of the embodiments disclosed herein, the extracellular matrix mixture can comprise one or more of collagen, elastin, fibronectin, and laminin.

In any of the embodiments disclosed herein, the first plurality of cells can comprise epithelial cells.

In any of the embodiments disclosed herein, the epithelial cells can comprise mammary cells, kidney cells, lung cells, bladder cells, bronchial cells, tracheal cells, alveolar corneal cells, prostate cells, renal cells, vaginal cells, cervical cells, intestine cells, or combinations thereof.

In any of the embodiments disclosed herein, the first plurality of cells can comprise endothelial cells.

In any of the embodiments disclosed herein, the endothelial cells can comprise primary coronary artery cells, primary pulmonary artery cells, primary aortic cells, primary dermal microvascular cells, primary umbilical vein cells, brain artery cells, brachiocephalic artery cells, internal thoracic artery cells, lymphatic endothelial cells or combinations thereof.

In any of the embodiments disclosed herein, the organoid can further comprise a second plurality of cells positioned within the organoid.

In any of the embodiments disclosed herein, the second plurality of cells can comprise stromal cells.

In any of the embodiments disclosed herein, the stromal cells can comprise one or more of myoepithelial cells, adipocytes, fibrocytes, fibroblasts, myofibroblasts, pericytes, mesenchymal stem cells, macrophages, mast cells, and lymphocytes.

In any of the embodiments disclosed herein, the organoid can have a diameter of about 100 μm to about 5 mm.

An exemplary embodiment of the present disclosure provides a method of making a 3D structure. The method can comprise mixing an extracellular matrix mixture at a first temperature with a culture medium at a second temperature, culturing a first plurality of cells in the extracellular matrix mixture and culture medium, and forming a 3D structure having an interior chamber enclosed by the first plurality of cells configured to interface with an environment external to the 3D structure. The second temperature can be greater than the first temperature.

In any of the embodiments disclosed herein, the step of forming a 3D structure having an interior chamber enclosed by the first plurality of cells configured to interface with an environment external to the 3D structure can further comprise entrapping the extracellular matrix mixture within the interior chamber of the 3D structure.

In any of the embodiments disclosed herein, the method can further comprise forming a tissue layer between the first plurality of cells and the interior chamber of the 3D structure.

In any of the embodiments disclosed herein, the step of mixing an extracellular matrix mixture can comprise mixing less than 1 mg/mL of the extracellular matrix mixture with the culture medium.

In any of the embodiments disclosed herein, the step of mixing an extracellular matrix mixture can comprise mixing less than 500 μg/mL of the extracellular matrix mixture with the culture medium.

In any of the embodiments disclosed herein, the step of mixing an extracellular matrix mixture at a first temperature with a culture medium at a second temperature, the second temperature greater than the first temperature can further comprise heating the culture medium to the second temperature.

In any of the embodiments disclosed herein, the second temperature can be from about 20° C. to about 40° C.

In any of the embodiments disclosed herein, the second temperature can be from about 25° C. to about 37° C.

In any of the embodiments disclosed herein, the step of culturing a first plurality of cells in the extracellular matrix mixture and culture medium can comprise culturing is a non-stick surface culture system.

In any of the embodiments disclosed herein, the non-stick surface culture system can comprise one or more of a hanging drop system, an ultra-low attachment system, a hydrogel well system, and an ultrasound levitation system.

In any of the embodiments disclosed herein, the step of culturing a first plurality of cells in the extracellular matrix mixture and culture medium can further comprise culturing a second plurality of cells simultaneously with culturing the first plurality of cells.

In any of the embodiments disclosed herein, the step of culturing a first plurality of cells in the extracellular matrix mixture and culture medium can further comprise culturing a second plurality of cells after culturing the first plurality of cells.

In any of the embodiments disclosed herein, the step of forming a 3D structure having an interior chamber enclosed by the first plurality of cells configured to interface with an environment external to the 3D structure can comprise about 5% of the first plurality of cells interfacing with an environment external to the 3D structure.

In any of the embodiments disclosed herein, the step of forming a 3D structure having an interior chamber enclosed by the first plurality of cells configured to interface with an environment external to the 3D structure can comprise about 50% of the first plurality of cells interfacing with an environment external to the 3D structure.

In any of the embodiments disclosed herein, the step of forming a 3D structure having an interior chamber enclosed by the first plurality of cells configured to interface with an environment external to the 3D structure can comprise about 100% of the first plurality of cells interfacing with an environment external to the 3D structure.

In any of the embodiments disclosed herein, the method can further comprise exposing the 3D structure to a virus, a bacteria, a fungi, a cancer cell, an immune cell, a stem cell, a drug, or combinations thereof.

These and other aspects of the present disclosure are described in the Detailed Description below and the accompanying drawings. Other aspects and features of embodiments will become apparent to those of ordinary skill in the art upon reviewing the following description of specific, exemplary embodiments in concert with the drawings.

While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

FIG. 1A provides an example of a conventional apical-in 3D structure.

FIG. 1B provides an example apical-out organoid, in accordance with an exemplary embodiment of the present disclosure.

FIG. 1C provides an example of a conventional apical-in organoid.

FIG. 1D provides an example apical-out organoid with multiple cell types and an inset showing a schematic of a viral infection, in accordance with an exemplary embodiment of the present disclosure.

FIG. 2 is a flow diagram illustrating a method of making organoids, in accordance with an exemplary embodiment of the present disclosure.

FIG. 4A shows a schematic representation of cell-assisted minimal scaffolding with $120\pm10$ µg/mL Matrigel added to warm media for organoid formation, in accordance with an exemplary embodiment of the present disclosure.

FIGS. 4B and 4C provide brightfield images of $120\pm10$ µg/mL Matrigel added to warm media for organoid formation, in accordance with an exemplary embodiment of the present disclosure.

FIG. 7A shows a hematoxylin and eosin stain (H&E) image of $120\pm10$ µg/mL Matrigel added to warm media for organoid formation at day 16, in accordance with an exemplary embodiment of the present disclosure.

FIG. 7B shows a Laminin-1,2 stained image of $120\pm10$ µg/mL Matrigel added to warm media for organoid formation at day 16, in accordance with an exemplary embodiment of the present disclosure.

FIG. 8A provides an image showing Laminin-5 staining of a day 16 organoid section with inset showing a 40× image, with laminin-5 layer on the inner side of the structure, in accordance with an exemplary embodiment of the present disclosure.

FIG. 9A provides self-organizing behaviors of epithelial cells and cancer cells co-culture and time course development without Matrigel according to conventional methods.

FIG. 9B provides self-organizing behaviors of epithelial cells and cancer cells co-culture and time course development with $120\pm10$ µg/mL Matrigel, in accordance with an exemplary embodiment of the present disclosure.

FIG. 20 shows a bar graph of fraction of day 7 and day 16 organoids invaded and not invaded by cancer cells, in accordance with an exemplary embodiment of the present disclosure.

FIG. 21A provides an image of Laminin-5 staining of the basement membrane development of organoids at day 8, in accordance with an exemplary embodiment of the present disclosure.

FIG. 21B provides an image of Laminin-5 staining of the basement membrane development of organoids at day 16, in accordance with an exemplary embodiment of the present disclosure.

FIG. 39 shows an immunofluorescence image of lung organoid showing varying types of cell markers, in accordance with an exemplary embodiment of the present disclosure.

FIG. 40A provides a brightfield image of day 8 lung organoid, in accordance with an exemplary embodiment of the present disclosure.

FIGS. 40B and 40C show immunofluorescence images of day 8 lung organoid showing various types of cell markers, in accordance with an exemplary embodiment of the present disclosure.

DETAILED DESCRIPTION

Figure 1E:
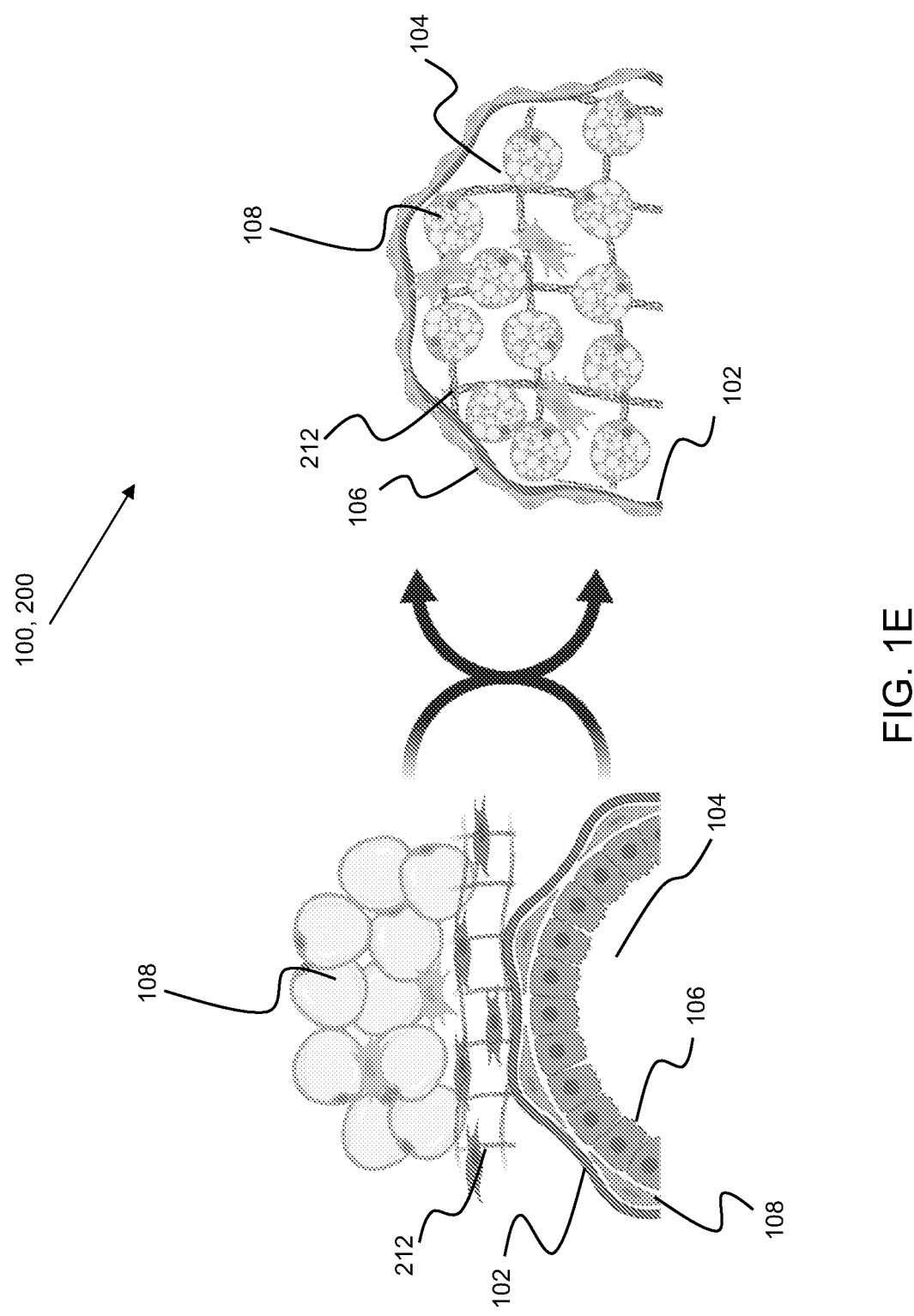
FIG. 1E provides a contrast between conventional apical-in epithelial tissue with external, basal-side stromal cells (left side) in contrast to an example of an apical-out organoid having a co-culture of stromal cells in its interior (right side), in accordance with an exemplary embodiment of the present disclosure.
Figure 3B:
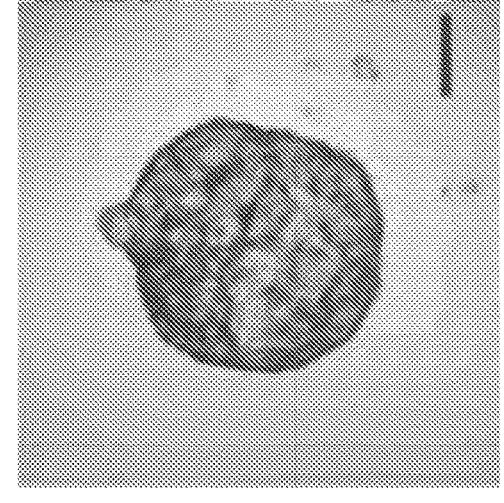
FIG. 3B shows a brightfield image of 3-day organoid formation with FBS with minimal Matrigel scaffolding, in accordance with an exemplary embodiment of the present disclosure.
Figure 3D:
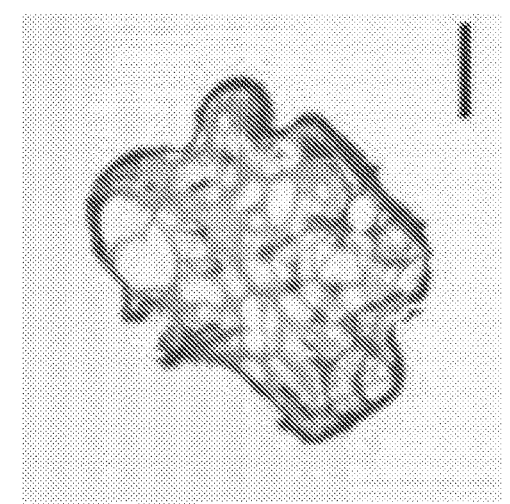
FIG. 3D shows a hematoxylin and eosin stain (H&E) image of 3-day organoid formation with FBS with minimal Matrigel scaffolding, in accordance with an exemplary embodiment of the present disclosure.
Figure 3A:
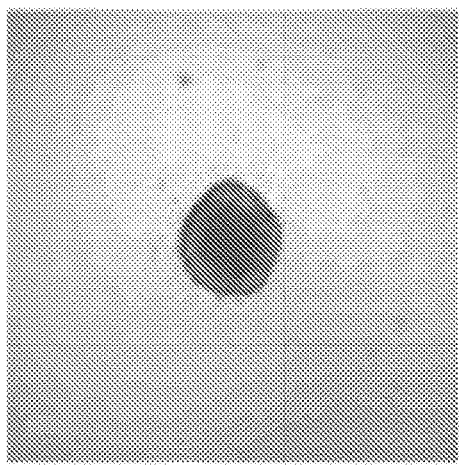
FIG. 3A shows a brightfield image of 3-day organoid formation with FBS without Matrigel, in accordance with conventional spheroid formation methods.
Figure 3C:
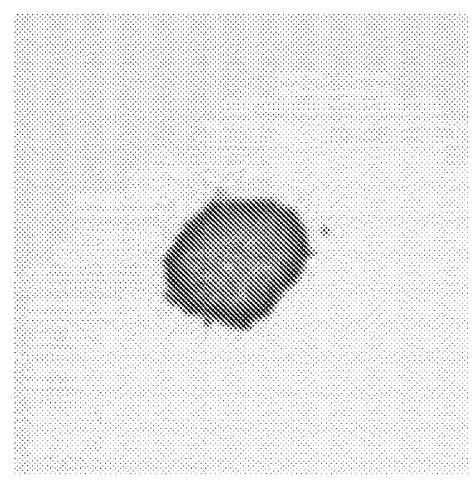
FIG. 3C shows a hematoxylin and eosin stain (H&E) image of 3-day organoid formation with FBS without Matrigel, in accordance with conventional spheroid formation methods.

To facilitate an understanding of the principles and features of the present disclosure, various illustrative embodiments are explained below. The components, steps, and materials described hereinafter as making up various elements of the embodiments disclosed herein are intended to be illustrative and not restrictive. Many suitable components, steps, and materials that would perform the same or similar functions as the components, steps, and materials described herein are intended to be embraced within the scope of the disclosure. Such other components, steps, and materials not described herein can include, but are not limited to, similar components or steps that are developed after development of the embodiments disclosed herein.

FIG. 1A illustrates a conventional 3D structure having a plurality of cells 106, such as epithelial cells, internally facing an interior chamber 104 of the 3D structure. In some apical-in organoids, the 3D structures also have cell-filled interiors. Typical 3D structures can also feature a second plurality of cells 108, such as myoepithelial cells, as well as an intact tissue layer 102, such as a basement membrane, as demonstrated in FIG. 1A. As previously discussed, invasion or drug screening studies monitor the progression first from the epithelial cells and then the basement membrane. Accordingly, using conventional apical-in 3D structures, like the one shown in FIG. 1, can be limited to microinjecting into the interior lumen 104 of the 3D structure.

FIG. 1B provides an example apical-out, or basal-in, 3D structure 100. In some embodiments, apical-out 3D structure 100 can be inverted such that the tissue layer 102, which usually is positioned outwardly facing in an apical-in 3D structure, is internal and defining the interior chamber 104 of the apical-out 3D structure 100. In the apical-out organization, the tissue layer 102 can be located on the interior surface and defining the interior chamber 104 of the 3D structure. The tissue layer 102 can be a sheet-like type of extracellular matrix that provides the 3D structure with cell and tissue support. The tissue layer 102 can have a first surface facing the interior chamber 104 of the 3D structure 100 and an opposing second surface which supports a first plurality of cells 106. In some embodiments, the tissue layer 102 can be uniformly developed and fully encapsulate the interior chamber 104. In some embodiments, the tissue layer 102 can form one or more partial layers and have gaps along the layer around the interior chamber 104. As would be appreciated by those of skill in the art, the 3D structure can be formed with or without a complete tissue layer 102 while still maintaining a spherical apical-out 3D structure. The inverted organoids are generally highly spherical (e.g., having circularity above about 0.8, above about 0.82, above about 0.84, above about 0.86, above about 0.88, and/or above about 0.9) due to epithelial transport of ions, molecules, and fluids from the apical side to the basolateral side that stretches the epithelium.

Figure 8B:
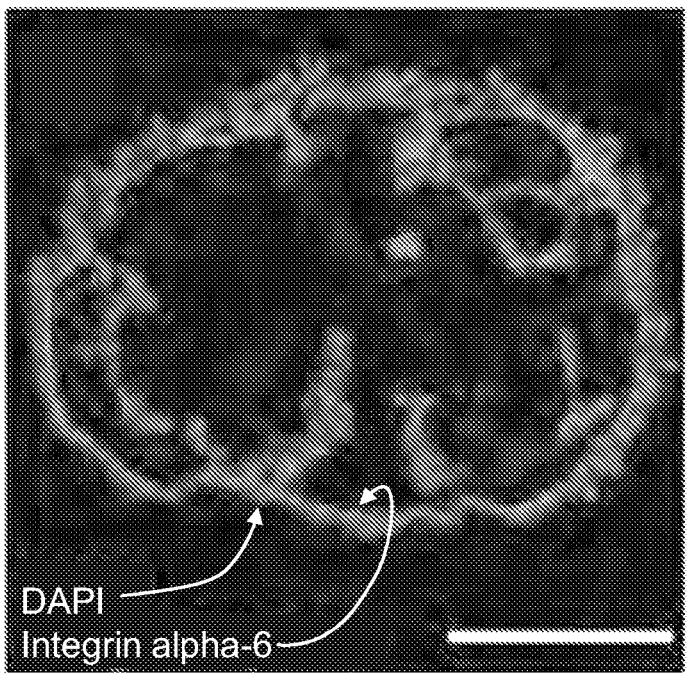
FIG. 8B provides an image showing Integrin alpha-6 staining of a day 16 organoid section, in accordance with an exemplary embodiment of the present disclosure.
Figure 8C:
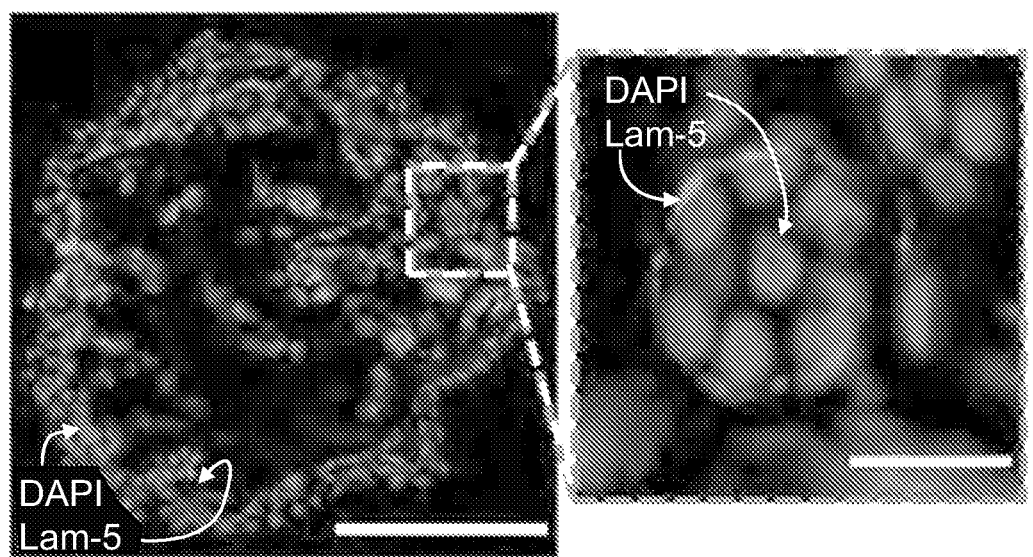
FIG. 8C provides an image showing Laminin-5 staining of a day 12 organoid with a lesser extent of hollowing, with inset showing a 40× image of internal acinar-like structures that do not exhibit a basal-in morphology, in accordance with an exemplary embodiment of the present disclosure.

In some embodiments, the tissue layer 102 can comprise a basement membrane of an organoid. In general, integrin alpha-6 staining can adhere to the basement membrane, as shown in FIG. 8B. Additionally, or alternatively thereto, laminin-5 can be used as an indicator of the basement membrane (e.g., FIG. 8C). In the apical-out organization, the first surface of the tissue layer 102 interacts with the interior chamber 104 of the 3D structure 100. In some embodiments, the cells adjacent to the first surface of the tissue layer can comprise basal cells, which face inward. As such, the cells and cell membranes adjacent to the tissue layer 102 can present certain basal cell markers and transmembrane receptor cell markers. As would be appreciated, the receptors and basal cell markers may be dependent on the type of first plurality of cells 106 or on the type of second plurality of cells 108 (e.g., cell markers on bronchial epithelial cells may vary from cell markers on kidney epithelial cells).

In any of the embodiments disclosed herein, the apical-out 3D structure 100 can have a first plurality of cells 106 supported on the second surface of the tissue layer 102 and outwardly positioned from the interior chamber 104. The first plurality of cells 106 can be on the external surface and interact with the environment of the 3D structure 100. The first plurality of cells 106 can be made up of epithelium tissue. The first plurality of cells 106 can be arranged in a single layer of cells, (e.g., squamous, columnar, cuboidal, or specialized) and can also be stratified or pseudostratified and arranged in layers of two or more cells deep. Apical-out 3D structure 100 can be either a monolayer or a multilayer. Epithelial cells can include, but are not limited to, mammary cells, kidney cells, lung cells, bladder cells, bronchial cells, tracheal cells, alveolar cells, corneal cells, prostate cells, renal cells, vaginal cells, cervical cells, intestine cells, or combinations thereof. In some embodiments, the first plurality of cells 106 can also have a combination of epithelium tissue as well as connective tissue, muscle tissue, and/or nervous tissue.

The first plurality of cells 106 can function similar to native epithelial cells and provide secretion, selective absorption, protection, transcellular transport, or sensing functions to the 3D structure 100. As would be appreciated, epithelium lines the inner surfaces of cavities in internal organs, similar to the typical apical-in 3D structure shown in FIG. 1A. In the apical-out 3D structure, epithelium can line the outer surface of the 3D structure 100 and imitate an inverted organ. Accordingly, an apical-out 3D structure may mimic mammary glands, kidneys, lungs, bladders, bronchial airways, tracheal airways, cornea, prostates, urethras, vaginas, cervixes, intestines, or combinations thereof. In general, E-cadherin is expressed by some epithelial cells (i.e., MCF10A and other mammary epithelial cells, lung epithelial cells, kidney epithelial cells and many other epithelial cells) and can cause regions of mainly one cell type to form. Further, E-cadherin immunostaining can be used to reveal certain epithelial cells and verify the apical-out 3D structure organization (see FIG. 14A). In the apical-out organization, the first plurality of cells 106 can interact with the external environment of the 3D structure 100. In some embodiments, the tissue layer 102 and/or the first plurality of cells 106 can include epithelial cells with apical markers making outward. As such, the cells can present certain apical cell markers and transmembrane receptor cell markers along first plurality of cells 106 and/or the second surface of tissue layer 102. As would be appreciated, apical cell markers are dependent on the type of cell. In certain embodiments, the first plurality of cells 106 can express certain apical cell markers including, but are not limited to ACE2, TMPRSS2, mucin, transporters, receptors, alpha-tubulin, acetylated alpha-tubulin, and any suitable cell markers found along or in epithelium.

In some embodiments, the first plurality of cells 106 can be made up of endothelial tissue, or single layers of squamous endothelial cells lining the interior surface of blood vessels and lymphatic vessels. Endothelial cells can include, but are not limited to primary coronary artery cells, primary pulmonary artery cells, primary aortic cells, primary dermal microvascular cells, primary umbilical vein cells, brain artery cells, brachiocephalic artery cells, internal thoracic artery cells, lymphatic endothelial cells, or combinations thereof.

In some embodiments, the apical-out 3D structure 100 can also have a second plurality of cells 108. The second plurality of cells 108 can be positioned between the tissue layer 102 and the first plurality of cells 106, as shown in FIG. 1B. In some embodiments, the second plurality of cells 108 can be positioned within the same layer as the first plurality of cells 106, as shown in FIG. 1D. Additionally, or alternatively thereto, the second plurality of cells 108 can be positioned within the interior chamber 104 of the 3D structure 100, as illustrated in FIG. 2. In some embodiments, the second plurality of cells 108 can be cultured together with the first plurality of cells 106. The second plurality of cells 108 can also be cultured independently, either before and/or after, of the first plurality of cells 106. The second plurality of cells 108 can comprise stromal cells such as connective tissue, fibroblasts, and pericytes. Stromal cells can further include, but are not limited to one or more of myoepithelial cells, adipocytes, fibrocytes, fibroblasts, myofibroblasts, pericytes, mesenchymal stem cells, macrophages, mast cells, and lymphocytes.

FIG. 1C provides an example of a conventional apical-in organoid with multiple tissue types. The inset shows a schematic of a viral infection that would take place on the apical side of an organoid. As shown, in order to introduce the virus to the apical side of an apical-in organoid, a microinjection within the organoid is necessary. A platform which can reduce the challenge of introducing viruses is shown in FIG. 1D. As illustrated, an apical-out organoid 200 can ease the loading of a virus for monitoring the progression of a viral infection from the apical side of the organoid 200. As discussed above, an apical-out organoid 200 can have a tissue layer 202 forming the interior surface of the organoid 200 and defining the interior chamber 204. Additionally, organoid 200 can have a first plurality of cells 206, a second plurality of cells 208, and a third plurality of cells 210. For instance, in a non-limiting example of a branchial airway organoid, the tissue layer 202 can comprise basal cells making up a basement membrane, the first plurality of cells 206 can comprise ciliated cells, the second plurality of cells 208 can comprise goblet cells, and the third plurality of cells can comprise club cells. In some embodiments, ciliated cells can have a first side comprising a plurality of cilia and an opposing second side. In the apical-out organoid having ciliated cells, the first side is positioned outward such that the plurality of cilia is exposed to the external environment of the organoid.

In another non-limiting example of a mammary gland organoid shown in FIG. 1E, the organoid 200 can include the tissue layer 102 basement membrane, the first plurality of cells 106 made up of epithelial cells, and the second plurality of cells 208 made up of adipocytes and/or preadipocytes.

FIG. 1E further provides a schematic of a method of forming the apical-out organoid 200 having a co-culture of tissues with the interior chamber 104 filled or partially filled with an extracellular matrix mixture 212. Extracellular matrix mixture 212 can be composed of a complex mixture of structural and functional proteins. In general, extracellular matrix mixture 212 can include macromolecules and minerals such as collagen, enzymes, glycoproteins, hydroxyapatite, bone tissue, reticular fibers, blood plasma, and combinations thereof. In some embodiments, extracellular matrix mixture 212 can function to provide support during 3D structure 100 and/or organoid 200 formulation. In addition, the extracellular matrix mixture 212 can function to segregate tissues from one another. For instance, in an apical-out organoid organization, the extracellular matrix mixture 212 can be trapped within the interior chamber 104 of the organoid 200. Further, the extracellular matrix mixture 212 can provide a wide range of cellular growth factors to the organoid 200.

FIG. 2 illustrates an example method 300 of making apical-in 3D structures 100 and organoids 200. The method includes mixing an extracellular matrix mixture 212 at a first temperature with a culture medium at a second temperature, the second temperature greater than the first temperature (step 310). Step 310 can include heating the culture medium to a temperature greater, or warmer, than the temperature of the extracellular matrix mixture. Additionally, or alternatively to, step 310 can include cooling the extracellular matrix mixture to a temperature lower than, or cooler, than the temperature of the culture medium. The culture medium temperature can range from about 20° C. to about 40° C. (e.g., from about 21° C. to about 40° C., from about 22° C. to about 40° C., from about 23° C. to about 40° C., from about 24° C. to about 40° C., from about 25° C. to about 40° C., from about 26° C. to about 40° C., from about 27° C. to about 40° C., from about 28° C. to about 40° C., from about 29° C. to about 40° C., from about 30° C. to about 40° C., from about 31° C. to about 40° C., from about 32° C. to about 40° C., from about 33° C. to about 40° C., from about 34° C. to about 40° C., from about 35° C. to about 40° C., from about 36° C. to about 40° C., from about 37° C. to about 40° C., from about 38° C. to about 40° C., from about 39° C. to about 40° C., and any additional ranges and integers not expressly stated, e.g., 27.5° C. to about 37.2°

C.). In general, a culture medium temperature greater than or equal to room temperature is preferred. As would be appreciated by those of skill in the relevant art, protocols for formation of apical-in organoids require mixing extracellular matrix mixtures with a chilled culture medium, or a culture medium at a temperature lower than the extracellular matrix mixture and at higher extracellular matrix concentrations. In contrast, formation of apical-out organoids require mixing extracellular matrix mixtures with a warmed culture medium, or a culture medium at a temperature higher than the extracellular matrix mixture and at lower extracellular matrix concentrations that is typical as described in manufacturer instructions. More generally, an extracellular matrix mixture is added to warm medium in small amounts where the conventional method would simply dilute the mixture and preclude gel formation. In the method 300 disclosed herein, the small amount of extracellular matrix mixture is added to medium at a temperature above a lower critical solution temperature of the extracellular matrix mixture. A lower critical solution temperature is a critical temperature at which the components of a mixture are miscible for all compositions, or not gelled.

In some embodiments, prior to mixing the extracellular matrix mixture, a stock solution of extracellular matrix mixture can be prepared. Highly concentrated extracellular matrix mixtures may form a gel-like consistency at concentrations above conventional recommended concentrations. For instance, a concentration above 3 mg/mL of extracellular matrix mixture may result in gelling. In certain embodiments, extracellular matrix mixture may gel and form a minimal scaffold in which the apical-out 3D structure and/or organoid can be formulated. In some embodiments, a concentration of extracellular matrix mixture above about 4 mg/mL may be used to form the apical-out organoid (e.g., above about 4.5 mg/mL, above about 5 mg/mL, above about 5.5 mg/mL, above about 6 mg/mL, above about 6.5 mg/mL, above about 7 mg/mL, above about 7.5 mg/mL, above about 8 mg/mL, above about 8.5 mg/mL, above about 9 mg/mL, above about 9.5 mg/mL, above about 10 mg/mL, above about 10.5 mg/mL, above about 11 mg/mL, above about 11.5 mg/mL, above about 12 mg/mL, and any additional concentration ranges and integers of such not expressly stated, e.g., from about 7.4 mg/mL to about 10.7 mg/mL).

In some embodiments, step 310 can include mixing less than 1 mg/mL of the extracellular matrix mixture with the culture medium to form the concentrations described above and promote gelling (e.g., less than 0.95 mg/mL, less than 0.90 mg/mL, less than 0.85 mg/mL, less than 0.80 mg/mL, less than 0.75 mg/mL, less than 0.70 mg/mL, less than 0.65 mg/mL, less than 0.60 mg/mL, less than 0.55 mg/mL, less than 0.50 mg/mL, less than 0.45 mg/mL, less than 0.40 mg/mL, less than 0.35 mg/mL, less than 0.30 mg/mL, less than 0.25 mg/mL, less than 0.20 mg/mL, less than 0.15 mg/mL, less than 0.10 mg/mL, less than 0.08 pg/mL, less than 0.06 mg/mL, less than 0.04 mg/mL, less than 0.02 mg/mL, less than 0.01 mg/mL, and any additional range and integers of such not expressly stated, e.g., less than 0.68 mg/mL). Additionally, or alternatively thereto, step 310 can include mixing less than 500 μg/mL of the extracellular matrix mixture with the culture medium (e.g., less than 480 μg/mL, less than 440 μg/mL, less than 400 μg/mL, less than 360 μg/mL, less than 320 μg/mL, less than 280 μg/mL, less than 240 μg/mL, less than 200 μg/mL, less than 160 μg/mL, less than 120 μg/mL, less than 90 μg/mL, less than 80 μg/mL, less than 70 μg/mL, less than 60 μg/mL, less than 50 μg/mL, less than 40 μg/mL, less than 30 μg/mL, less than 20

μg/mL, less than 10 μg/mL, and any additional range and integers of such not expressly stated, e.g., less than 452 μg/mL).

In some embodiments, adding too much or too little of the extracellular matrix can preclude formation of one large apical-out organoid. For instance, adding too much extracellular matrix can result in multiple small apical-in organoids. Alternatively, adding too little extracellular matrix can form small, dense cells, not organoids. Generally, the total volume of gel formed is similar to the size of organoid to be formed.

Once at least the extracellular matrix mixture is mixed with a culture medium, the method can include culturing a first plurality of cells in the extracellular matrix mixture and culture medium (step 320). Step 320 can include culturing the first plurality of cells and the extracellular matrix mixture and culture medium in a non-stick surface culture system, such as, for example, one or more of a hanging drop system, an ultra-low attachment system, a hydrogel well system, an ultrasound levitation system, or any suitable research and industrialized methods used for making 3D structures or organoids. In some embodiments, step 320 can further include culturing a second plurality of cells simultaneously with culturing the first plurality of cells. Additionally or alternatively thereto, step 320 can include culturing the second or third plurality of cells after culturing the first plurality of cells.

The method 300 can further include forming a 3D structure having an interior chamber enclosed by the first plurality of cells configured to interface with an environment external to the 3D structure (step 330). Step 330 can further include entrapping the extracellular matrix mixture within the interior chamber of the 3D structure. In some embodiments, step 330 can also include forming a tissue layer between the first plurality of cells and the interior chamber of the 3D structure. It should be appreciated that the tissue layer can be produced by the first plurality of cells. In general, basement membrane components are usually not present in a significant amounts in extracellular matrix media used for culturing organoids. As would be appreciated by those of skill in the art, some organoid structures may mimic complex organs and form additional 3D structures within the internal chamber of the apical-out 3D structure. Additionally, or alternatively thereto, the apical-out 3D structure may have folds or crypt-like domains such that only a portion of the first plurality of cells is interfacing with the environment external to the 3D structure. In some embodiments, forming the apical-out 3D structure of method 300 can result in from about 5% to about 100% of the first plurality of cells interfacing with the environment external to the 3D structure. (e.g., from about 5% to about 100%, from about 10% to about 100%, from about 15% to about 100%, from about 20% to about 100%, from about 25% to about 100%, from about 30% to about 100%, from about 35% to about 100%, from about 40% to about 100%, from about 45% to about 100%, from about 50% to about 100%, from about 55% to about 100%, from about 60% to about 100%, from about 65% to about 100%, from about 70% to about 100%, from about 75% to about 100%, from about 80% to about 100%, from about 85% to about 100%, from about 90% to about 100%, from about 95% to about 100%, from about 96% to about 100%, from about 97% to about 100%, from about 98% to about 100%, from about 99% to about 100%, from about 99.5% to about 100%, from about 99.9% to about 100%, from about 99.99% to about 100%, and any additional range and integers of such not expressly stated, e.g., about 84.25%).

The method 300 can further include exposing the environment external to the apical-out 3D structure to a virus, a bacteria, a fungi, a cancer cell, an immune cell, a stem cell, a drug, or combinations thereof. As would be appreciated, exposing epithelial cells positioned on the external surface of an apical-out 3D structure can be done by adding the virus, bacteria, fungus, cancer cell, immune cell, stem cell, or drug to the environment (e.g., medium, scaffold, or other) in which the 3D structure is in.

In addition, method 300 can alter gene expression in cells within an apical-out 3D structure relative to the same cells cultured in conventional culture dishes in 2D. For instance, an apical-out bronchial epithelial cell organoid formed by method 300 may result in an up-regulation of certain genes relative to the same bronchial epithelial cells cultured in the conventional way (e.g., FN1, COL1A2, MMP9, CHI3L1, LTF, ANPEP, VCAN, COL1A1, CORO6, SLCO2A1, PI3, COL6A1, CYP1A1, PGGHG, COL4A4, IL34, SULT1B1, CSPG4, GPNMB, RIPOR3, ATP10B, MUC16, SLC26A4, SERPING1, CASC15, RSPH4A, VNN3, SPNS2, ATP10A, MCF2L, B3GALT5, DNAI1, ATP2A3, MMP3, BMF, TAGLN, GSN-AS1, FOXJ1, LINC02015, SLC25A25-AS1, C12orf74, TPPP3, COL9A2, SLC15A1, CAPN13, CHL1, ALOX5, POU2F2, KMO, NID1, CFTR, CFAP221, SRGAP3-AS2, ACHE, INPP5J, LINC00894, NFATC4, MYH14, VIM, MTRNR2L10, ATG9B, CUX2, PNLIPRP3, FCGBP, CCDC78, SHC2, TRO, COL4A3, VWA3B, CARD9, TENM2, ATF3, TTC25, UCKL1-AS1, CCDC17, RGL4, SORCS2, HLA-DRA, FAM20A, NEAT1, KRT75, PCDHA11, RP1, ZBTB46, CCDC146, CPNE4, KCNIP3, MUC4, ZMYND10, NEK10, DTHD1, LRRC10B, PLEKHS1, MT-ND5, CFAP157, NPTXR, CYP1B1, C1S, BVES, HLA-DRB1). In the same example, an apical-out bronchial epithelial cell may also result in a down-regulation of certain genes (e.g., UBE2C, CDKN3, CEP55, MYBL2, PBK, RRM2, KIF4A, BIRC5, HJURP, ANXA10, CENPA, HAS2, CALB2, SPC24, AURKB, GINS2, CA9, CDC45, MKI67, CKAP2L, HMMR, SHCBP1, CDC25C, DLGAP5, NCAPG, NDC80, STC1, NUSAP1, NEIL3, DEPDC1, CDC20, KIF20A, SPC25, CCNA2, PRSS3, LINC02742, TOP2A, TK1, ESCO2, ASF1B, NCAPH, BUB1, BUB1B, CLSPN, CDCA7, IGFBP6, NUF2, CDCA2, PCLAF, GTSE1, BMP7, KIF14, CCNB2, CDK1, EXO1, IL1RL1, CEMIP, FAM72A, SGO1, KNL1, SKA1, PIMREG, LMNB1, FAM72B, SNX31, OIP5, CDC6, TPX2, MND1, CENPM, AL732437.2, ABCG2, LNCAROD, ASPM, CCNB1, SKA3, CCNE2, CNTN1, AKR1B10, FAM72C, PRR11, HIST1H1A, PSRC1, SCAT8, DEPDC1B, TTK, MAD2L1, KIF15, TROAP, ARHGAP11A, POLE2, NR5A2, RAD54L, RAD51AP1, ANLN, KIF18A, NDUFA4L2, PALD1, PTTG1, KIF2C). As would be appreciated, gene expression in cells of an apical-out 3D structure may be more readily accessible compared to cells cultured in conventional culture dishes in 2D. Method 300 may be useful in assessing gene expression for a variety of epithelial cell organoids.

The following examples further illustrate aspects of the present disclosure. However, they are in no way a limitation of the teachings or disclosure of the present disclosure as set forth herein.

EXAMPLES

Example 1: A Minimal Gel Scaffold Is Key for MCF10A Organoid Formation

A cellular self-assembly of unusually large mammary organoids in a hanging drop culture platform was designed.

Figure 5A:
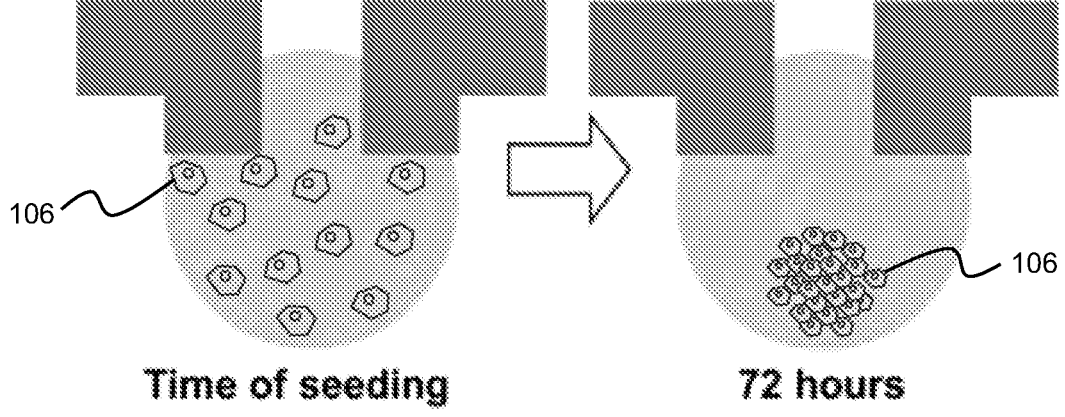
FIG. 5A shows a schematic representation of conventional spheroid formation with no Matrigel added to media.
Figure 5B:
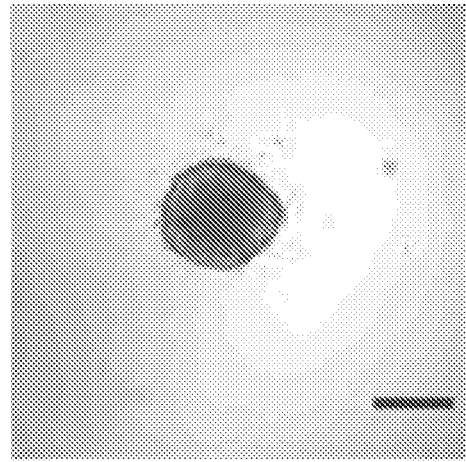
FIG. 5B provides a brightfield image of no Matrigel added to media for conventional spheroid formation.
Figure 6A:
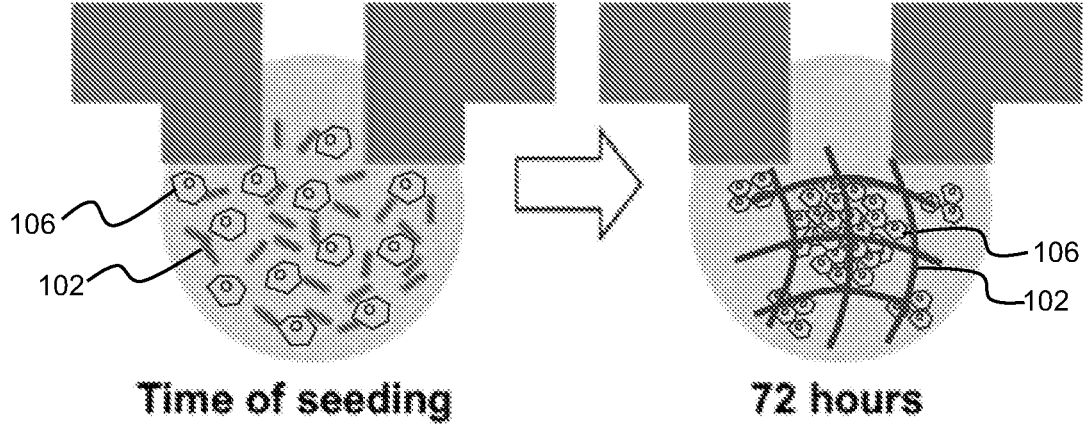
FIG. 6A shows a schematic representation of cell-assisted minimal scaffolding with $120\pm10$ µg/mL Matrigel added to cold media where organoid formation is sub-optimal.
Figure 6B:
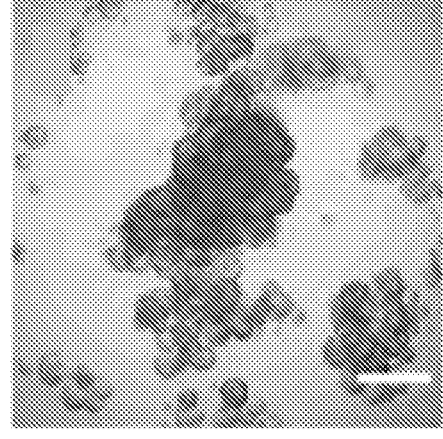
FIG. 6B provides a brightfield image of $120\pm10$ µg/mL Matrigel added to cold media where organoid formation is sub-optimal.

To better characterize the role of Matrigel from a materials perspective, the gels that form under the experimental conditions described herein in the absence of cells were analysed. It is noted that although Matrigel is known to form gels upon warming, the manufacturer's recommended concentration is 3 mg/mL and above, whereas the concentration used in the protocol described herein is around 100 µg/mL, a concentration where gel formation is usually not expected. Indeed, when the conventional protocol of mixing all media components (including Matrigel) at low temperature and then warming the media is followed, gelling does not occur, as shown in FIGS. 3A through 3D. Gelling is minimal even when the Matrigel stock solution is directly added to pre-warmed media if fetal bovine serum (FBS) is absent. Interestingly, in the protocol described herein, where the concentrated Matrigel stock solution is added to pre-warmed media that also includes a high serum concentration, a gel-like substance develops. This gel-like substance is, initially, homogenously spread throughout the hanging drop (FIGS. 3A-3D). When MCF10A cells are present, the cells consolidate this gel-like substance (FIGS. 4A through 4C), as can be seen in FIG. 4B where the arrow is pointing to the edge of the more localized clear gel. Cell-assisted organization of a minimal Matrigel scaffold is evident when comparing the differences in gel organization with and without the addition of cells. Upon further incubation, the cells fully entrap the gel in the core of a 3D structure and are suggested to undergo coordinated rotational movement in order to maintain apicobasal polarity. It was found that the amount of Matrigel is important as both too little and too much Matrigel precludes formation of one large organoid in each drop. As shown in FIGS. 5A and 5B, if no Matrigel is included in the culture, then the MCF10A 3D cultures form simple compacted spheroids instead of the much larger, hollow organotypic structures of interest. Conversely, if too much Matrigel is included, the MCF10A cells form many small acinar structures, but never merge into one organoid. As shown in FIGS. 6A and 6B, even when the Matrigel concentration is appropriate for forming the inverted organoid (120±10 µg/mL), if the media components are mixed when cold, following the manufacturer recommended protocol, the MCF10A cells form multiple small clumps, and often never completely merge into an organotypic structure. Taken together, it is critical to add cold Matrigel to warm media with FBS to allow for pre-gelling, and the Matrigel concentration has been optimized to 120±10 µg/mL.

Example 2: The MCF10A Organoids have a Basal-In Phenotype

The Matrigel in the organoid core was further characterized at later timepoints. Using histological organoid sections as previously reported, hematoxylin and eosin (H&E) staining revealed a network with pink hues inside of the organoid, suggesting presence of extracellular matrix proteins (ECM), shown in FIG. 7A. FIG. 7B shows a pan laminin-1,2 immunostaining, which also showed extensive staining consistent with the notion that Matrigel (Corning, #356231), which is approximately 60% laminin (largely laminin-1), was encapsulated.

Laminin-5 has been used extensively as an indicator of the basement membrane for MCF10A cells grown in 3D culture, as it is known to be produced by the cells but is not present in significant amounts in Matrigel. With MCF10A acini formed in conventional gel scaffolds or overlay systems, the laminin-5 stains show a basal-out phenotype with the basement membrane on the outside of the small acinar structures (FIG. 1A). Upon examination of laminin-5 staining of the organoids made using the methods described herein, however, the basement membrane was surprisingly found to be on the interior surface of the organoid structure (FIG. 1B). That is, at the outer periphery of the organoids, the distinct layer of laminin-5 (red) is on the inner side of the MCF10A cell nuclei (blue) (FIG. 8A). The organoids were further assessed through integrin alpha-6 staining because of the integrin alpha-6's established role in basement membrane adhesion. Like the laminin-5 staining, the integrin alpha-6 was focused on the inner periphery of the organoid section, further supporting a basal-in cellular phenotype of these mammary organoids (FIG. 8B).

The basement membrane organization of the acinar structures found within the interior of many organoids was also analyzed. These smaller structures mostly maintain their basement membrane layer on the outside of the acini (FIG. 8C), indicative of the more common basal-out polarity. Overall, Matrigel appears to play a critical role in the development of a basal-in phenotype. When it becomes entrapped inside of the organoid, the cells form around a Matrigel core (FIGS. 1B, 4A-C). In turn, the organoid senses the basement membrane signal on the inside and the cells produce their own basement membrane, allowing for generation of the basal-in phenotype organoid structures. On the other hand, the small acini in the organoid interior result in a basal-out polarity with an exterior basement membrane due to having Matrigel contact from the outside. These laminin-5 and integrin alpha-6 staining results reveal the intricacy of epithelial polarity within the organoid not described in prior publications with only cytokeratin 5/6 (CK 5/6) and cytokeratin 18 (CK 18) staining. It is contemplated that the basal-in phenotype is more complex than initially described.

The stable basal-in phenotype and prominent basement membrane observed by the large organoids constructed by the methods described herein, stand in contrast to other reports of the smaller-sized, so-called inverted organoids where there is lack of characterization or presence of a stable basement membrane. These smaller inverted organoids often show a mixture of inversion and non-inversion in the same organoid as revealed by various apical and basolateral markers, and the polarity flips back and forth between normal and inverted states quite readily.

Example 3: MCF10A Cells Form Organoids with a Basal-In Phenotype Even When Co-Cultured with MDA-MB-231 Cells from Day 0

Co-culture organization into different 3D structures under different culture conditions was explored using MCF10A and MDA-MB-231 cells. Co-cultures of 3000 MCF10A and 300 MDA-MB-231 cells were performed in both the absence and presence of the minimal Matrigel scaffold at the time of seeding. It is noted that after the initial seeding, media exchange was performed with media that does not contain any Matrigel for all culture conditions tested. Organoids were tracked and imaged every few days for the 16-day growth period.

3D cultures without the minimal Matrigel scaffold resulted in a distinct separation between the two cell populations (FIG. 9A). The MCF10A cells formed a small compact spheroid, and the fluorescent MDA-MB-231 cells grew in loosely packed groups of cells surrounding the MCF10A spheroid at random locations. These observations are similar to previously published co-cultures of MCF10A and MBA-MD-231 cells.

Figure 10:
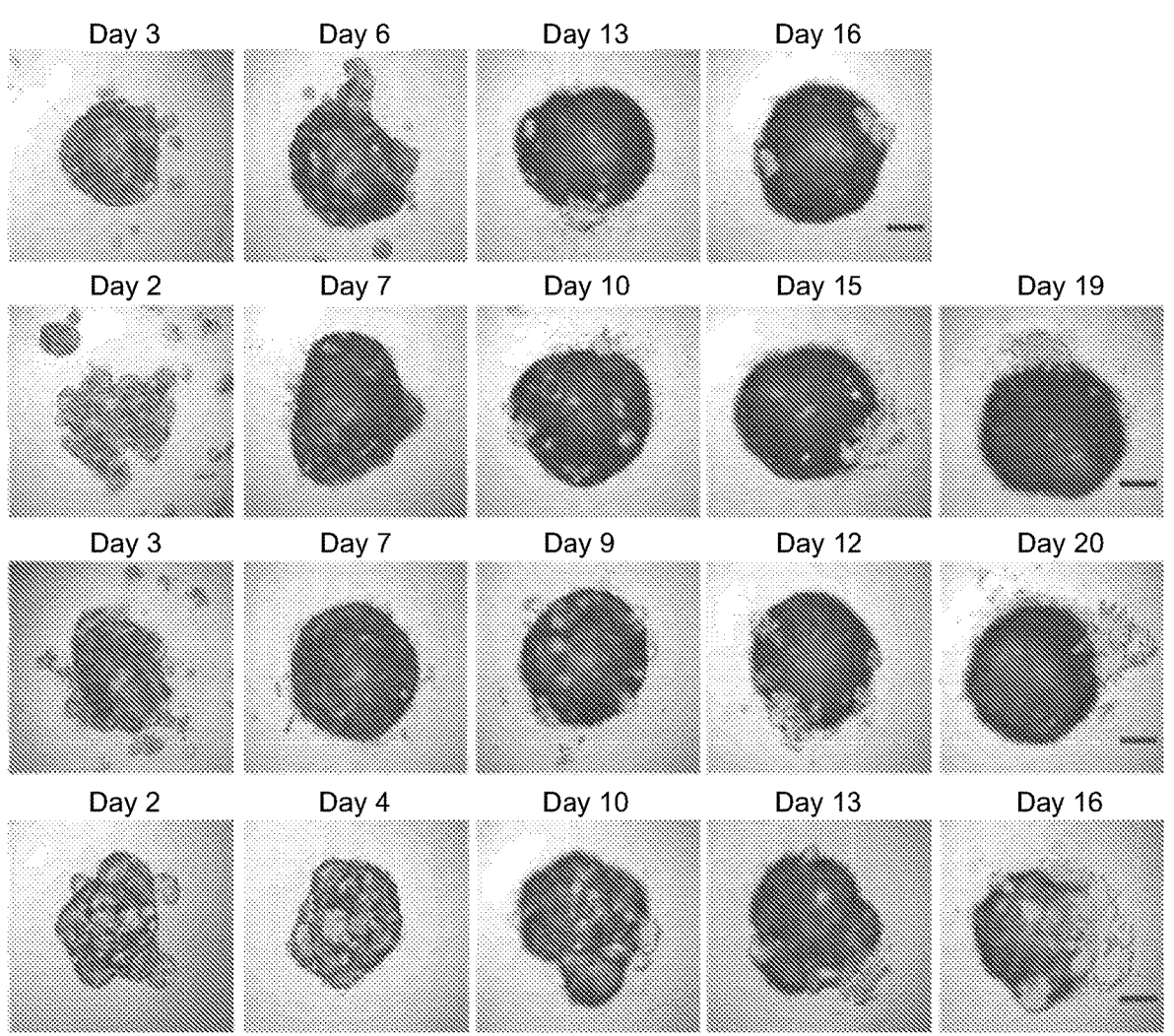
FIG. 10 provides self-organizing behaviors of four independent experiments showing epithelial cells and cancer cells co-culture and time course development with $120\pm10$ µg/mL Matrigel, in accordance with an exemplary embodiment of the present disclosure.
Figures 11A, 11B:
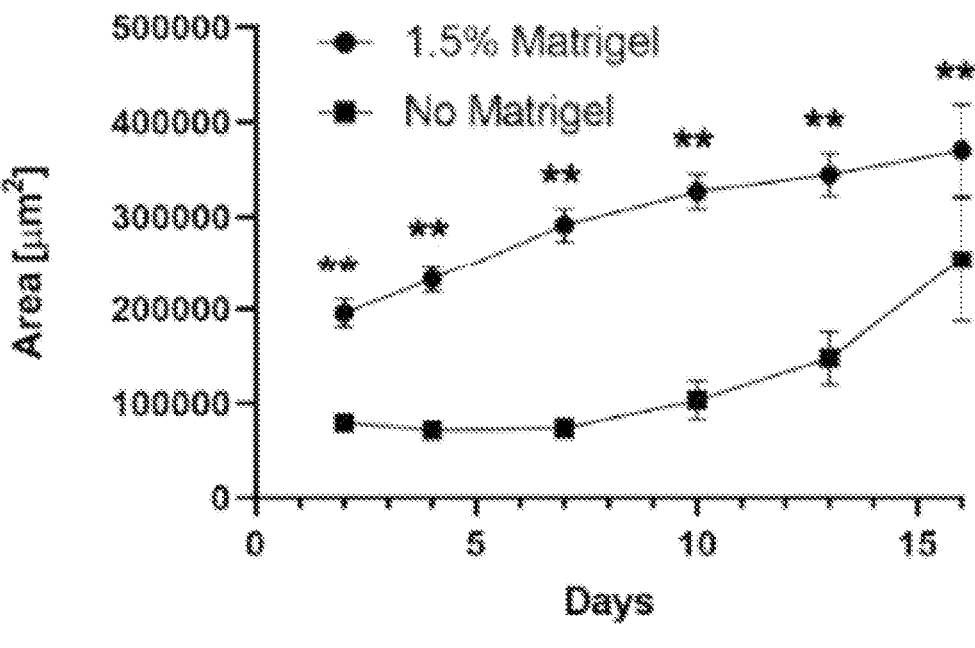
FIG. 11A shows plots of area ($\mu m^2$) versus days for co-culture both with and without Matrigel, in accordance with an exemplary embodiment of the present disclosure.
FIG. 11B shows plots of roundness versus days for co-culture both with and without Matrigel, in accordance with an exemplary embodiment of the present disclosure.

Conversely, as shown in FIG. 9B, co-cultures with the minimal Matrigel scaffold exhibited a significantly different morphology. At day 2, there was a relatively well-mixed distribution of the two cell populations, although the overall size of the cellular structure was already significantly larger than co-cultures without Matrigel (p-value <0.000001). At later time points, the MDA-MB-231 cells organized into distinct patterns with one sub-population confined to the organoid interior, and another sub-population forming peripheral spheroids (indicated with a black arrow in FIG. 9B at day 16). This 3D organization of MCF10A and MDA-MB-231 cells is robust and was reproduced among multiple independent co-culture experiments (FIG. 10). In terms of morphology, the organoids seeded with Matrigel grew significantly larger compared to those seeded without Matrigel, although the discrepancy in area decreased over time in the culture. By day 16, the overall sizes were less different due to more extensive growth of the MDA-MB-231 cells in the condition without Matrigel (FIG. 11A). In terms of roundness (FIG. 11B), organoids without Matrigel experienced a statistically significant drop in roundness between days 7 and 10, largely because of the rapid growth of MDA-MB-231 cells at random peripheral positions. This also accounts for the higher standard deviations between different organoids for some days shown in FIG. 11A and FIG. 11B. For organoids with Matrigel, the roundness stayed consistent throughout the culture; the small decrease is due to growth of small peripheral spheroids of MDA-MB-231 cells adjacent to the main organoid body. These differences between the two cell seeding conditions underline the importance of a minimal Matrigel scaffold at the time of seeding for producing the outside-in breast cancer organoids.

Figure 12A:
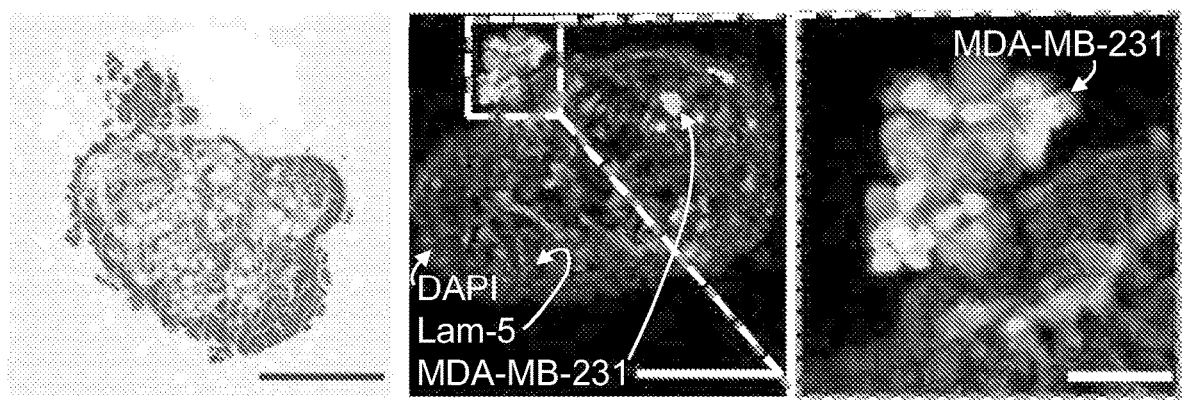
FIG. 12A provides images showing H&E stain (left) and laminin-5 stain (right) of a day 16 co-culture organoid where a peripheral cancer cell ball remained attached to the main organoid body, in accordance with an exemplary embodiment of the present disclosure.
Figure 12B:
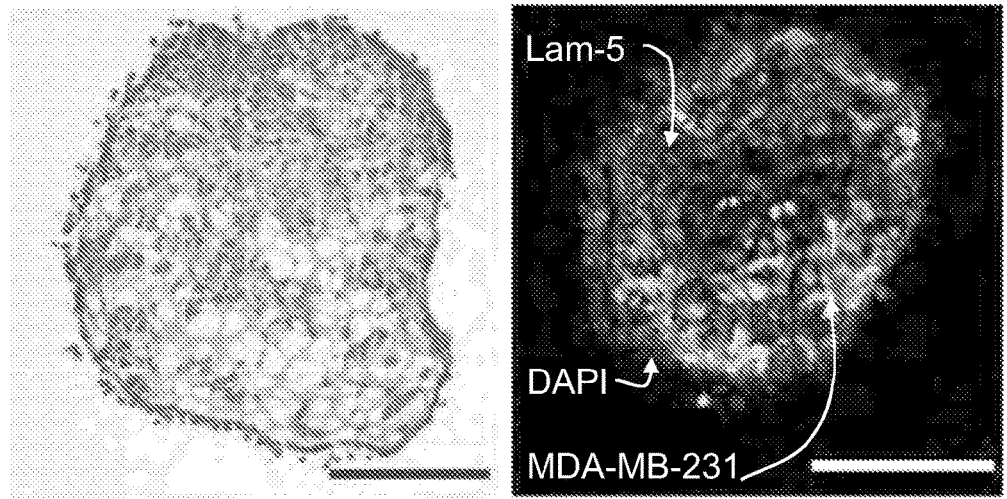
FIG. 12B provides images showing H&E stain (left) and laminin-5 stain (right) of a day 16 co-culture organoid where a peripheral cancer cells dissociated from the organoid, which represents a majority of the co-culture organoids, in accordance with an exemplary embodiment of the present disclosure.

As seen in FIG. 9B, the co-culture organoids often have a loosely attached peripheral spheroid of MDA-MB-231 cells adjacent to the main organoid structure while they are maintained in hanging drop culture. However, through harvesting and gentle pipetting, the peripheral spheroid is dissociated from the main body in a majority of the co-culture organoids. FIG. 12A further shows H&E and laminin-5 images for one example where the peripheral spheroid remains attached to the organoid, and an example where the peripheral spheroid dissociated upon gentle pipetting (FIG. 12B). In both cases, the organoid maintained a basal-in phenotype, as can be seen by laminin-5 predominantly localized on the inner side of the organoid epithelium. For the condition where the peripheral spheroid remained attached to the main organoid body, a microinvasion point with disorganization of the basement membrane is visible, reminiscent of initial stages of breast carcinoma in situ.

Overall, a robust and reproducible method for the long-term maintenance (20+ days) of co-cultures where the MCF10A cells show a basal-in phenotype is demonstrated.

MCF10A and MDA-MB-231 cells have been co-cultured previously, including in a 3D format as described by Carey et al. (S. P. Carey, A. Starchenko, A. L. McGregor, C. A. Reinhart-King, Clin. Exp. Metastasis 2013, 30, 615). The experiments from Carey et al., resulted in cell-filled spheroids with a core of MDA-MB-231 cells, followed by layers of MCF10A cells, and additional MDA-MB-231 cells on the periphery. The 3D co-cultures generated by the methods described herein also formed structures with MDA-MB-231 in the core and in the periphery but within a much larger hollow organoid structure where the MCF10A cells form a thin epithelial shell with a distinct basement membrane.

Figures 13A, 13B:
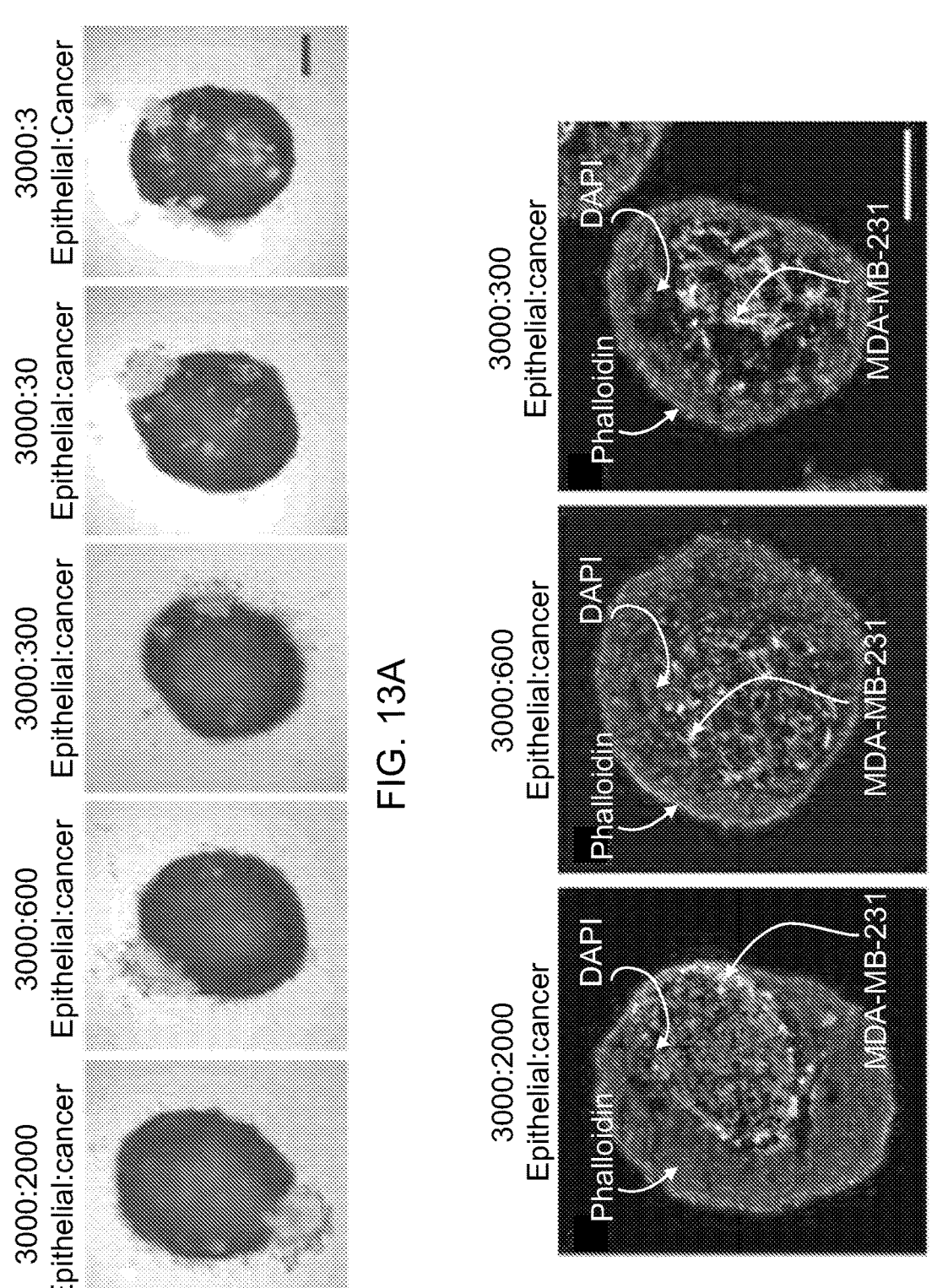
FIG. 13A provides images of day 16 co-culture organoids with different epithelial cell to cancer cell ratios from 1:1 to 1000:1, in accordance with an exemplary embodiment of the present disclosure.
FIG. 13B provides images of cryosectioning and phalloidin staining of day 16 co-culture organoids with different epithelial cell to cancer cell ratios from 1:1 to 1000:1, in accordance with an exemplary embodiment of the present disclosure.

At first glance, the two culture conditions are very similar, not only using the same cell types but also the same media, incorporation of Matrigel, and 3D culture. But the key difference leading to drastically different cellular organization outcomes was explored by multiple experiments. As shown in FIGS. 13A and 13B, testing different MCF10A: MDA-MB-231 cell ratios from 1:1 to 1000:1, the cell ratio as a major factor was excluded. The key difference is in whether the cell seeding conditions allow for minimal Matrigel scaffolding or not. Carey et al. performed cell seeding with media that only contains Methocel. The seeding media did not include Matrigel or 10% FBS, although Matrigel was introduced with the spheroid growth media following centrifugation and 2 hours of incubation. This is a condition that would not allow for cell-assisted Matrigel scaffolding as described in FIGS. 4A-4D.

Figure 14A:
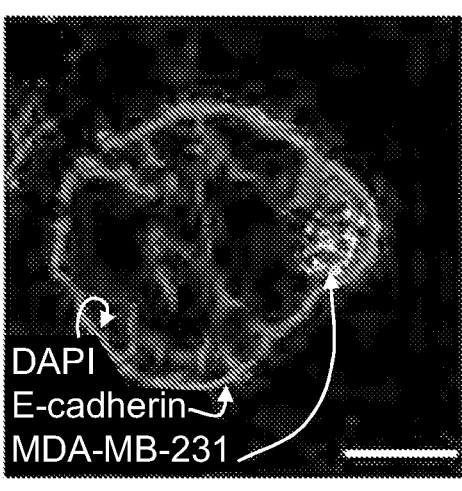
FIG. 14A shows an image of E-cadherin staining of MCF10A organoids after MDA-MB-231 cells invaded inside, in accordance with an exemplary embodiment of the present disclosure.

For both experimental platforms, there are clear self-organizing behaviors likely due to cadherin mediated cell adhesion. E-cadherin is expressed by the MCF10A cells and not the mesenchymal-like MDA-MB-231 cells, causing regions of mainly one cell type to form (FIG. 14A). The organoids disclosed herein follow similar, but slightly more distinct organization patterns, likely due to the initial Matrigel scaffolding and differences in time spent in culture. Carey et al. grew the spheroids for 48 hours and performed invasion experiments for 48 hours but did not assess long-term viability. The organoids made using the present disclosure grew as 3D co-cultures for 16-20 days, allowing more time for growth of the overall structure and yielding larger cultures, in addition to more distinct cell separation. Carey et al. noted the presence of MDA-MB-231 cells at the periphery and core. In the organoids of the present disclosure, the MDA-MB-231 cells are initially seen at the periphery and core; however, while the cancerous core remains intact, the cells assemble and form a small ball adjacent to the main structure.

Example 4: MCF10A Organoids as a Model to Study Ductal Carcinoma In Situ

Figure 14B:
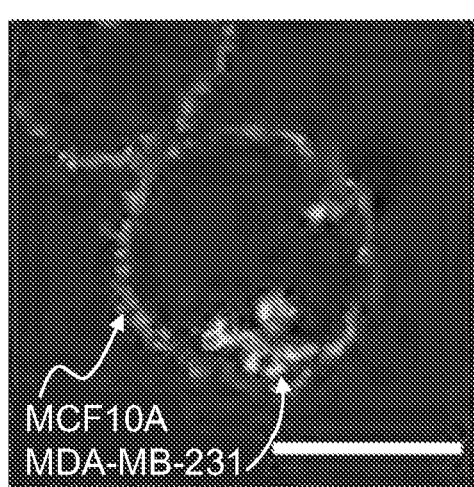
FIG. 14B shows an image of an organoid showing MDA-MB-231 cancer invasion introduced at day 7 and maintained for 9 additional days, in accordance with an exemplary embodiment of the present disclosure.
Figure 15:
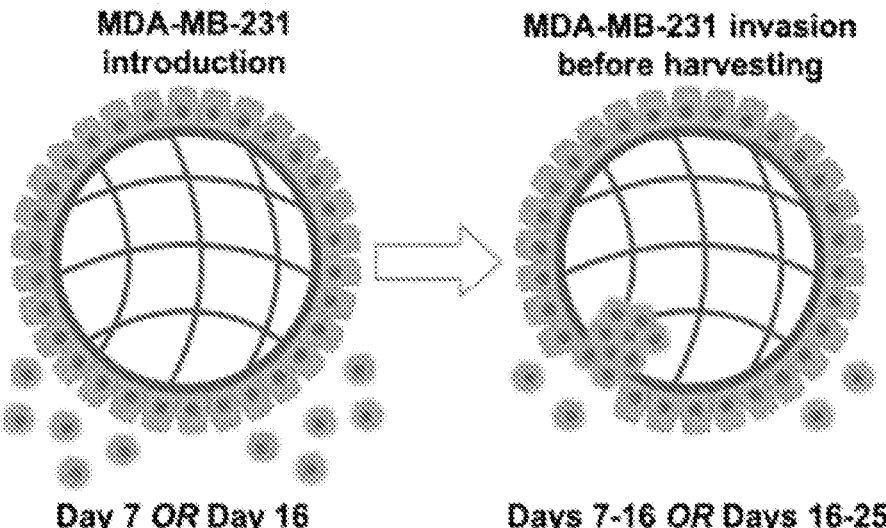
FIG. 15 provides a schematic of cancer invasion experiments, in accordance with an exemplary embodiment of the present disclosure.
Figure 16:
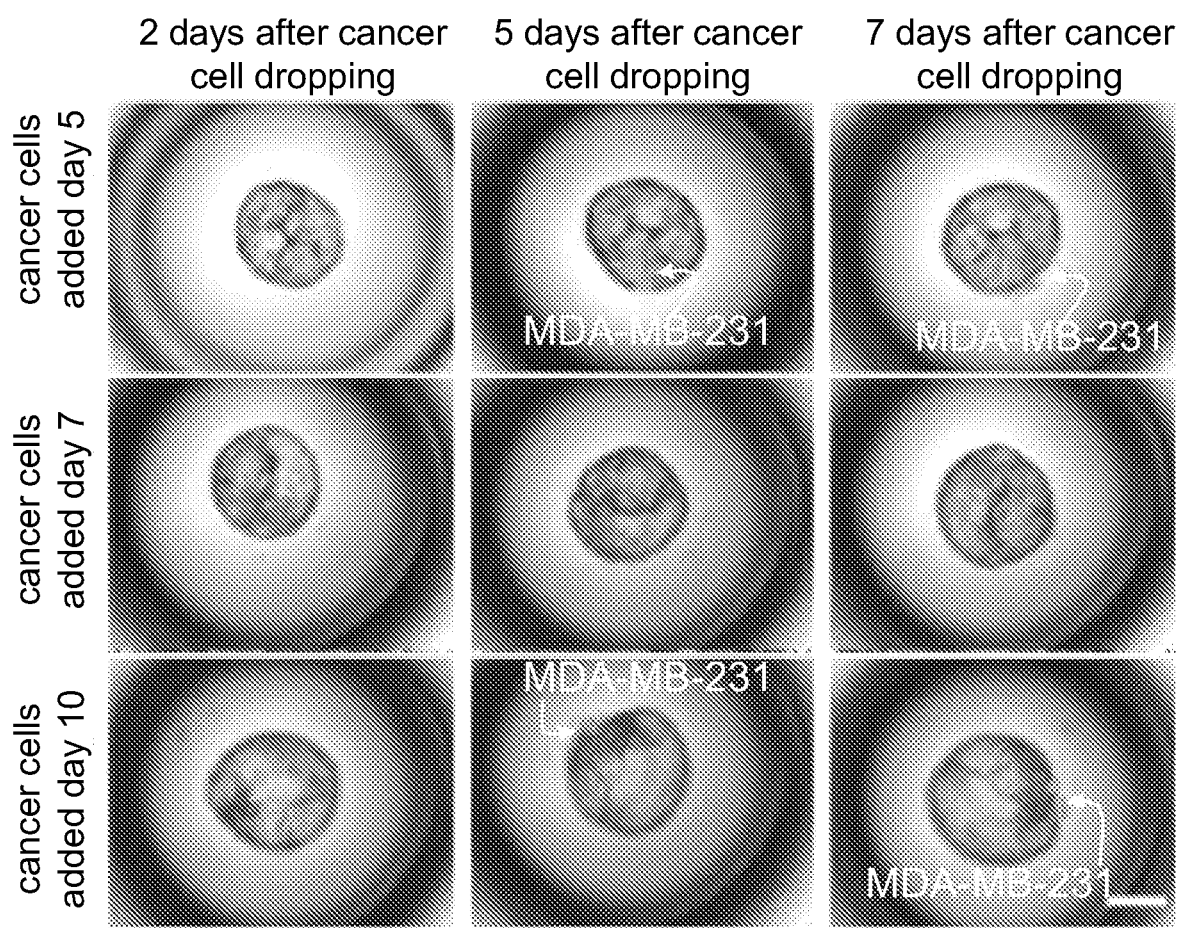
FIG. 16 shows brightfield images of invasion of MDA-MB-231 cancer cells into MCF10A organoids over time, in accordance with an exemplary embodiment of the present disclosure.
Figure 17:
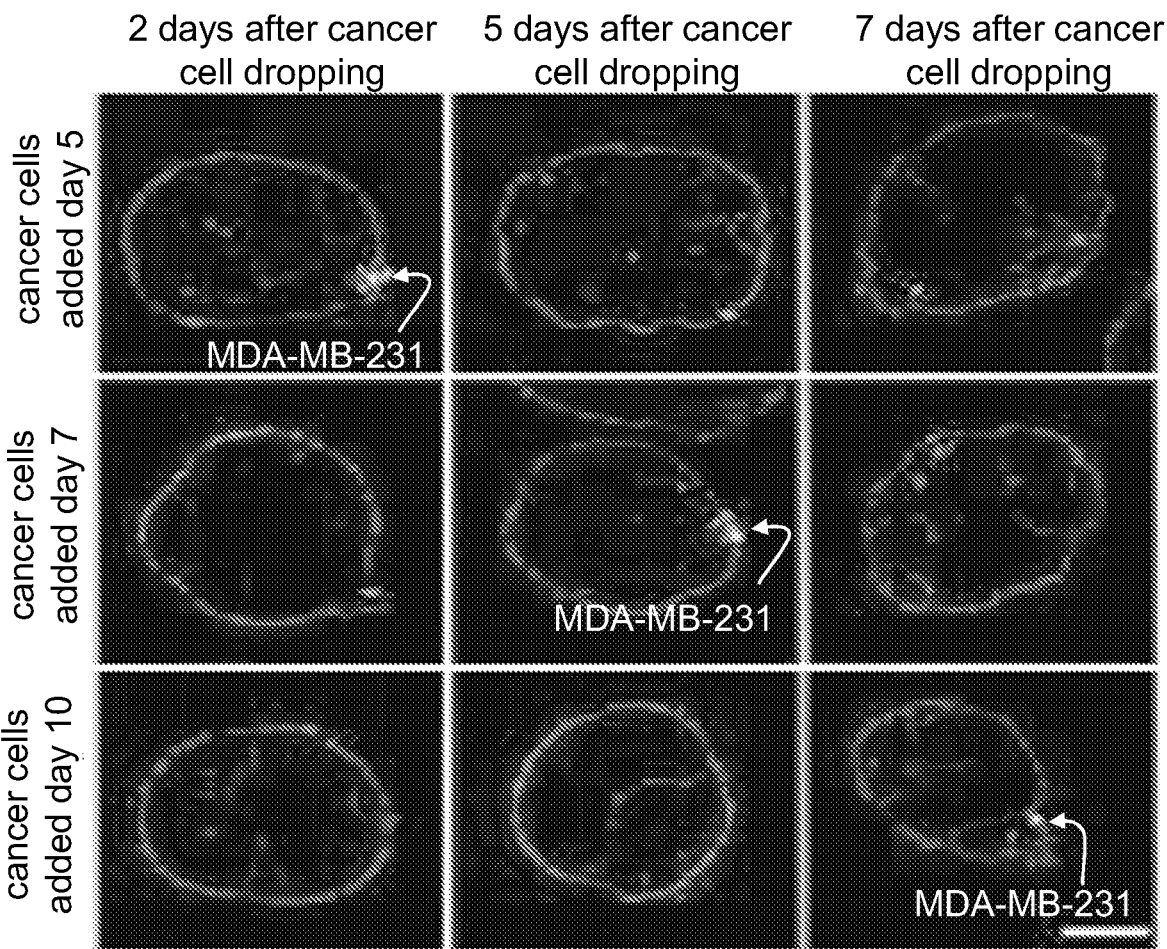
FIG. 17 shows images of E-cadherin staining of invasion of MDA-MB-231 cancer cells into MCF10A organoids over time, in accordance with an exemplary embodiment of the present disclosure.
Figure 18:
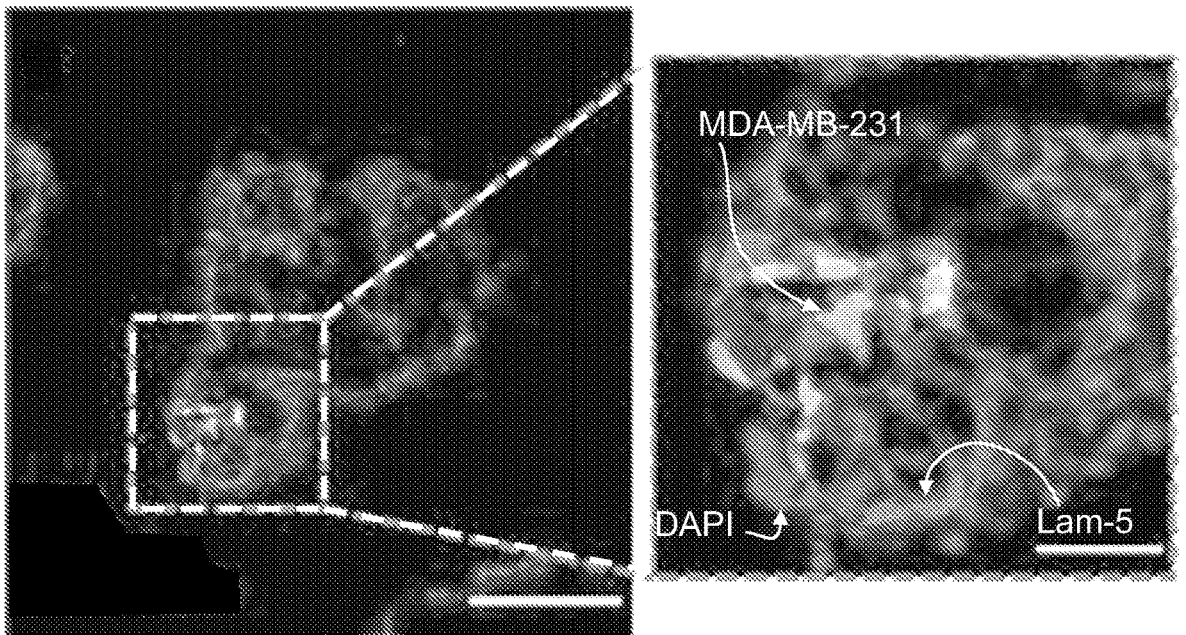
FIG. 18 shows an image of Laminin-5 staining after invasion of MDA-MB-231 cancer cells into MCF10A organoids, in accordance with an exemplary embodiment of the present disclosure.

One main advantage of the basal-in phenotype of the MCF10A organoids is direct access to the epithelial surface opposite the basement membrane, as the region in the media surrounding the organoid now represents the "luminal" side. In many previous organoid models, access to the lumen is challenging, as time-consuming and technically demanding techniques, such as microinjection, are typically required. To capitalize on this ease of "luminal" access in the organoid model described herein, the MCF10A organoids were grown to partial maturity (7 days) and exposed to 300 MDA-MB-231 cells in the media surrounding the organoid. The cancer cells were allowed to invade for 7-9 days before harvesting, fixing, and cryosectioning (FIG. 14B). Analysis revealed that the organoids generally maintain their epithelial integrity, as indicated by E-cadherin immunostaining (FIG. 14A and FIGS. 16-18). However, laminin-5 staining revealed disorganization of the basement membrane, as GFP labeled MDA-MB-231 cells could be observed inside a portion of the organoid sections that were analyzed (FIGS. 16-18).

Figure 19:
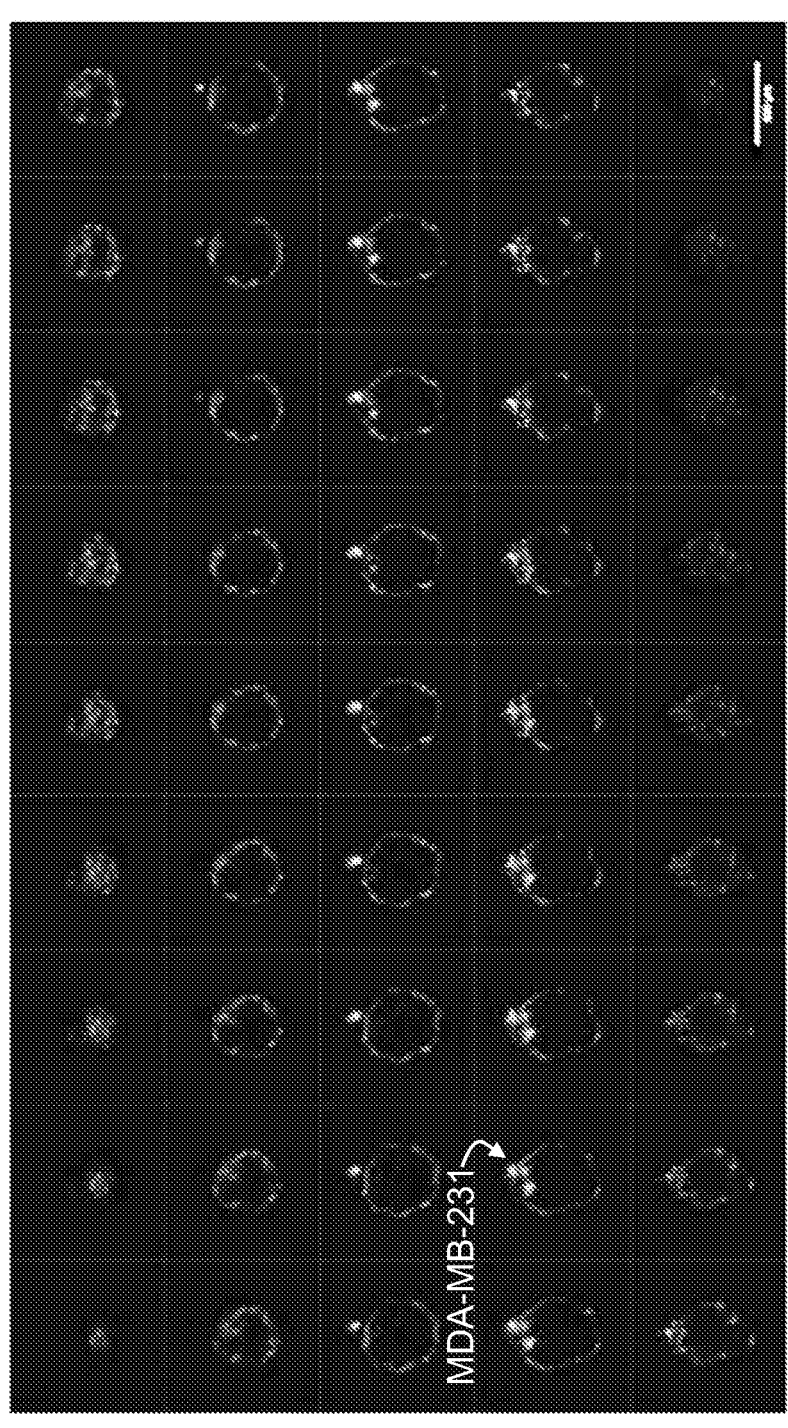
FIG. 19 shows images of MCF10A organoids (confocal microscope sections) over time with exposure to MDA-MB-231 cancer cells on day 7 of the organoid culture, in accordance with an exemplary embodiment of the present disclosure.
Figure 22:
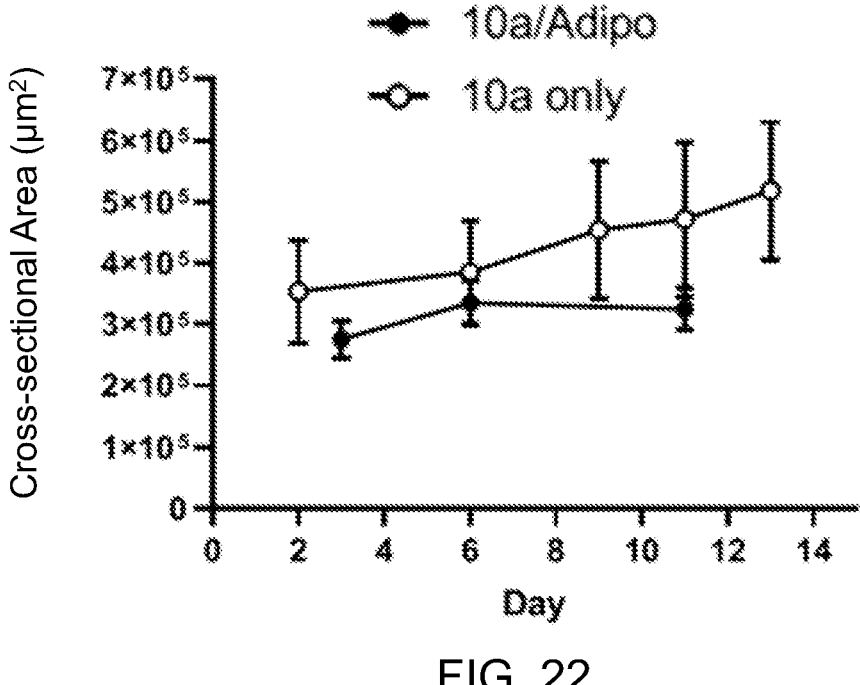
FIG. 22 shows a plot of cross-sectional area ($\mu m^2$) for organoids with co-culture and without co-culture over time (days), in accordance with an exemplary embodiment of the present disclosure.
Figure 23:
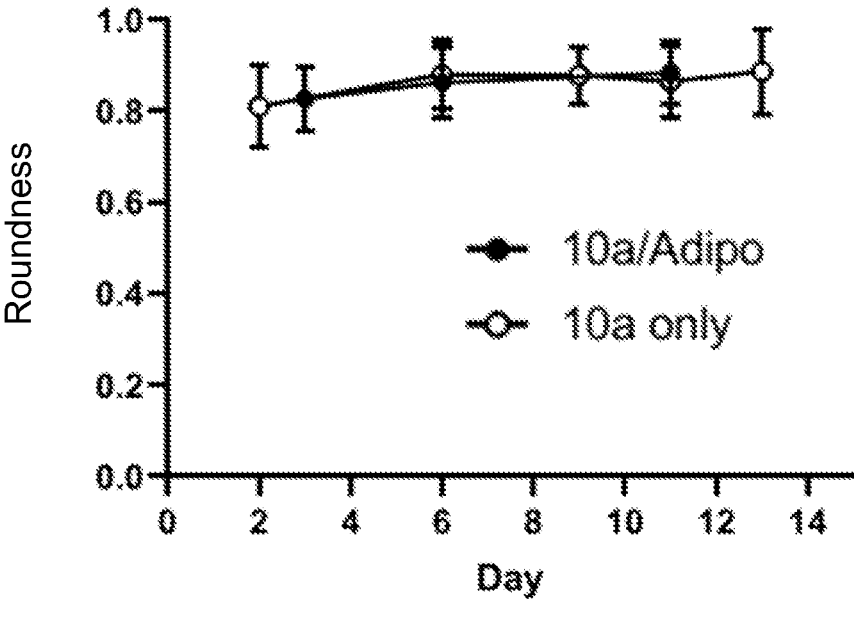
FIG. 23 shows a plot of roundness for organoids with co-culture and without co-culture over time (days), in accordance with an exemplary embodiment of the present disclosure.
Figure 24:
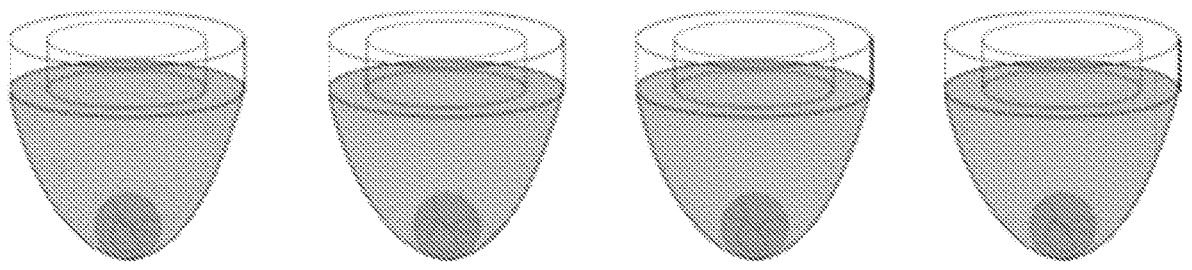
FIG. 24 provides a schematic illustration of hanging drop culture for making organoids, in accordance with an exemplary embodiment of the present invention.
Figure 25:
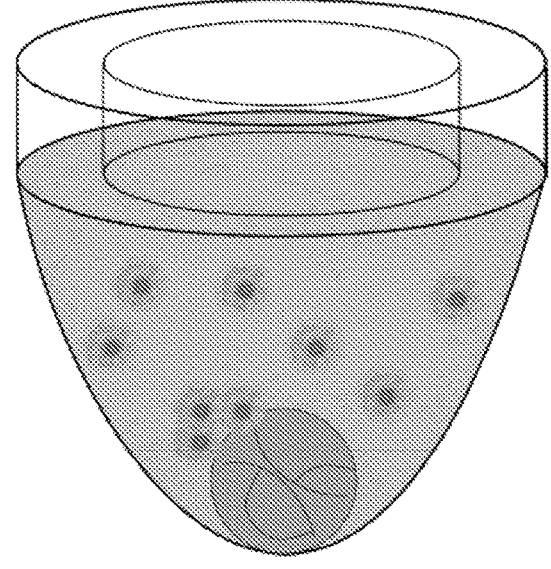
FIG. 25 provides a schematic illustration of exposing organoids to cancer cells in hanging drop culture, in accordance with an exemplary embodiment of the present invention.
Figure 26A:
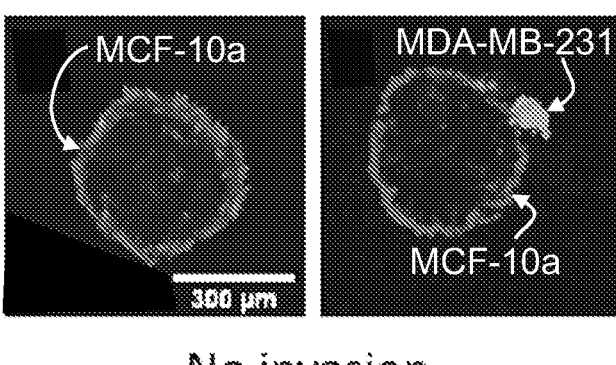
FIGS. 26A through 26C shows confocal images of cancer cell invasion into co-cultured organoids, in accordance with an exemplary embodiment of the present invention.
Figure 26B:
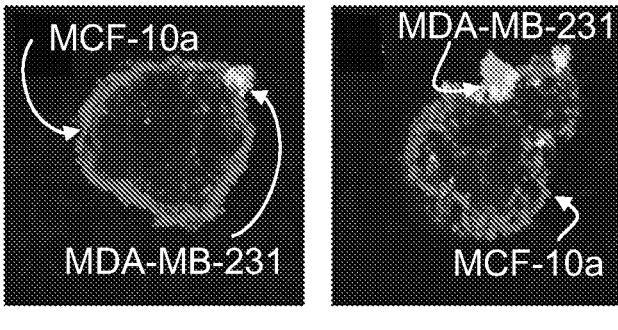
Figure 26C:
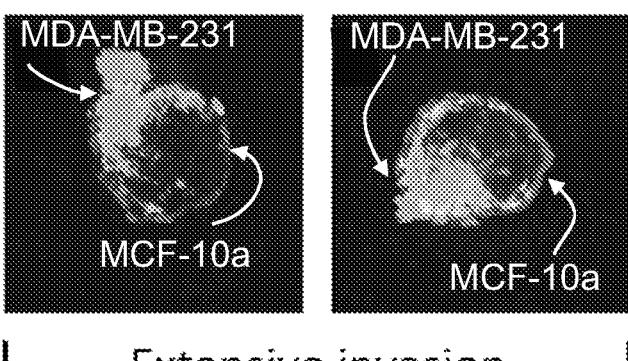
Figures 27A, 27B:
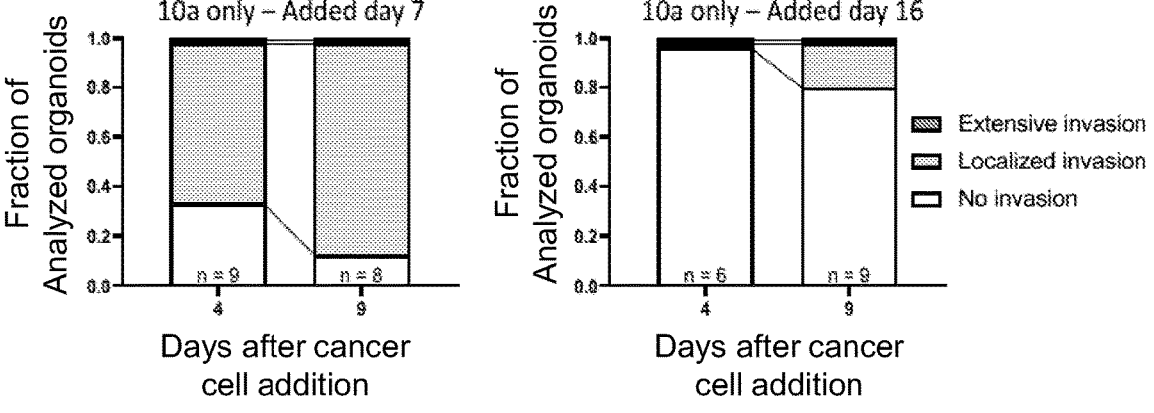
FIG. 27A provides a plot of cancer cell invasion progression for a fraction of single tissue cultured organoids over time (days).
FIG. 27B provides a plot of cancer cell invasion progression for a fraction of co-cultured organoids over time (days).
Figure 28A:
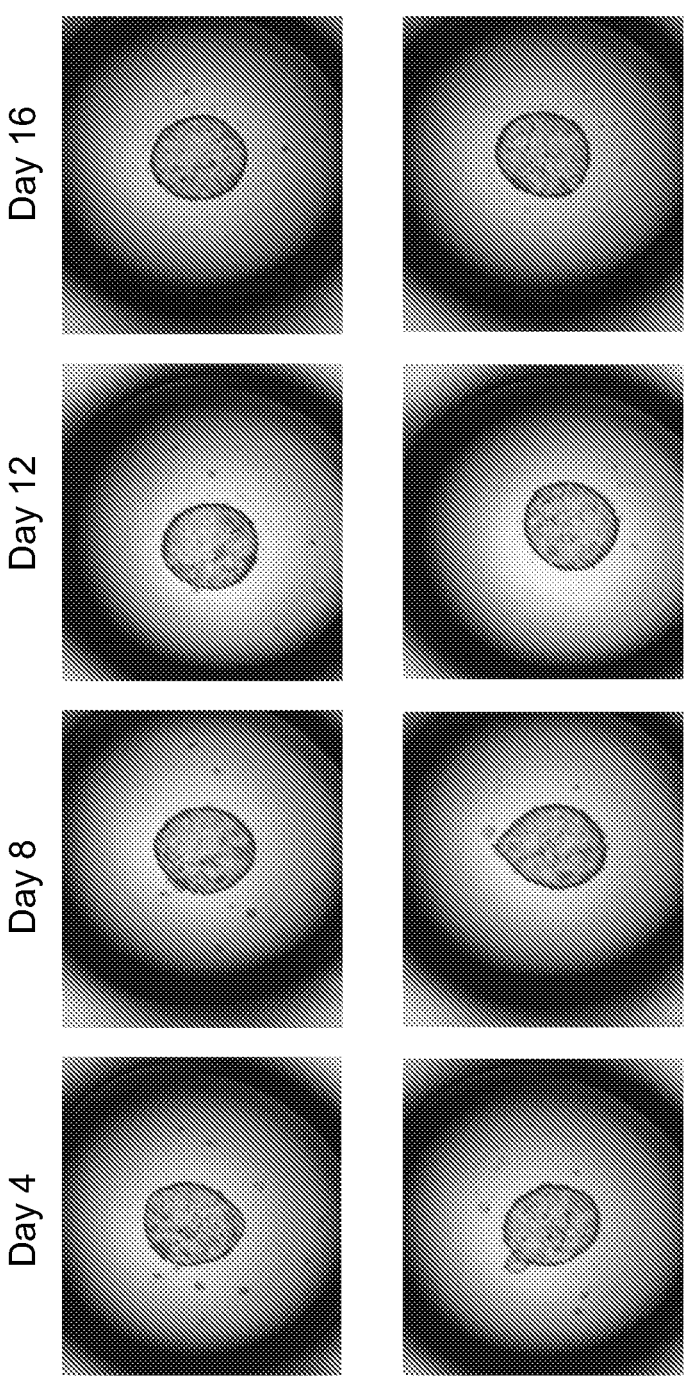
FIG. 28A shows RPTEC organoid formation over time, in accordance with an exemplary embodiment of the present disclosure.
Figure 28B:
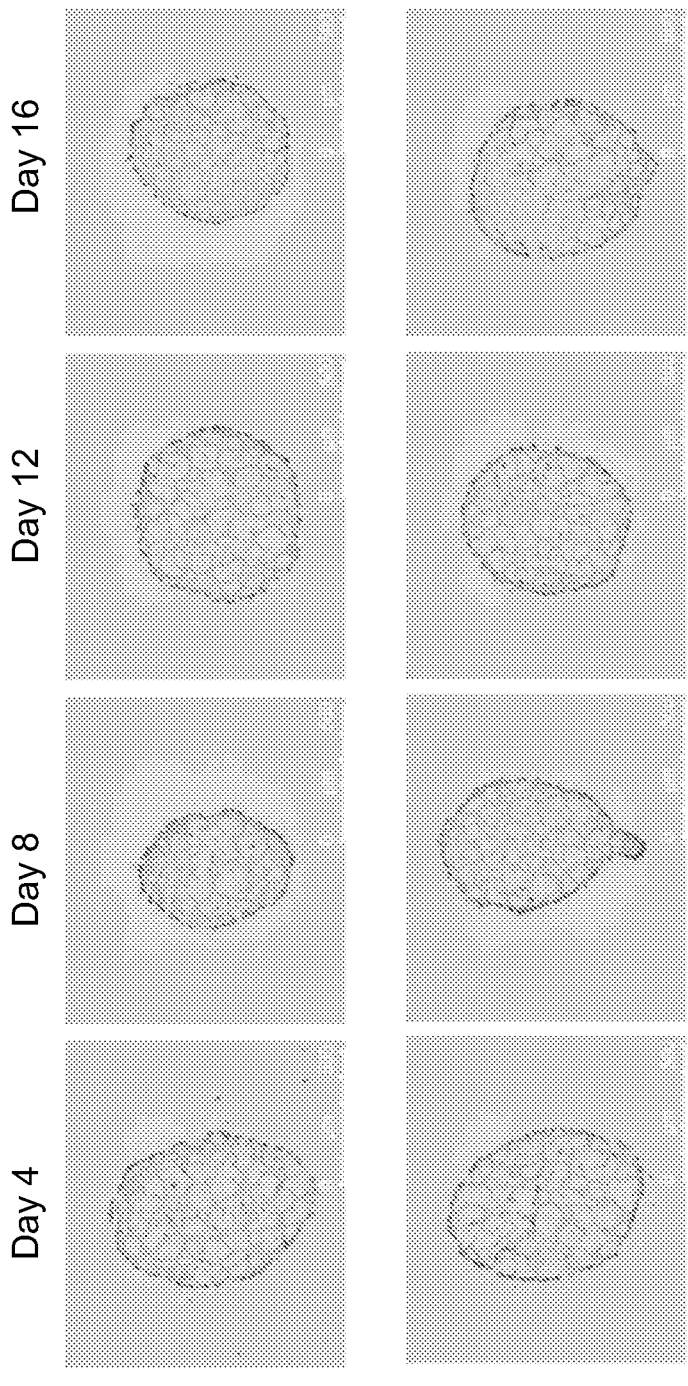
FIG. 28B shows H&E staining of RPTEC organoid formation over time, in accordance with an exemplary embodiment of the present disclosure.
Figure 29:
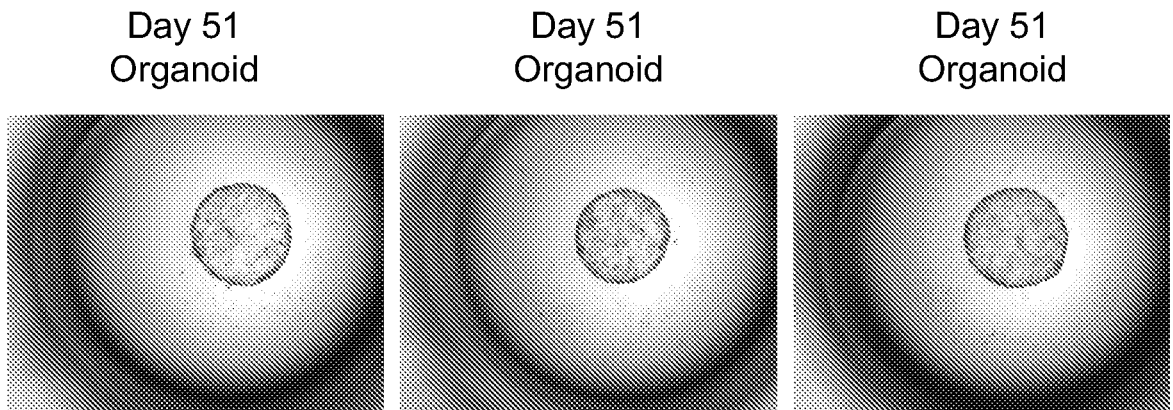
FIG. 29 shows images of day 51 RPTEC organoids, in accordance with an exemplary embodiment of the present disclosure.
Figure 30A:
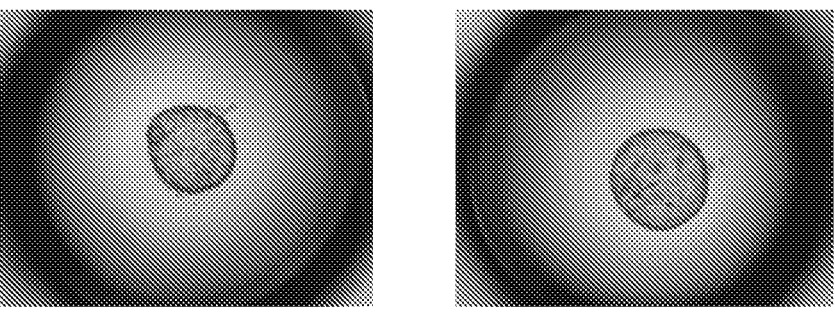
FIG. 30A shows images of organoids cultured using a first batch of Matrigel extracellular matrix, in accordance with an exemplary embodiment of the present disclosure.
Figure 30B:
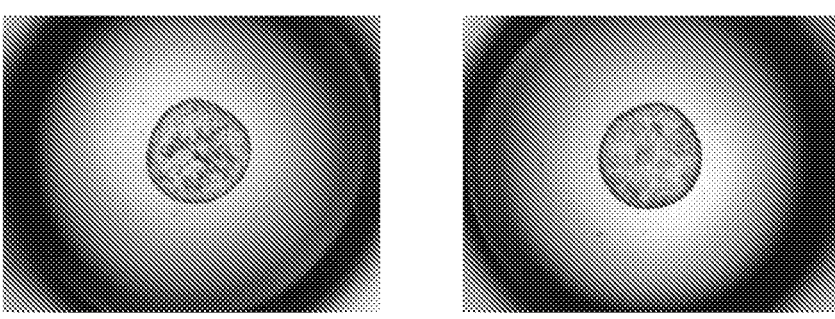
FIG. 30B shows images of organoids cultured using a second batch of Matrigel extracellular matrix different than the first batch, in accordance with an exemplary embodiment of the present disclosure.
Figure 31A:
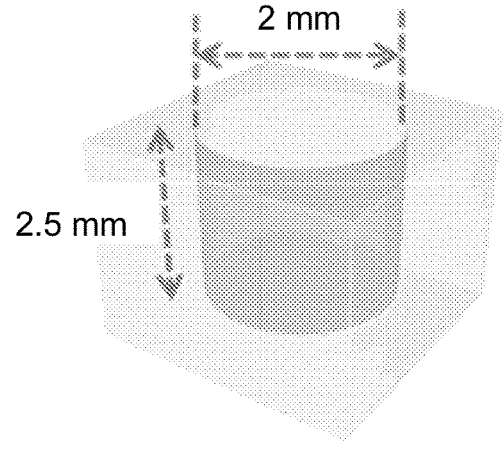
FIGS. 31A and 31B show curvature-controlled PDMS microwells for organoid generation, in accordance with an exemplary embodiment of the present disclosure.
Figure 31B:
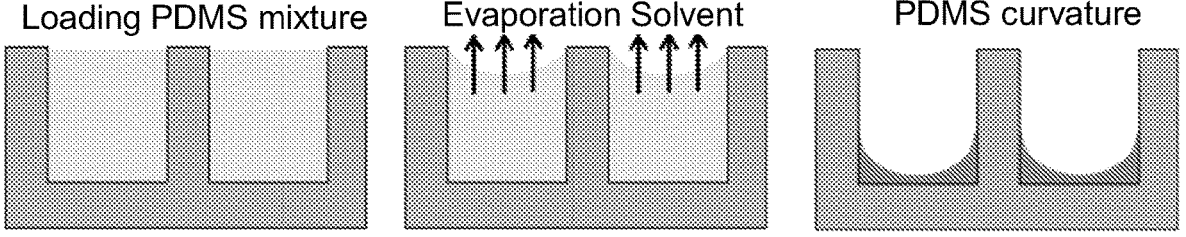

The penetration of MDA-MB-231 cells into the organoid was further assessed by evaluating the timing of cancel cell introduction. Day 7 and day 16 of the organoid culturing was selected for introduction. Cancer cells were allowed to invade the organoid for 9 days (thus, cultured to days 16 and 25, respectively). In these experiments, the MCF10A cells were stably transduced with RFP to contrast with the green fluorescent MDA-MB-231 cells. Furthermore, invasion was analyzed using confocal stacks obtained after optical clearing of the organoids (FIG. 14B and FIG. 19). As provided in FIG. 20, when cancer cells were introduced to the day 7 MCF10A organoids, a majority of organoids were invaded, whereas only a small fraction of day 16 organoids experienced MDA-MB-231 invasion. Importantly, this trend correlates with prominence of the basement membrane-initially, the basement membrane is largely disorganized, has weaker laminin-5 staining, and is highly discontinuous along the inner periphery of the organoid structure (FIG. 21A). However, by day 16, the basement membrane is much more pronounced, with a prominent band along the basal side of the MCF10A epithelium (FIG. 21B).

Because of the ease of use and high-throughput nature of this platform, there are significant biological applications. For example, it is envisioned that the organoid system described herein will be useful for the study of the early invasion steps in DCIS-to-invasive carcinoma progression. DCIS is a type of non-invasive breast cancer that accounts for approximately 25% of all breast carcinoma diagnoses. It has been demonstrated that approximately 30% of untreated cases of DCIS develop IDC within 10 years. At present, there are no biomarkers that can predict which cases of DCIS will progress to invasion. Therefore, there is currently a need for a better understanding of underlying factors responsible for the disease progression and for the development of prognostic biomarkers.

To help study disease progression, a few 2D and 3D models of DCIS have been developed ranging from co-culture spheroid models to microfluidic devices that recapitulate the key physiological features of the disease and serve as potential platforms for assessment of invasion and transition into IDC. One model of interest is the work done by Sameni et al. that details the use of mammary architecture and microenvironment engineering (MAME) to produce 3D models of DCIS invasion (M. Sameni, D. Cavallo-Medved, O. E. Franco, A. Chalasani, K. Ji, N. Aggarwal, A. Anbalagan, X. Chen, R. R. Mattingly, S. W. Hayward, B. F. Sloane, Breast Cancer Res. 2017, 19, 1). While the Sameni et al. model allows for the study of basement membrane breach and invasion, the system is gel-embedded, the cells form small acini, and luminal access is highly limited. On the contrary, microfluidic devices can facilitate investigation of environmental factors of cancer invasion over long periods of time. Previously, Choi et al. developed a microfluidic platform consisting of upper and lower channels to mimic the ductal lumen and vascular layer, respectively. In between the two channels, a DCIS spheroid was placed on a mammary epithelium layer grown on a Matrigel-coated vitrified collagen membrane, which additionally covered a stromal layer consisting of cancer-associated fibroblasts (CAFs) (Y. Choi, E. Hyun, J. Seo, C. Blundell, H. C. Kim, E. Lee, S. H. Lee, A. Moon, W. K. Moon, D. Huh, Lab Chip 2015, 15, 3350.). Another microfluidic platform by Bischel et al. takes advantage of viscous finger patterning to create a hollow lumen lined with MCF10A cells, which can be filled with cells to mimic the disease state. To further increase physiological relevance, the chip contains two side channels, which can be filled with mammary fibroblasts (L. L. Bischel, D. J. Beebe, K. E. Sung, BMC Cancer 2015, 15.). While versatile, microfluidic models are structurally complex and have lower throughput.

In addition to models specific to the study of DCIS, there are several alternative in vitro and in vivo models of breast cancer invasion. While Transwell models are simple and effective to use, they do not encapsulate the cancer microenvironment and can only assess single cell motility. Optimized cancer invasion models also exist, such as the Chemicon/QCM ECMatrix Cell Invasion Assay which measures invasion by post-labelling with fluorescent dye. However, it is only an endpoint assay, and it further does not provide a true cell-produced basement membrane, but rather an exogenous extracellular matrix layer. In vivo invasion assays take advantage of animal basement membranes, such as sea urchin embryo basement membrane (SU-ECM) and chick embryo chorioallantoic membrane (CAM), for more accurate modeling of complex systems. Despite the ease of use of these assays, their animal-origin limits availability of reagents and the differences in drug metabolism with mammals make drug testing difficult.

A method for hanging drop organoids that possess MCF10A cell-produced, native basement membranes is proposed as a viable platform for studying cancer cell invasion. The model's basal-in phenotype described herein allows the organoid to serve as a convenient platform for the study of invasive abilities of breast cancer cells where the "luminal" epithelium on the side opposite the basement membrane is readily accessible from the organoid exterior. Organotypic models that assess invasion in a manner similar to DCIS progression to IDC can pose a challenge for throughput and feasibility if the basement membrane is located on the outside layer, as microinjection into the lumen would be required, and invasion outwards would be assessed. The results in FIG. 20 demonstrate the potential of the basal-in phenotype organoid for successful invasion of triple negative breast cancer cells from the "luminal" side of the epithelium (represented by the media surrounding the organoid), through the basement membrane, to the basolateral side of the epithelium (represented by the inside of the organoid). Cancer cells can be pipetted into the surrounding microenvironment of the organoid, and invasion inwards can be assessed through histology and microscopy. With the presently described platform, typically 192 organoids (every other well of a 384-well plate) can be simultaneously assayed per plate and maintained in culture for 25+ days.

Limitations of the current platform include the use of cell lines rather than primary cells, only mammary epithelial cells and tumor cells, and low-throughput tissue sectioning and clearing methods for much of the analysis. As DCIS transitions to IDC, there is a well characterized and progressive loss of the myoepithelium along with its associated differentiation markers; in vivo, these cells are responsible for basement membrane deposition. As such, the presence or absence of these two layers, in most cases, is used to differentiate between DCIS, DCIS suggestive of invasion, or IDC. Because the present model does not contain a deliberately seeded population of myoepithelial cells, this is one aspect that limits its physiological relevance to the bilayered epithelium found in many types of DCIS. Additionally, although the hanging drop platform is a high-throughput technique, the plates can be difficult to handle because of risk of droplet loss due to bumping, rapid evaporation when left in the open, and difficulty of programming automatic imaging platforms to focus on cells inside hanging droplets. The methods and concepts, however, should be readily expandable to test for use of primary cells, incorporation of additional cell types, and use in mechanistic assays.

Example 5: 2D Cell Culture

MCF10A cells were purchased from ATCC and cultured in DMEM/F12 (Gibco) supplemented with 5% horse serum (Gibco), 20 ng/ml heparin-binding epidermal growth factor (HB-EGF) (Peprotech), 0.5 pg/ml hydrocortisone (Sigma), 100 ng/ml Cholera toxin (Sigma), 10 μg/ml insulin (Sigma), and 1% penicillin/streptomycin (pen/strep) (Gibco). MDA- MB-231 stably transduced with GFP were grown in DMEM (Gibco) supplemented with 10% fetal bovine serum (FBS) (Gemini), 1% pen/strep, and 1% GlutaMAX (Gibco). Cultures were maintained at 37° C. and 5% $CO_2$ in T75 culture flasks. Cells in 2D culture were routinely passaged at 70-80% confluence.

Primary renal proximal tubule epithelial cells (RPTEC) were cultured in renal epithelial cell basal media supplemented with 0.5% FBS, 10 nM triiodothyronine, 10 ng/mL rh EGF, 100 ng/mL hydrocortisone hemisuccinate, 5 μg/mL rh insulin, 1.0 μM epinephrine, 5 μg/mL transferrin, and 2.4 mM 1-alanyl-glutamine. Cells were maintained in 2D culture in T75 flasks and were passaged at 95% confluency. Primary RPTEC cells were used below passage 6.

Example 6: MCF10A RFP Transduction

MCF10A cells were seeded at a density of 100,000 per well in a 6-well tissue culture plate. After allowing cells to attach overnight, media was aspirated, and cells were rinsed with PBS. Then, 2 mL of transduction media containing heat-inactivated horse serum, polybrene at a final concentration of 5 μg/mL (Sigma #107689), and RFP lentivirus (Cellomics Technology) at a final concentration of 400,000 TU/mL for a total multiplicity of infection (MOI) of 8 was added to the cells. Transduction occurred for 8.5 hours, after which the transduction media was aspirated, and the cells were rinsed with sterile PBS. Then 2 mL of fresh media was added to the cells. The cells were expanded and the RFP-hi positive population was selected for using florescence-activated cell sorting (FACS). Before seeding into organoids, the cells were maintained in growth media containing 1 μg/mL puromycin to maintain selective pressure against unlabeled cells.

Example 7: Hanging Drop Culture of 3D MCF10A Mammary Organoids

To grow MCF10A mammary organoids in hanging drop culture, previously described custom plates were soaked overnight in 0.1% F108 pluronic solution (Sigma 542342), rinsed with water, and UV sterilized for 20 minutes on each side with a UVP Crosslinker (Analytik Jena). To minimize evaporation of the drops, the plate was sandwiched between a 96-well round bottom plate, and the wells filled with distilled water. To provide further humidity, the troughs of the hanging drop plate were filled with distilled water and sterile gauze pads. Organoids were seeded and maintained in hanging drop culture. Briefly, 3000 MCF10A cells were seeded in every other well of a 384-well hanging drop plate in a final volume of 25 μL. The cells were supplemented with 0.24% Methocel (A4M, Sigma), 1.5% Matrigel (Corning, #356231 Growth Factor Reduced Basement Membrane Matrix), and 10% FBS to promote initial aggregation, growth, and subsequent hollowing. To ensure the organoids exhibited a basal-in phenotype, cold Matrigel was added to pre-warmed growth media containing FBS and Methocel prior to introducing the cells. On day 3 of organoid culture, the media was exchanged 3 times to wash out the seeding supplements using a CyBio FeliX liquid handling machine (Analytik Jena). To exchange media, 9 μL was removed, and 10 μL was added to account for evaporation. For routine culture, media was exchanged 2 times every 2-3 days. Organoids were maintained in culture for 16 to 25 days. For co-culture experiments, 300 MDA-MB-231 cells were seeded with 3000 MCF10A cells. Cells were seeded in the same media as the MCF10A mono-culture organoid seeding media containing 1.5% Matrigel, 10% FBS, and 0.24% Methocel in complete MCF10A growth media. During routine media changes, complete MCF10A growth media was also used to replenish the hanging drops following the exchange protocol described above.

Example 8: Hanging Drop Culture of 3D RPTEC Organoids

To grow RPTEC organoids in hanging drop culture, previously described custom plates were soaked overnight in 0.1% F108 pluronic solution (Sigma 542342), rinsed with water, and UV sterilized for 20 minutes on each side with a UVP Crosslinker (Analytik Jena). To minimize evaporation of the drops, the plate was sandwiched between a 96-well round bottom plate, and the wells filled with distilled water. To provide further humidity, the troughs of the hanging drop plate were filled with distilled water and sterile gauze pads. Organoids were seeded and maintained in hanging drop culture. Briefly, 3000 RPTEC cells were seeded in every other well of a 384-well hanging drop plate in a final volume of 25 µL. The cells were supplemented with 0.24% Methocel (A4M, Sigma), 1.5% Matrigel (Corning, #356231 Growth Factor Reduced Basement Membrane Matrix), and 2.4% FBS to promote initial aggregation, growth, and subsequent hollowing. To ensure the organoids exhibited a basal-in phenotype, cold Matrigel was added to pre-warmed growth media containing Methocel prior to introducing the cells. On day 3 of organoid culture, the media was exchanged 3 times to wash out the seeding supplements using a CyBio FeliX liquid handling machine (Analytik Jena). To exchange media, 9 µL was removed, and 10 µL was added to account for evaporation. For routine culture, media was exchanged 2 times every 2-3 days. Organoids were maintained in culture for 60+ days.

Example 9: 3D Organoid Culture in ULA Culture

To MCF10A mammary organoids in 3D ULA culture, cells were seeded in 384-well U bottom Ultra-Low Attachment (ULA) plates (S-bio #MS-9384UZ, lot 90639317), centrifugated (1000×rpm RT 5 min), and maintained in 384-well ULA plate using the various culture conditions. Briefly, 3000 MCF10A cells were seeded in each well in a final volume of 25 µL. The cells were supplemented with 0.24% methocel A4M (Sigma #94378, lot BCBR9701V), 0-240 pg/mL Matrigel (Corning #256231, 8.5 mg/ml, lot 9301006), and 10% FBS (GemiBio #900-108, lot A52G00J). On day 3 of organoid culture, the media was exchanged 3 times to wash out the seeding supplements using a CyBio FeliX liquid handling machine (Analytik Jena). For routine culture, media was exchanged 2 times every 2-3 days. Organoids were maintained in culture for 16 days.

To test the effect of Matrigel amounts on the organoid formation, 0, 40, 80, 120, 160, 200, and 240 µg/mL Matrigel were contained in the culture conditions. To test the effect of the growth factor types and amounts on cell differentiation and the organoid formation, 0, 0.1, 1, 10, and 100 ng/mL of HB-EGF and RH-EGF (Peprotech #AF-100-15, lot 1020AFC05) each were contained in the culture conditions. In addition, on day 6 of organoid culture, growth factors were removed by medium changing 7 times in each condition.

Figures 32A, 32B:
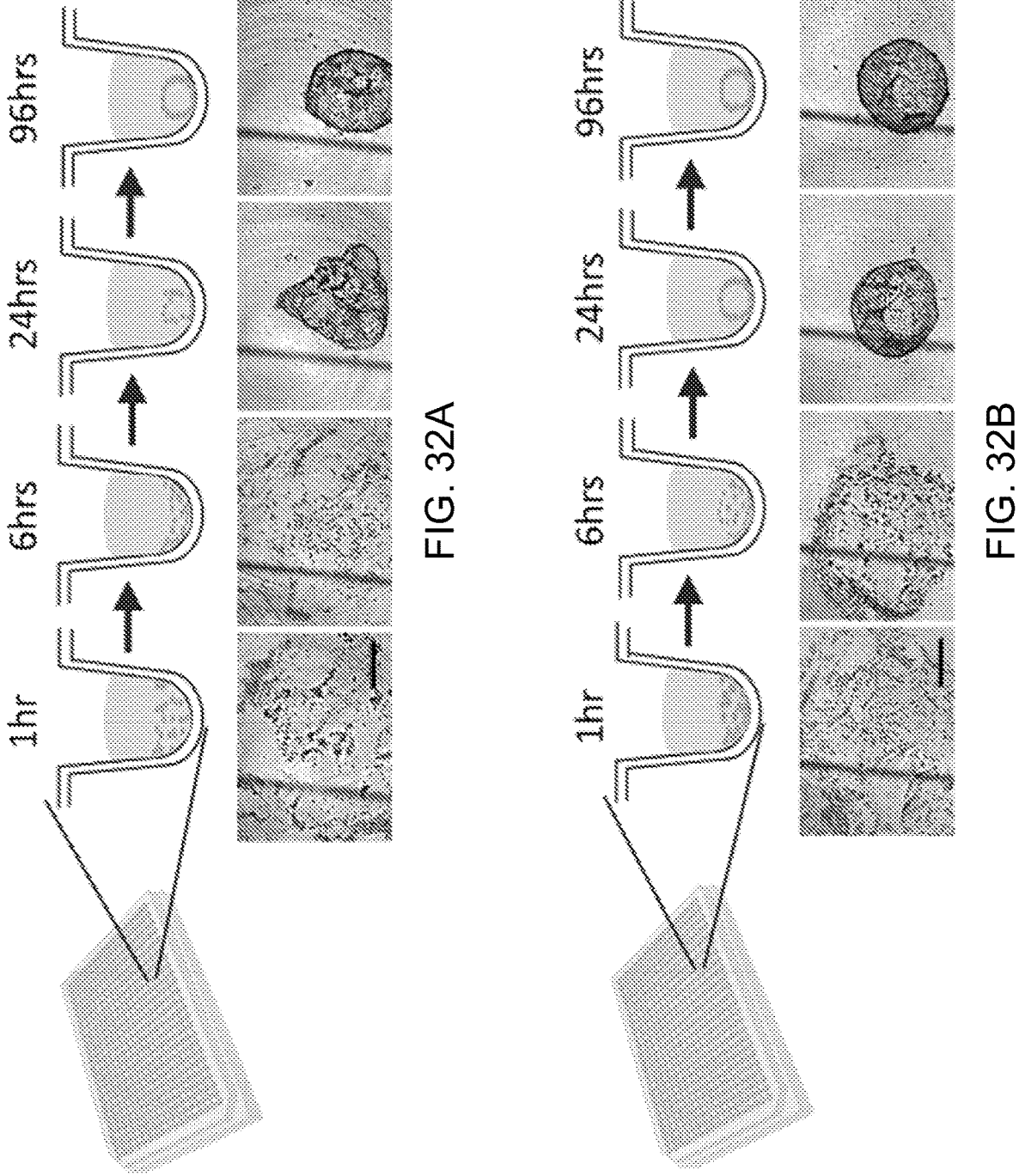
FIGS. 32A and 32B show differences in organoid formation according to plate conditions without centrifugation (FIG. 32A) and with centrifugation at 1000 rpm for 5 minutes (FIG. 32B), in accordance with an exemplary embodiment of the present disclosure.
Figure 33:
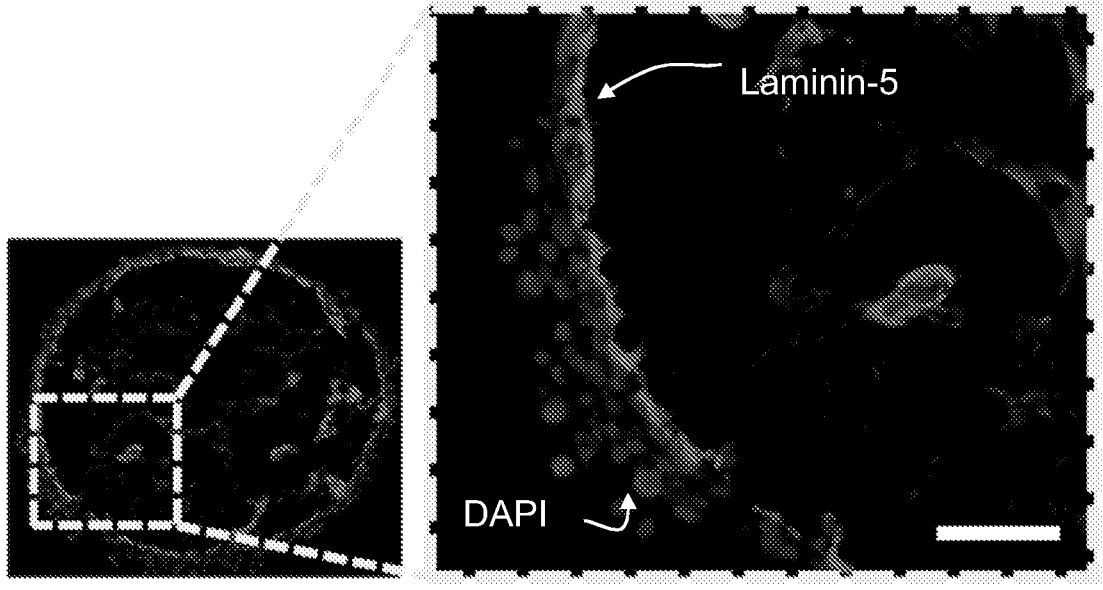
FIG. 33 shows Laminin-5 staining of a day 16 organoid with inset showing 40x image, with laminin-5 layer on the inner side of the structure, in accordance with an exemplary embodiment of the present disclosure.

Example 10: MCF10A Organoid Formation in 384-Well U-Bottom ULA Plate and Fabrication of Concave Microwell Plate With a need for more efficient cell aggregation, the method described herein was applied with a commercial microwell plate. 384-well U-bottom ultralow attachment (ULA) plates were tested, which have a higher curvature than the previously unsuccessfully tested 96-well format ULA plate. The organoid formation slowly formed a rounded structure (FIG. 32A). An initial centrifugation step (1000 rpm for 5 min at room temperature) was added to further promote cell aggregation and quickly formed a uniform rounded shape (FIG. 32B). As a result, a high yield MCF10A organoids were generated. The U-bottom plate organoid basal-in phenotype generation was compared to the hanging drop plate organoid basal-in phenotype generation. The organoid sections were stained with laminin-5, an indicator of cell-produced basement membrane, that is not present in significant amounts in Matrigel. FIG. 33 shows the staining confirmed that MCF10A organoids cultured in U-bottom ULA plates also exhibit a basal-in phenotype. Initial centrifugations step promotes cell aggregations and a uniform rounded shape at the beginning.

The bottom of the microwell is concave shape and can be induced the cell aggregation for the formation of organoids. The concave microwell plate was generated by using capillarity-induced solvent evaporation. In detail, uncured PDMS mixture of a prepolymer and a curing agent in a 10:1 ratio was dissolved in tert-butanol with various concentrations at 10, 20, 30, and 40%, respectively. Then, a mixture was poured onto the cylindrical microwell plate and incubated at 70° C. for 12 h.

Figure 34:
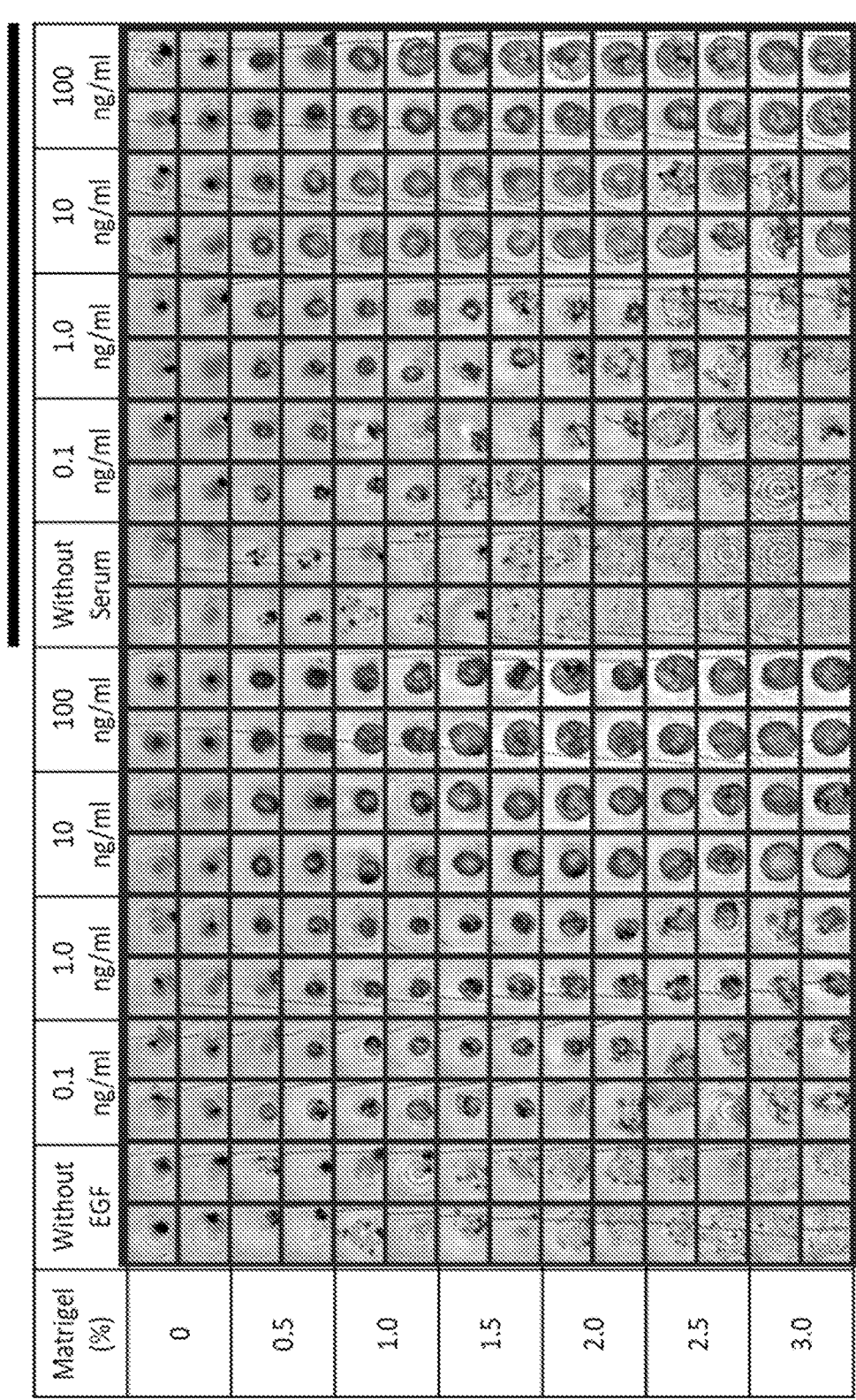
FIG. 34 shows entire ULA plate image of organoid formation under various culture conditions, in accordance with an exemplary embodiment of the present disclosure.

Example 11: Live Cell Imaging of Organoid Formation Under Different Culture Conditions Taking advantage of this new U-bottom plate organoid formation method that is compatible with in-incubator live cell imaging, different growth factors and Matrigel conditions were screened to assess the impact on organoid formation. Conditions for one-drop, one-organoid formation of basal-in phenotype organoids include the use of low Matrigel concentrations (110~130 ug/ml), inclusion of Methocel (0.24%), and higher serum concentrations (10% FBS) at seeding. Importantly, adding Matrigel to pre-warmed growth media containing FBS and Methocel to form the organoids was determined to be a key materials processing condition. Having the right amounts of Matrigel and growth factors in the initial organoid formation process was found to be important. Systematic observation and analysis, however, was difficult due to incompatibility of hanging drop cultures with automated imaging systems. In some embodiments described herein, 3000 MCF10A cells were seeded into automated imaging-compatible 384-well ULA plate similar to what was done previously in 384 hanging drop plates but with different amounts of Matrigel and different amounts and types of growth factors: heparin-binding EGF-like growth factor (HB-EGF) or recombinant human-EGF (RH-EGF). The organoid formation and culture process were monitored for 16 days using an Incucyte S3 (Sartorious) in-incubator microscope system. FIG. 34 shows one plate image that contains organoid formation under various conditions taken on Day 16.

A combination of 119 different culture conditions with varying Matrigel concentrations and the proliferative growth factor EGF or HB-EGF were tested. In previous research, it was demonstrated that a combination of low Matrigel concentration and 10% FBS promoted expansion of organoids. Therefore, the presence or absence of serum was also tested. The effect of removing growth factor (EGF or HB-EGF) at day 6 was also assessed to examine growth factor effects to organoid maintenance after formation. The various conditions for real-time cell imaging in ULA culture are depicted in FIG. 34.

While organoids were maintained for 16 days in ULA culture, they were imaged using an Incucyte S3 (Sartorious) in-incubator microscope system. The Incucyte S3 performs auto-focus on each well of the microwell plate. 10× brightfield images were acquired at 1 hr. intervals for first day, every 2 hours for second day, and then every 4 hours after that for rest of the experiments.

Example 12: Automated Image Analysis

One challenge that arises from performing live cell imaging in 384 well plates over 16 days is the accumulation of large numbers (thousands) of images. While the Incycte comes with an image analysis software from the manufacturer, the capabilities are often found to be insufficient for analysis of the organoids described herein. An automated MATLAB script was developed based on morphological image processing to (1) extract the projected area and (2) measure the circularity of the largest organoid/cell cluster in each image. Using this method, images taken from microwells representing 119 different conditions were captured over the course of 16 days. Because of the limited field of view of the Incucyte images and because not all cellular structures are centered within the microwells, not all images include the entire organoid. For those images, the organoids were considered as a partial sphere. However, despite this limitation, the analysis method was still robust enough to differentiate between proper- and poor-forming organoids.

Example 13: Time Course Analysis

Figure 35A:
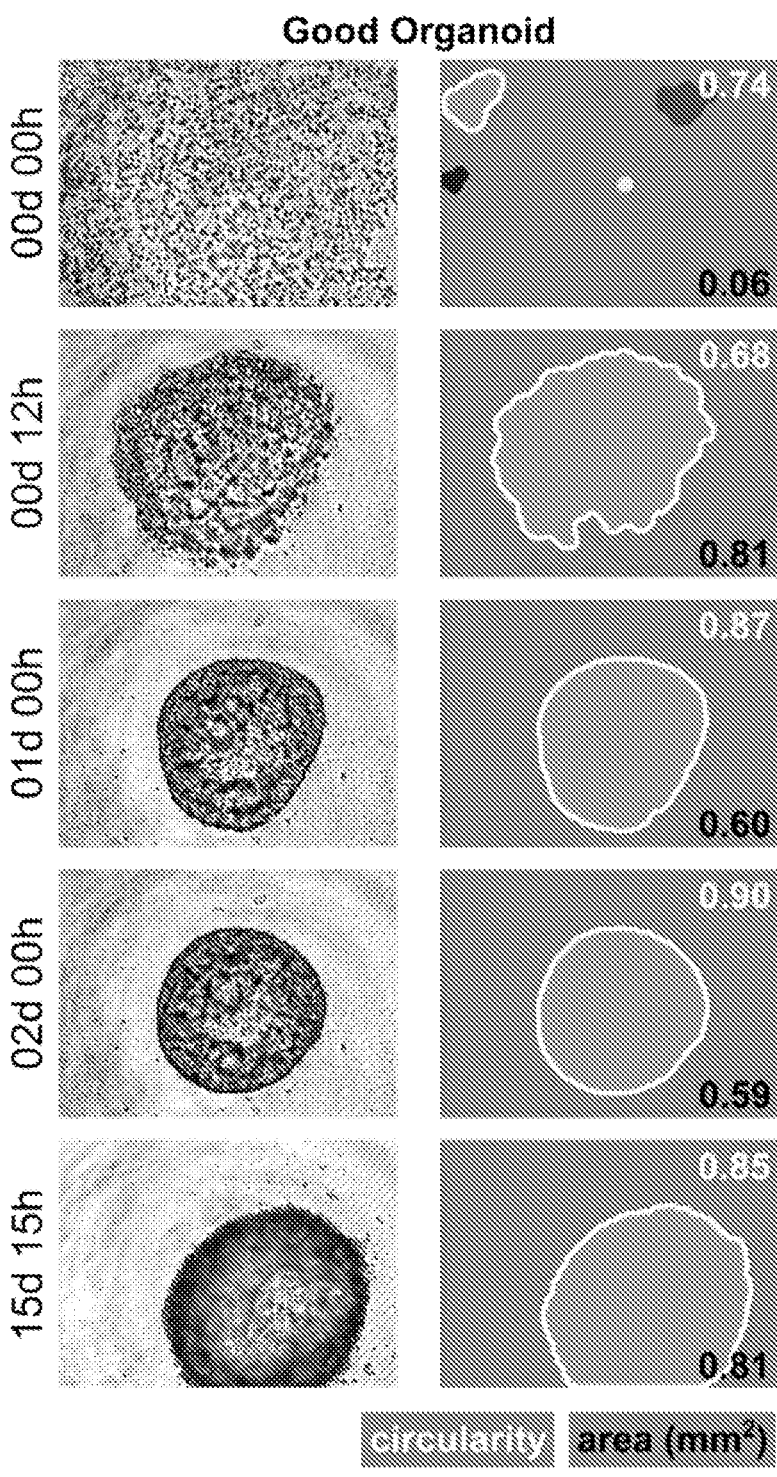
FIGS. 35A and 35B show image analysis comparing good organoids (FIG. 35A) and bad organoids (FIG. 35B) over time, in accordance with an exemplary embodiment of the present disclosure.
Figure 35B:
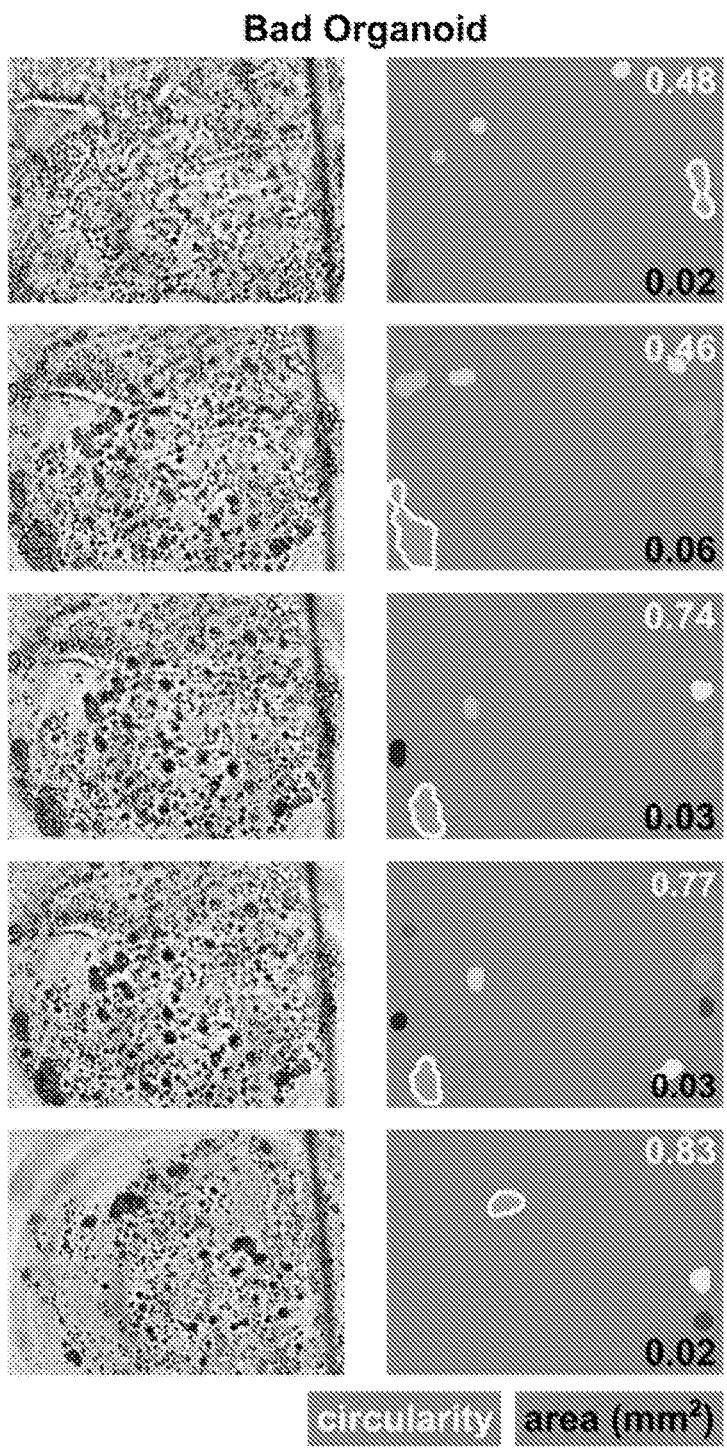
Figure 36A:
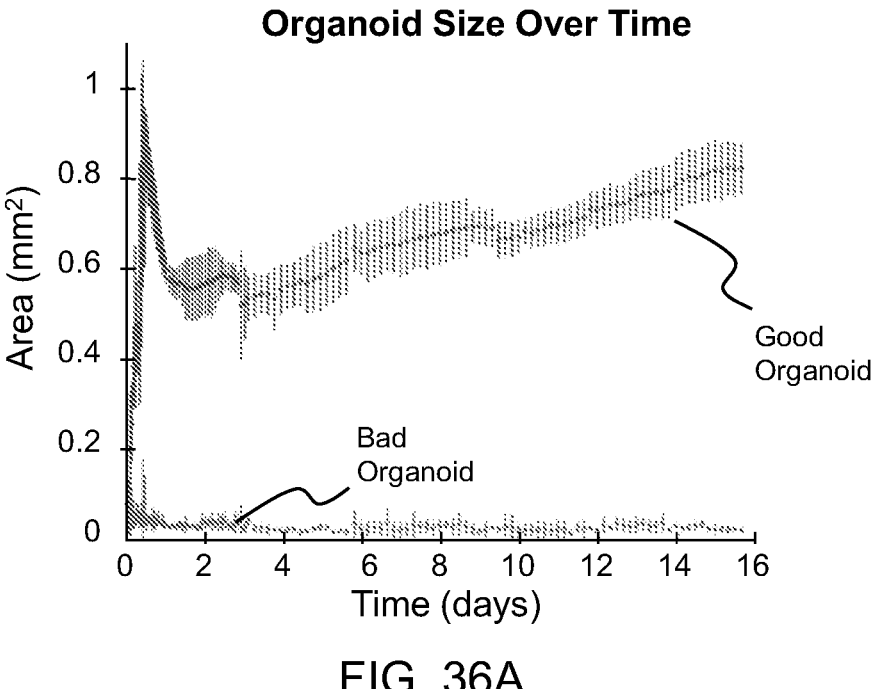
FIG. 36A shows a plot of area ($mm^2$) versus time (days) comparing size of good organoids to size of bad organoids over time, in accordance with an exemplary embodiment of the present disclosure.
Figure 36B:
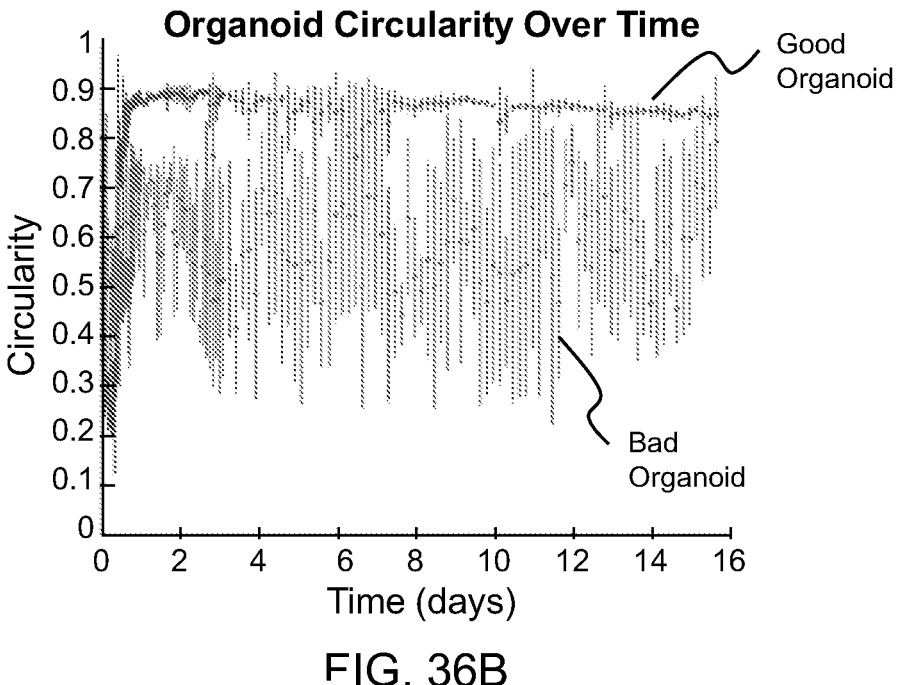
FIG. 36B shows a plot of circularity versus time (days) comparing circularity of good organoids to circularity of bad organoids over time, in accordance with an exemplary embodiment of the present disclosure.

Excluding conditions without any Matrigel, or serum, or growth factor that do not form organoids, organoid projected area and circularity over time were plotted. FIGS. 35A and 35B show comparisons of image analysis between good and bad organoid formation. Each group has all 4 replicates and measured area and circularity, as shown in FIGS. 36A and 36B.

Example 14: Image Analysis on the Organoid Culture Conditions

Figure 37A:
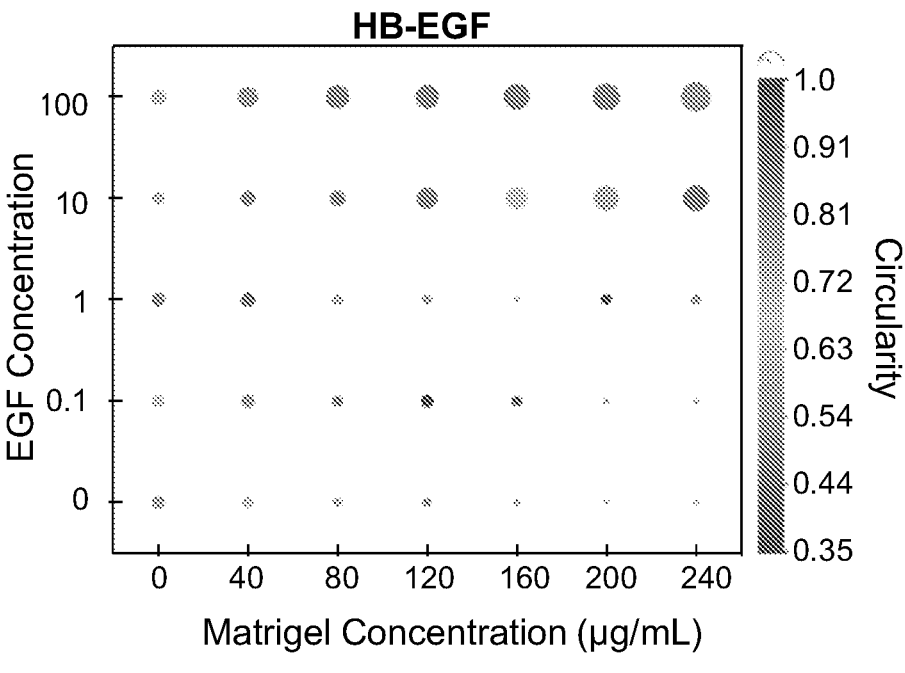
FIGS. 37A and 37B show 2D-plot of EGF Concentration versus Matrigel Concentration (pg/mL) with size and circularity of two different types of growth factors, in accordance with an exemplary embodiment of the present disclosure.
Figure 37B:
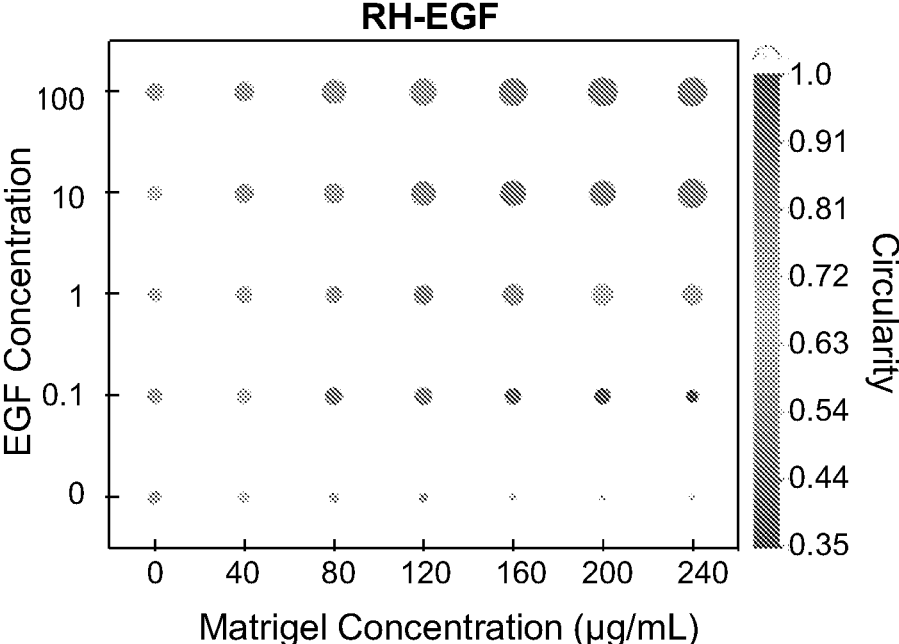
Figures 38A, 38B, 38C:
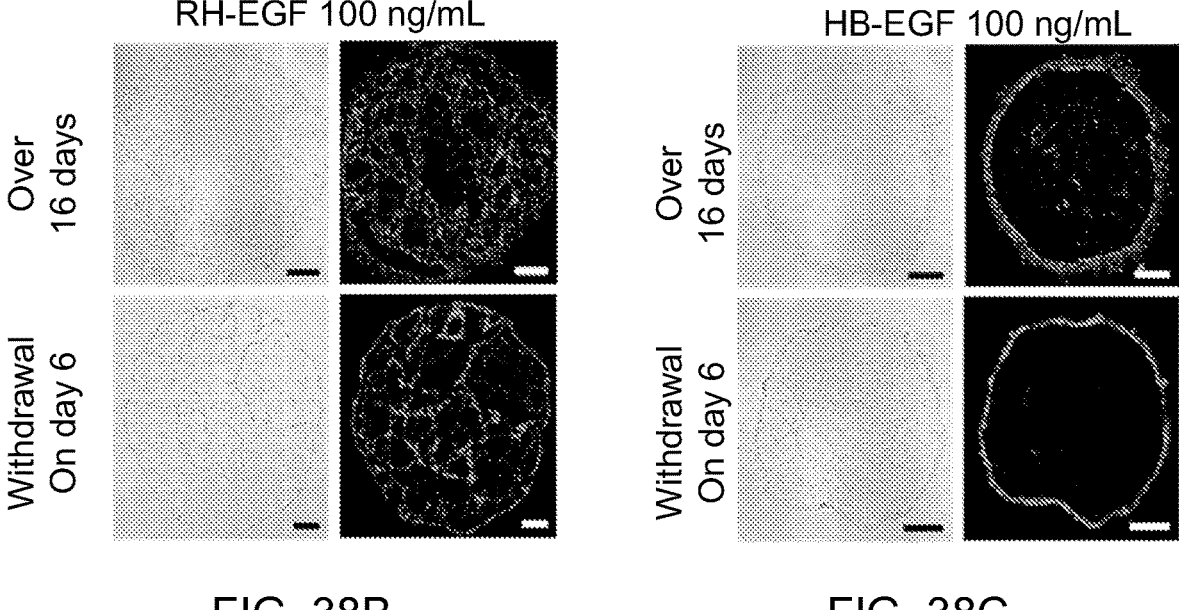
FIGS. 38A through 38C show brightfield and immunofluorescence images of day 16 organoids with varying types and amounts of growth factor, in accordance with an exemplary embodiment of the present disclosure.
Figure 41A:
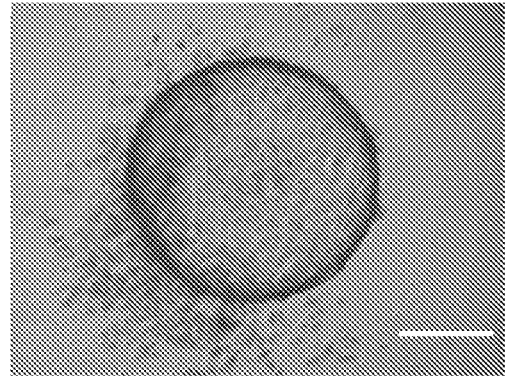
FIG. 41A provides a brightfield image of day 16 lung organoid, in accordance with an exemplary embodiment of the present disclosure.
Figure 41B:
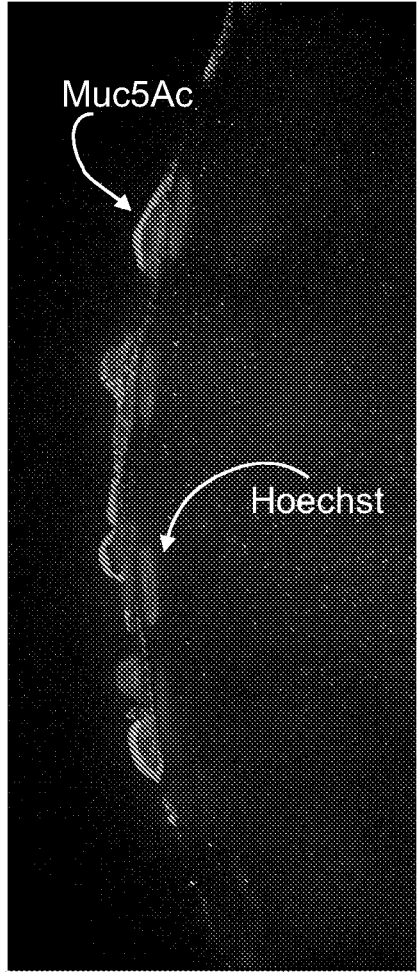
FIG. 41B shows an immunofluorescence image of day 16 lung organoid showing various types of cell markers, in accordance with an exemplary embodiment of the present disclosure.
Figure 42A:
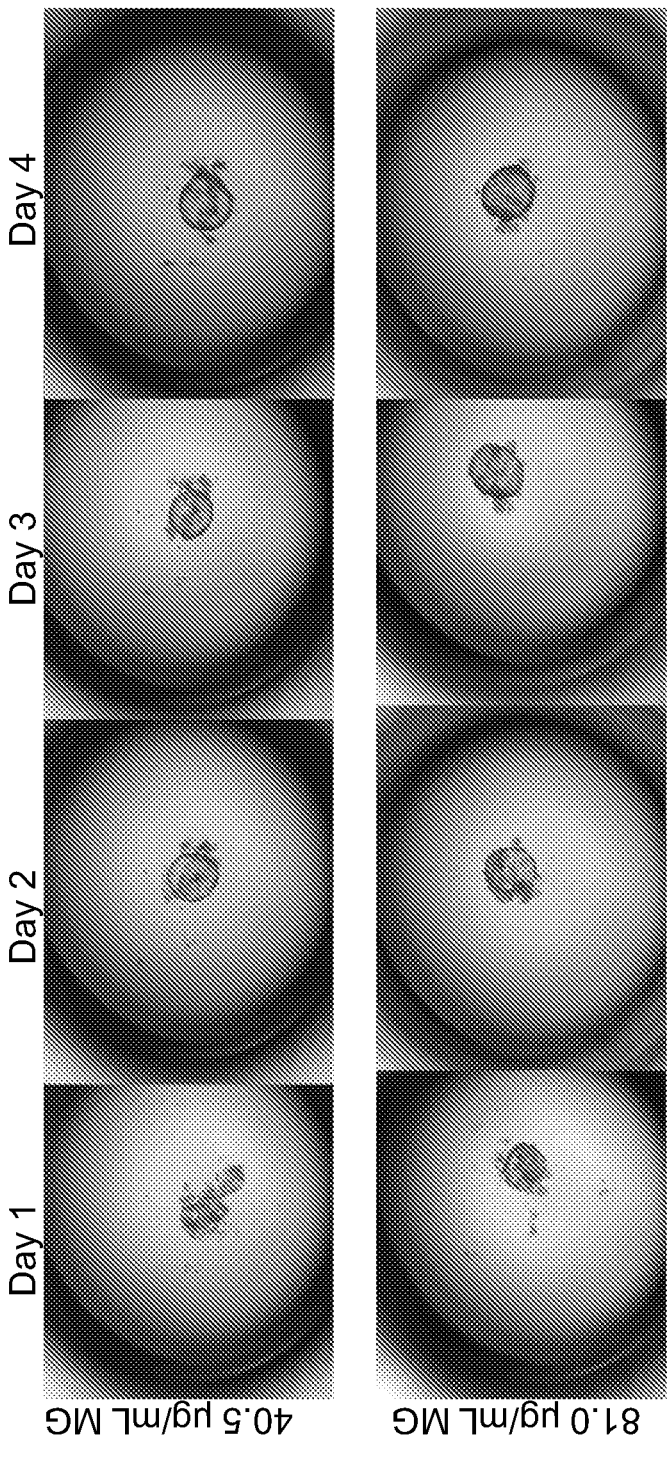
FIGS. 42A and 42B show lung organoid formation with varying concentrations of Matrigel, in accordance with an exemplary embodiment of the present disclosure.
Figure 42B:
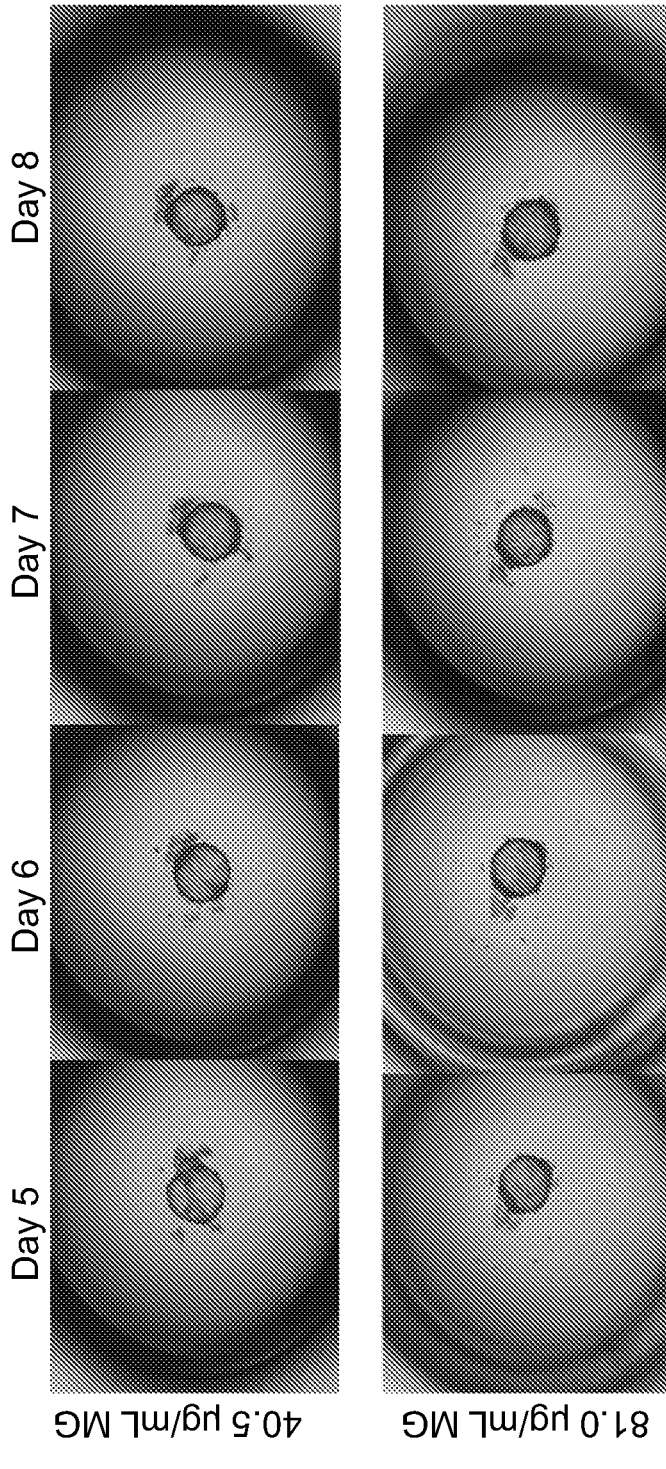
Figure 43:
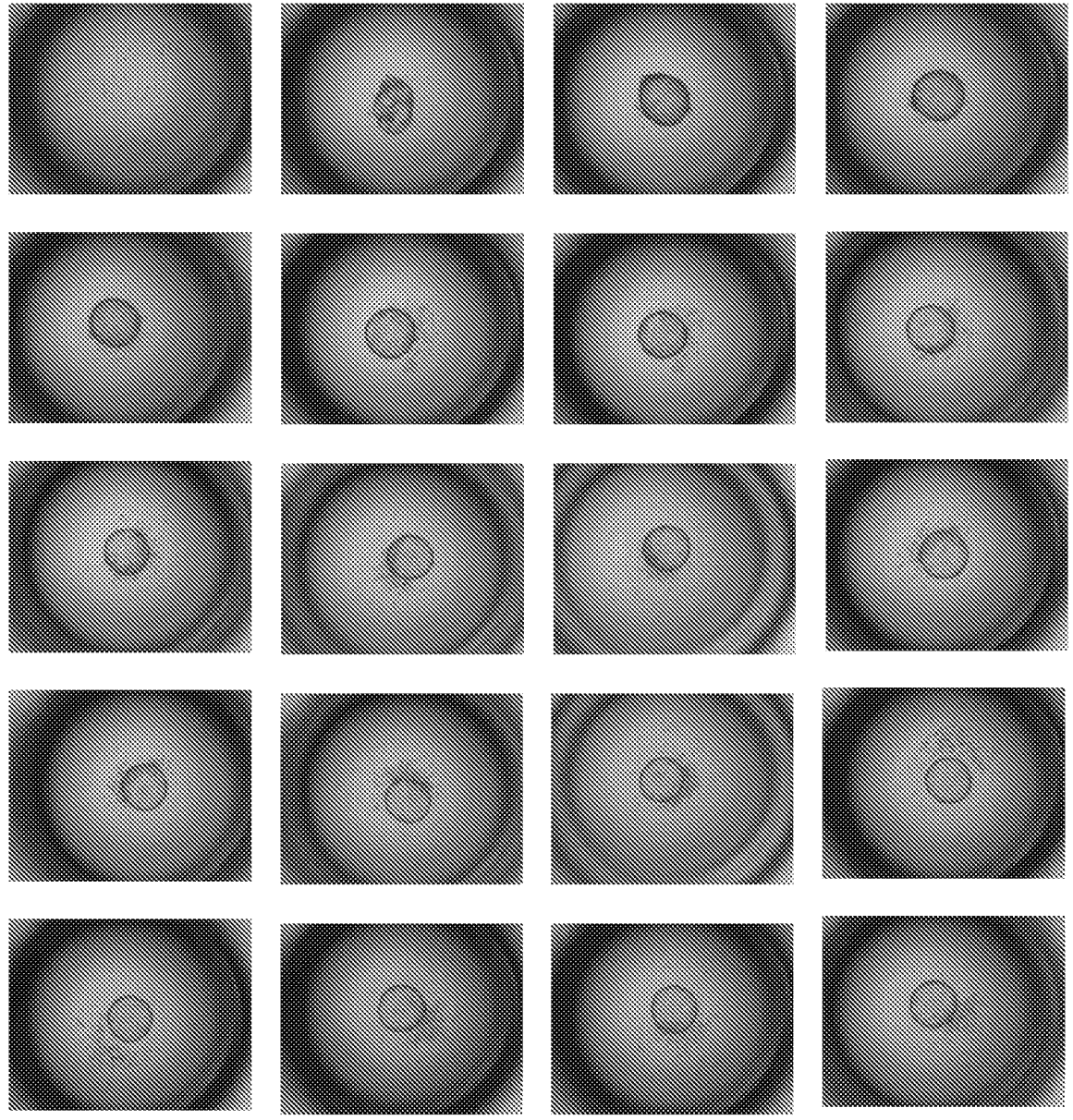
FIG. 43 shows lung organoid formation from day 0 to day 46, in accordance with an exemplary embodiment of the present disclosure.
Figure 44A:
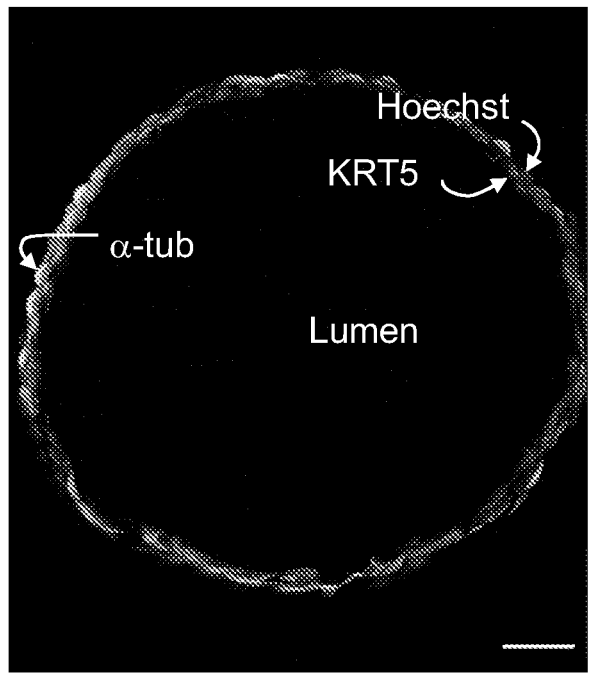
FIGS. 44A through 44F show immunofluorescence images of lung organoids showing various types of cell markers, in accordance with an exemplary embodiment of the present disclosure.
Figure 44B:
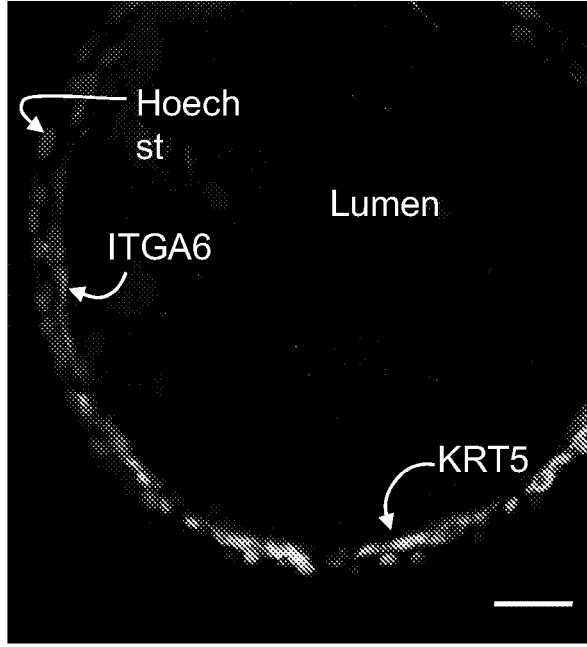
Figure 44C:
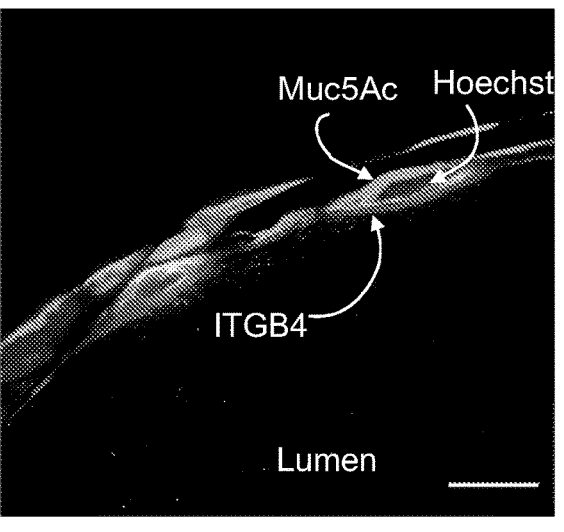
Figure 44D:
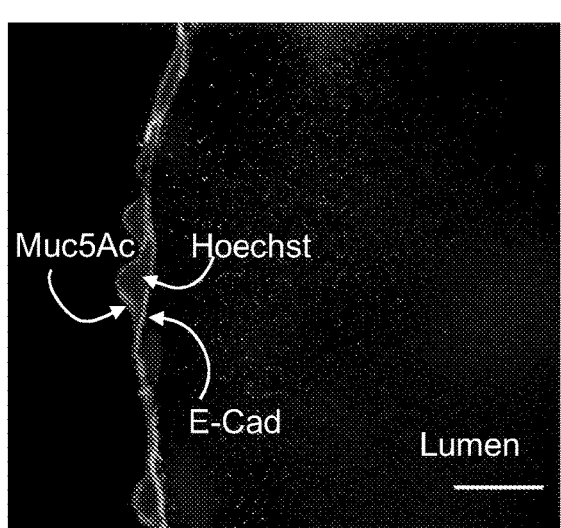
Figure 44E:
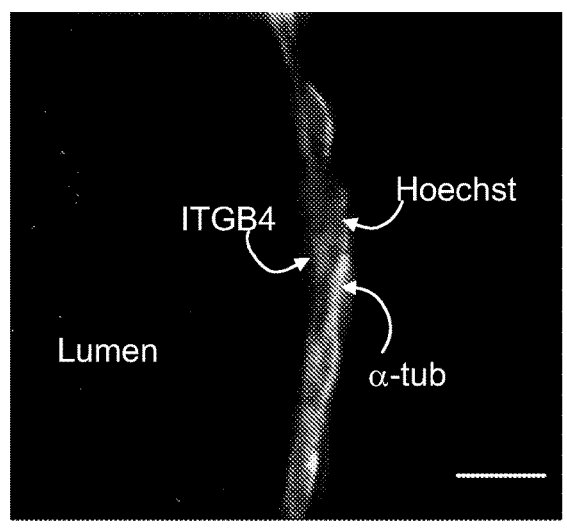
Figure 44F:
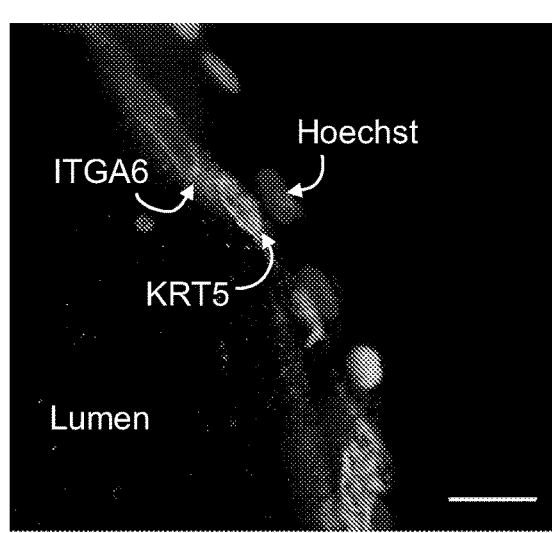
Figure 45A:
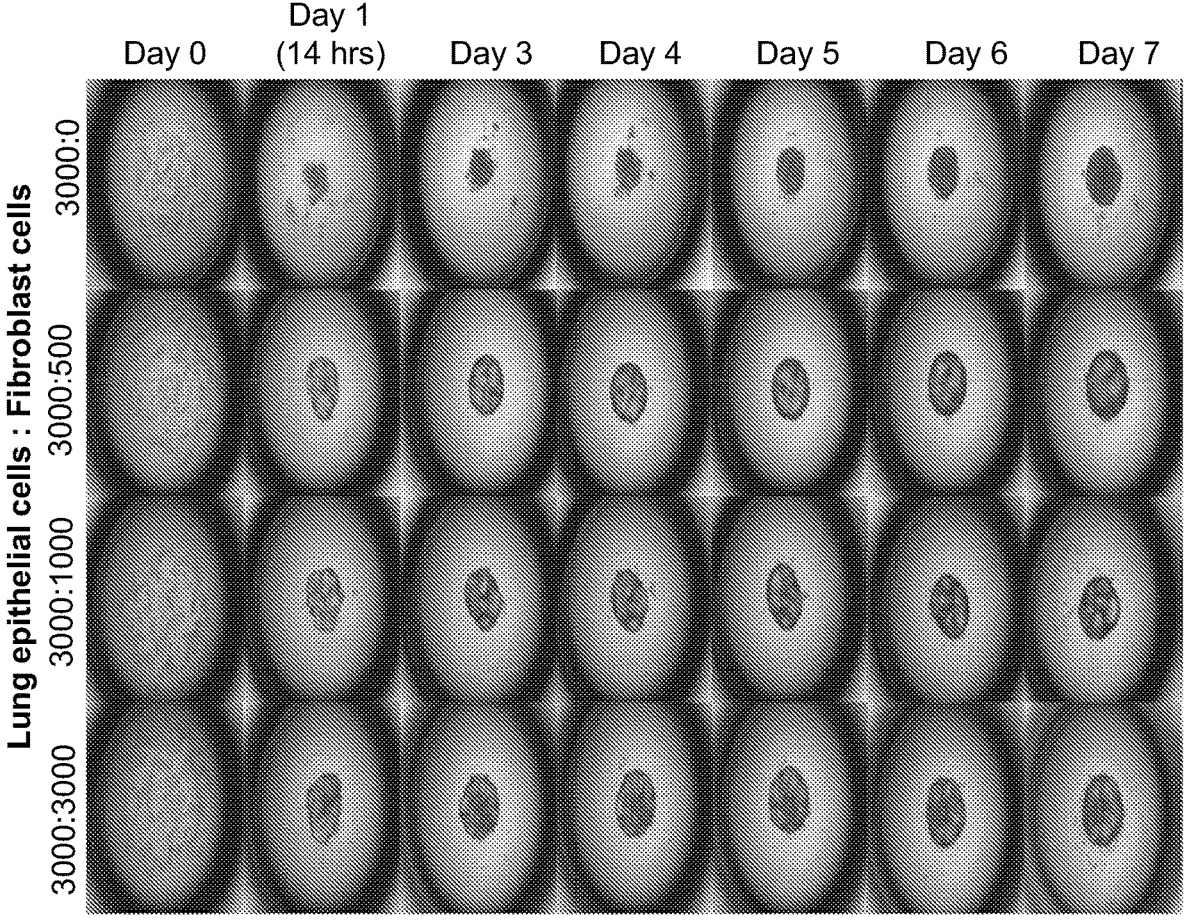
FIGS. 45A and 45B show lung epithelial cell (NCI-H441 cells) organoid formation over time with varying concentrations of normal human lung fibroblast co-culture, in accordance with an exemplary embodiment of the present disclosure.
Figure 45B:
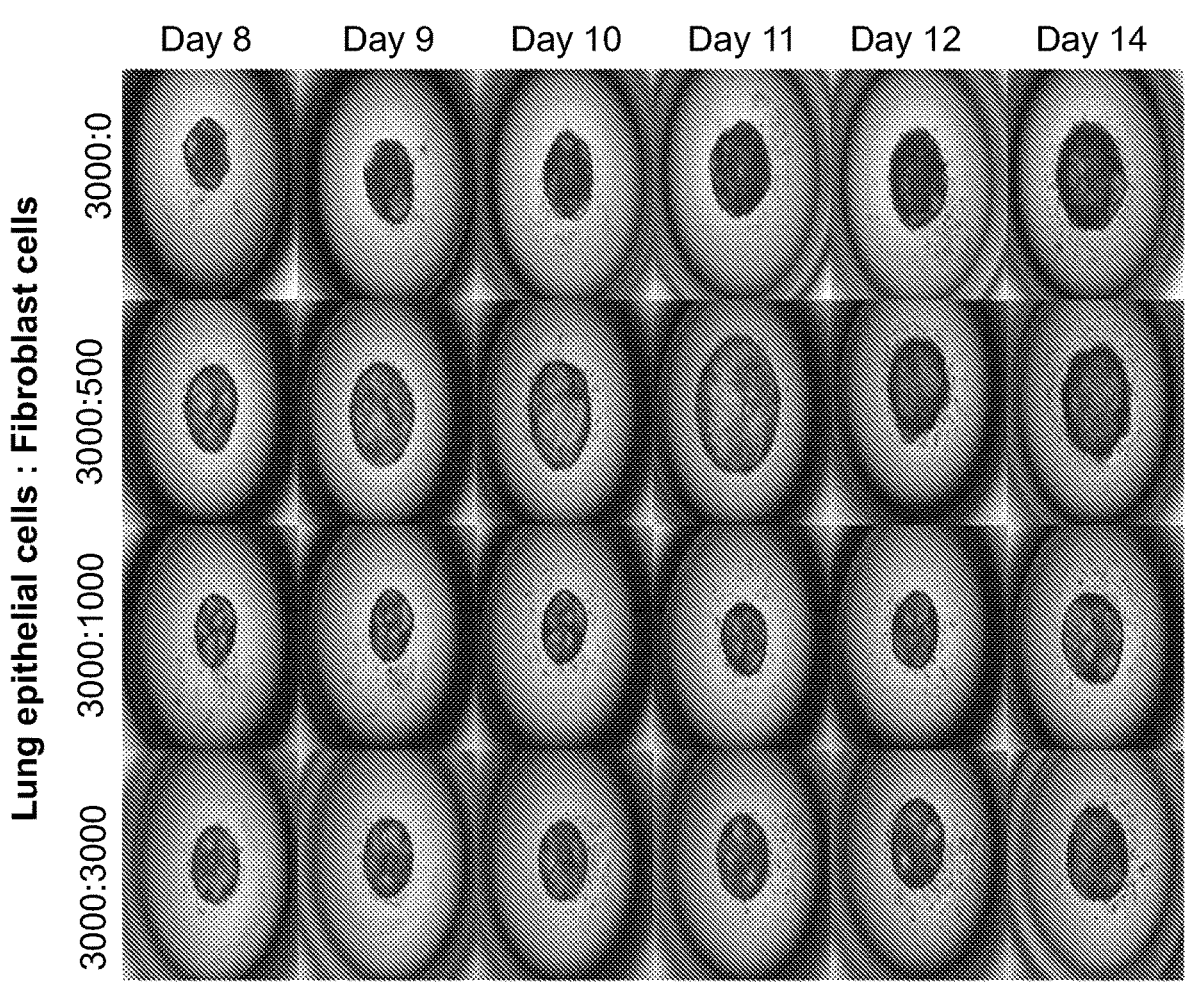

MCF10A organoids in high yield were obtained under various culture conditions with varying amounts of Matrigel and growth factors (RH-EGF or HB-EGF) at the time of seeding. The effect of EGF withdrawal at day 6 was also tested. FIGS. 37A and 37B show the effects of Matrigel and EGF types/concentrations on the organoid formation. The number of circles represents the number of organoids, while the average size of these organoids is shown with one circle in FIGS. 37A and 37B. The shading represents circularity and size of circle represents the average size of the organoids cultured under the specific condition. At the end of the culture period, organoids were fixed with 4% PFA and sectioned for histology. FIGS. 38A through 38C represent brightfield and immunostaining images of organoids obtained from culture in RH-EGF vs HB-EGF. When the growth factors are withdrawn, the outer layer of the organoid gets thinner over time.

Example 15: Cancer Invasion Experiments

MCF10A organoids were seeded as described using 3000 cells and grown in culture for 7 or 16 days. On day 7 or day 16 of culture, 300 MDA-MB-231 cells were introduced into each drop and the cultures were maintained for an additional 7-9 days. At the end of the experimental timepoint, the organoids were harvested, fixed, and prepared for cryohistology or optical clearing.

Example 16: Organoid Imaging and Morphology Analysis

While organoids were maintained in hanging drop culture, they were imaged every 2-3 days using an EVOS FL Auto 2 microscope (Thermo Fisher) with a 4× objective. For basic morphology analysis, Image J was utilized. The images were converted to binary, inverted, and the "Analyze Particles" macro was used to calculate both the area and roundness/circularity of the organoids.

Example 17: Sample Embedding and Cryosectioning

Organoids were harvested from the hanging drop plate upon completion of the experiment and washed 3 times in PBS. Samples were fixed in 4% paraformaldehyde (Alfa Aesar) for 1 hour at room temperature and washed with PBS. To aid in the visualization of the organoids, they were stained with 0.5% methylene blue (Ricca Chemical Company) for 10 minutes, followed by several PBS washes to remove the excess dye. A small amount of optimal cutting temperature (OCT) (Tissue-Tek) was added to a cryomold, and approximately 15 organoids were added to each mold. Subsequently, the organoids were covered with additional OCT. Isopentane (Sigma) was cooled in liquid nitrogen, and samples were flash frozen in the isopentane for less than 2 minutes. Cryoblocks were stored at −80° C., and 10 μm sections of the organoids were obtained using a CryoStar NX70 cryostat (Thermo Fisher).

Example 18: H&E Staining and Microscopy

Mounted sections were stored at −20° C. and thawed for 5 minutes prior to H&E staining. An ST5010 Autostainer XL (Leica) was used to perform the H&E staining. Samples were coverslipped with Xylene and Cytoseal 60 (Richard-Allan Scientific). The samples were imaged using a DMi1 inverted microscope equipped with a color camera and 10× objective (Leica).

Example 19: Immunofluorescence Staining and Microscopy

Mounted sections were rinsed with PBS and permeabilized with 0.2% Triton X-100 (Sigma) for 5 minutes. The sections were washed 3 times with PBS and blocked with 4% bovine serum albumin solution (BSA, Millipore Sigma, #82-067) for 1 hour at room temperature. Rabbit anti-E-cadherin (Cell signaling #3195, 1:200 dilution), Rabbit anti-laminin-1,2 (Thermo Fisher #PAI-16730, 1:1000 dilution), Rabbit anti-laminin 5 (Abcam #ab14509, 1:200 dilution), and Rabbit anti-integrin alpha-6 (Thermo Fisher #27189-1-AP, 1:500 dilution) primary antibodies were added to the samples, and incubated at 4° C. overnight. Primary antibodies were then removed, and samples were washed 3 times with 1% BSA solution in PBS. Secondary antibodies were incubated with the samples for 2 hours at room temperature. For all stains, Goat anti-Rabbit Alexa Fluor 594 was utilized as the secondary antibody (Invitrogen #A11012, 1:1000 dilution). Slides were rinsed 3 times with PBS, and incubated with DAPI (Thermo Fisher, 1.4 µM) for 15 minutes at room temperature. The slides were rinsed 3 times with PBS, briefly dried, and mounted using ProLong Diamond Antifade mounting media (ThermoFisher #P36965). A DMi8 inverted epifluorescence microscope (Leica) equipped with 10×, 20×, and 40× air objectives was used to image the samples.

Example 20: Optical Clearing, Confocal Microscopy, and Invasion Assessment

Organoids were collected from the hanging drop plate and fixed as previously described. The paraformaldehyde was then aspirated and the organoids were rinsed three times with PBS containing azide (Santa Cruz) and stored at 4° C. for clearing. The organoids were rinsed consecutively in ethanol-PBS solutions containing increasing fractions of ethanol to dehydrate: 50%, 70%, 80%, %%, and two rinses at 100%, 3 minutes per rinse on a gently rocking platform. Then, the organoids were transferred to a chambered glass slide, and submerged in the clearing solution of benzyl alcohol/benzyl benzoate (BABB, 1:2 (v/v)).

Imaging was conducted using a Perkin Elmer UltraView VoX spinning disc confocal microscope. Z-stacks were acquired with a 10× objective and 4.4 micron spacing. Confocal stacks were deconvolved using a calculated point spread function in Volocity Restoration software (Quorum Technologies) to better resolve relative cell positioning. The confocal stacks were analyzed in a double-blind manner; the images from the different timepoints were de-identified and then assessed for the presence of invasion by a different individual.

Example 21: Statistical Analysis

For quantification of morphological parameters, 20 organoids were used for each condition. The mean values are reported, and error bars represent the standard deviation.

Multiple t-tests were performed to analyze the difference in area and roundness between organoid culture with and without Matrigel for days 2, 4, 7, 10, 13, and 16 of culture. * denotes a p-value <0.005 and ** denotes a p-value <0.000001. For invasion experiments, n=8 organoids were used for the addition of MDA-MB-231 cells on day 7 and n=5 organoids for their addition on day 16. Bar graphs were produced to show the percentage of organoids exhibiting invasion for each condition.

Example 22: Normal Human Bronchial Epithelial Cell Monoculture Organoids

The process of hanging drop culture of normal human bronchial epithelial (NHBE) monoculture organoids is as described in above, with two critical differences. First, the seeding medium does not contain serum, as to accommodate requirements for primary cells. Second, the organoids are maintained in a medium that is different from the seeding medium. The maintenance medium consists of Wnt/β-catenin activator (R-Spodin1/CHIR99021), FGFR2b signaling activators (FGF7 & FGF10), TGF-β inhibitors (Noggin, LDN193189, A83-01), ROCK inhibitor (Y-27632), insulin signaling activator (B27), antioxidant (N-Acetylcysteine), co-enzyme precursor (nicotinamide), amino acid supplements (Glutamax, L-arginine, L-lysine), buffer components (Hepes), antibiotics (Penicillin/Streptomycin, Primocin).

Example 23: Lung Epithelial Cell and Fibroblast Co-Culture Organoids

Epithelial cell-fibroblast relationship provides important physiological interactions in many diseases. While direct intercellular contacts between the two cell types have been described previously, in vitro models that better recapitulate structural and functional complexity of real lungs need to be improved. In the inverted epithelial-fibroblast organoids described herein, fibroblasts fill up the core, whereas the epithelial cells make up layers around the boundary.

Figure 46:
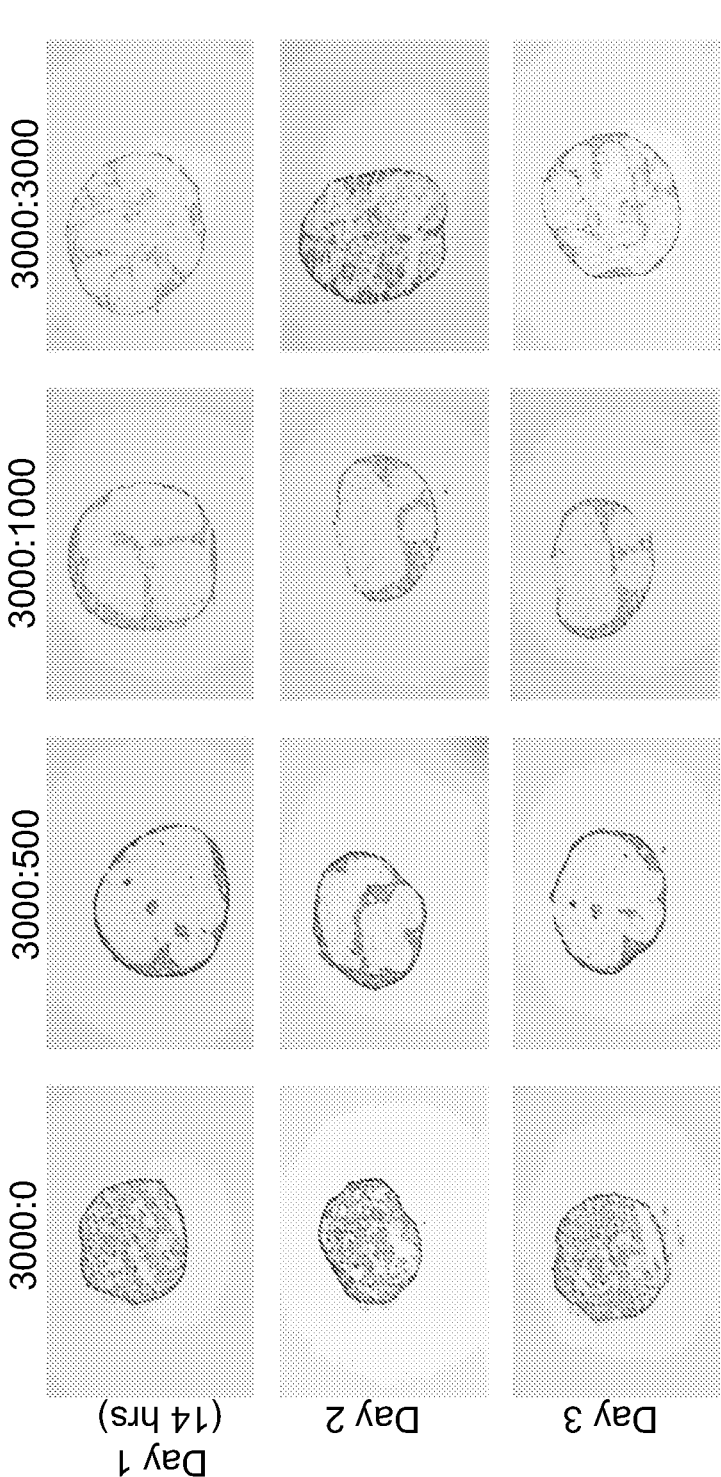
FIG. 46 shows H&E staining of lung epithelial organoid formation at Day 6 with varying concentrations of fibroblast co-culture, in accordance with an exemplary embodiment of the present disclosure.
Figure 47A:
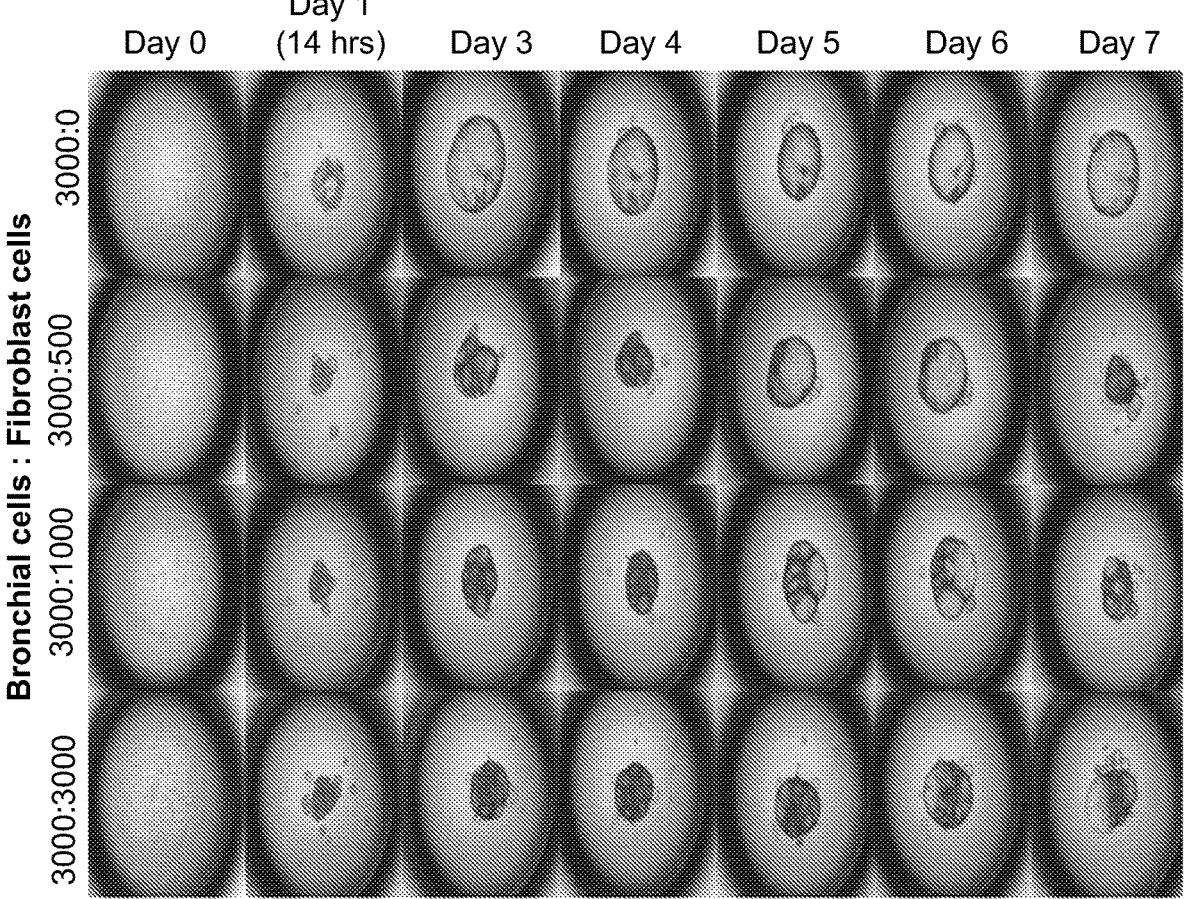
FIGS. 47A and 47B show normal human lung bronchial epithelial organoid formation over time with varying concentrations of fibroblast co-culture, in accordance with an exemplary embodiment of the present disclosure.
Figure 47B:
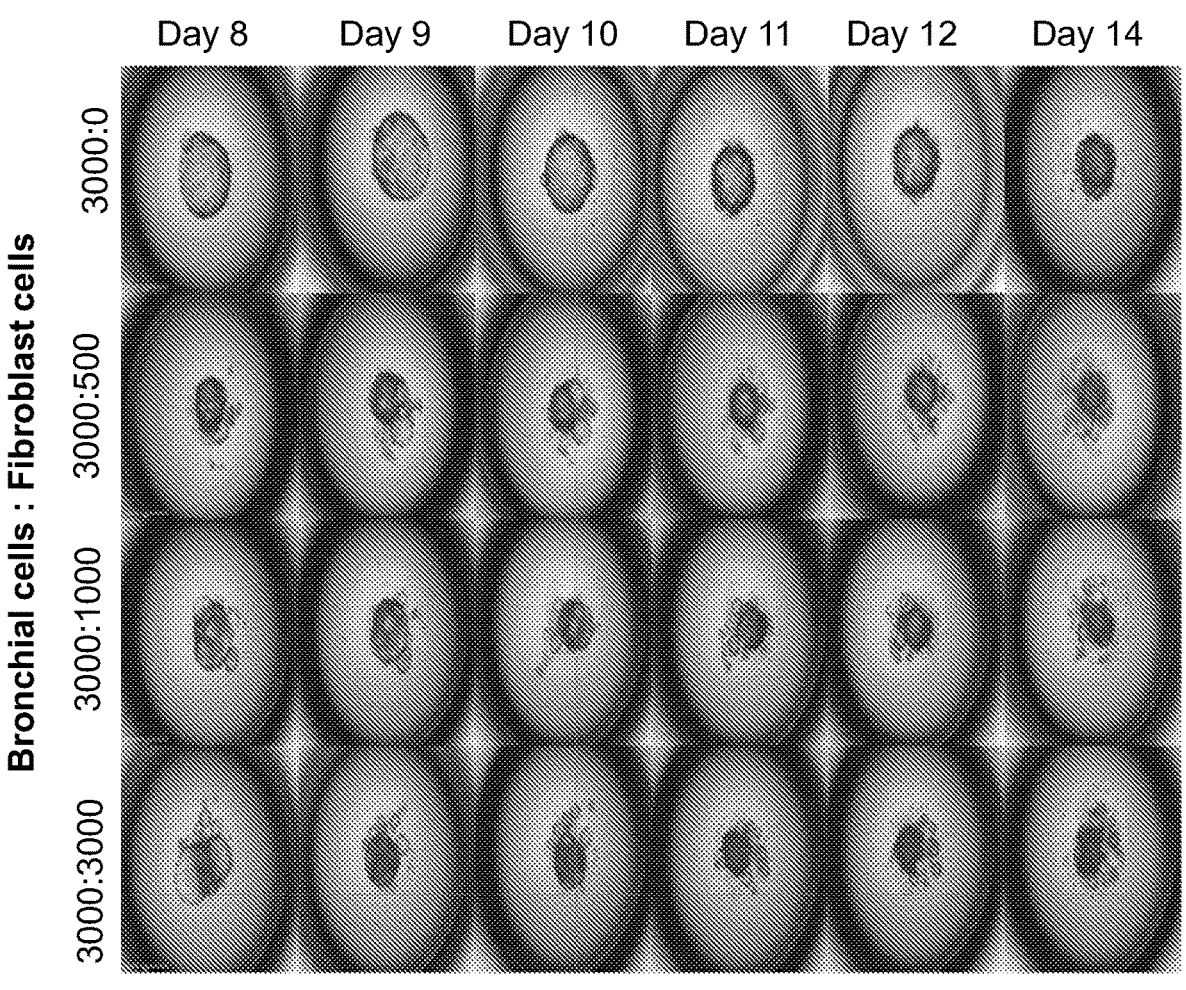
Figure 48:
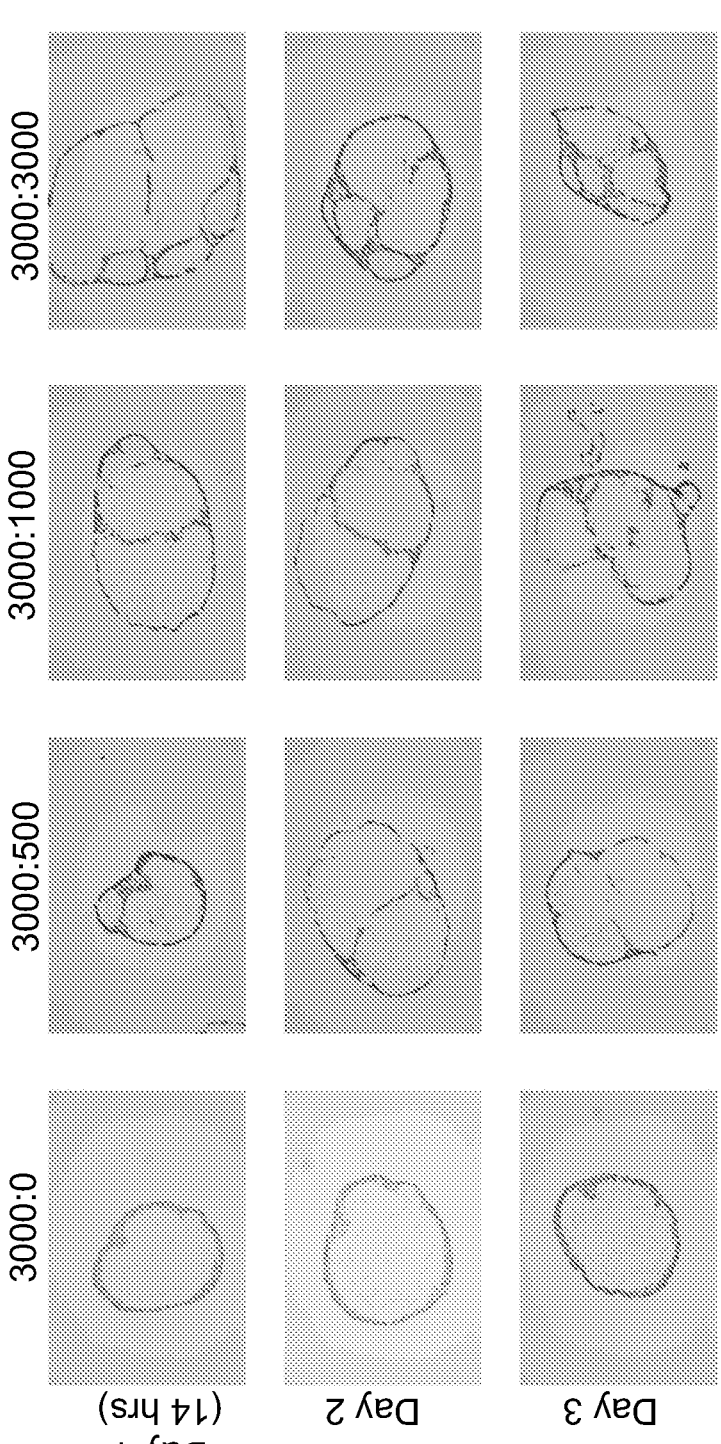
FIG. 48 shows H&E staining of bronchial organoid formation at Day 6 with varying concentrations of fibroblast co-culture, in accordance with an exemplary embodiment of the present disclosure.

Two types of lung epithelial cells were used for the co-culture model: NCI-H441 and NHBE. 3000 epithelial cells along with different numbers (500, 1000, 3000) of normal human fibroblasts (NHLF) were seeded and maintained in HD (FIGS. 45A, 45B, 47A, and 47B). As shown in H&E stain results (FIGS. 46 and 48), fibroblasts reside within the core, while epithelial cells create the boundary. Moreover, the more initial number of fibroblasts, the more fibroblasts were found in the core (FIGS. 46 and 48).

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

What is claimed is:

1. A 3D structure comprising:
   a tissue layer having a first surface defining at least a portion of an interior chamber and an opposing second surface;
   a plurality of first cells:
      supported on the second surface of the tissue layer so the first cells are outwardly positioned from the interior chamber:
      extending outwardly from the second surface of the tissue layer to an outwardly facing surface of first cells; and
      enclosing the interior chamber; and
   an extracellular matrix mixture contained within the enclosed interior chamber;
   wherein at least one of:
      the tissue layer comprises a basement membrane matrix;

the first surface of the tissue layer further comprises
stromal cells;

the first surface of the tissue layer further comprises a
transmembrane receptor;

the second surface of the tissue layer further comprises
an apical cell marker; or the second surface of the tissue layer further comprises
a second cell.

2. The 3D structure of claim 1, wherein:

the outwardly facing surface of first cells define an apical
surface of a polarized, differentiated epithelium or
endothelium configured to express an ACE2, a
TMPRSS2, a mucin, a transporter, a receptor, an alpha-
tubulin, an acetylated alpha-tubulin, or combinations
thereof.

3. The 3D structure of claim 2 wherein:

the epithelium comprises mammary cells, kidney cells,
lung cells, bladder cells, bronchial cells, tracheal cells,
alveolar cells, corneal cells, prostate cells, renal cells,
vaginal cells, cervical cells, intestine cells, or combi-
nations thereof; and the endothelium comprise primary coronary artery cells,
primary pulmonary artery cells, primary aortic cells,
primary dermal microvascular cells, primary umbilical
vein cells, brain artery cells, brachiocephalic artery
cells, internal thoracic artery cells, lymphatic endothe-
lial cells, or combinations thereof.

4. The 3D structure of claim 1 further comprising a
plurality of second cells;

wherein the second cells are positioned:

all within the interior chamber of the 3D structure;

all between the tissue layer and the first cells; or in portions both within the interior chamber of the 3D
structure and between the tissue layer and the first
cells.

5. The 3D structure of claim 4, wherein the second cells
are not epithelial or endothelial cells.

6. The 3D structure of claim 5, wherein the second cells
comprise one or more of myoepithelial cells, adipocytes,
fibrocytes, fibroblasts, myofibroblasts, pericytes, mesenchy-
mal stem cells, macrophages, mast cells, and lymphocytes.

7. The 3D structure of claim 1, wherein the 3D structure
comprises a diameter of about 1 mm to about 5 mm.

8. An organoid comprising:

an interior chamber comprising:

a plurality of first cells:

forming an external surface of the organoid; and having an outward facing surface expressing apical
molecules; ad a minimal extracellular matrix mixture gel surrounded
by the first cells;

wherein the outward facing surface of the first cells
interface directly with an environment external to the
organoid.

9. The organoid of claim 8 further comprising a tissue
layer positioned between the interior chamber of the organ-
oid and the first cells;

wherein the tissue layer:

comprises one or more of:

a basement membrane matrix;

stromal cells; or a transmembrane receptor; and interfaces with the interior chamber of the organoid.

10. A method of making a 3D structure comprising:

mixing an extracellular matrix mixture at a first tempera-
ture with a culture medium at a second temperature, the
second temperature greater than the first temperature;

culturing a plurality of first cells in the extracellular
matrix mixture and culture medium; and forming a 3D structure having an interior chamber defined
by the first cells that interface with an environment
external the 3D structure;

wherein the extracellular matrix mixture is entrapped
within the interior chamber of the 3D structure.

11. The method of claim 10 further comprising forming a
tissue layer between the first cells and the interior chamber
of the 3D structure.

12. The method of claim 11, wherein mixing comprises
mixing less than 1 mg/mL of the extracellular matrix mix-
ture with the culture medium.

13. The method of claim 11, wherein mixing comprises
mixing less than 500 µg/mL of the extracellular matrix
mixture with the culture medium.

14. The method of claim 11, wherein the second tempera-
ture is from about 20° C. to about 40° C.

15. The method of claim 11, wherein culturing comprises
culturing in a non-stick surface culture system selected from
the group consisting of a hanging drop system, an ultra-low
attachment system, a hydrogel well system, an ultrasound
levitation system, and a combination thereof.

16. The method of claim 15 further comprising culturing
a plurality of second cells;

wherein:

culturing the second cells is simultaneously with cul-
turing the first cells or after culturing the first cells;
and the second cells are not epithelial cells.

17. A method comprising:

making the 3D structure according to claim 10; and interfacing the first cells with the environment external
the 3D structure.

18. The method of claim 17, wherein from 5% to 100%
of the first cells interface with the environment external the
3D structure.

19. The method of claim 17 further comprising exposing
the 3D structure to a virus, a bacteria, a fungi, a cancer cell,
an immune cell, a stem cell, a drug, or combinations thereof.

* * * * *